(12) United States Patent
Nakamura et al.

(10) Patent No.: US 8,183,387 B2
(45) Date of Patent: May 22, 2012

(54) PHENYLPYRAZOLE DERIVATIVES

(75) Inventors: Toshio Nakamura, Toshima-ku (JP);
Makoto Tatsuzuki, Toshima-ku (JP);
Dai Nozawa, Toshima-ku (JP); Tomoko Tamita, Toshima-ku (JP); Seiji Masuda, Toshima-ku (JP); Hiroshi Ohta, Toshima-ku (JP); Shuhei Kashiwa, Toshima-ku (JP); Aya Fujino, Toshima-ku (JP); Shigeyuki Chaki, Toshima-ku (JP); Toshiharu Shimazaki, Toshima-ku (JP)

(73) Assignee: Taisho Pharmaceutical Co., Ltd, Tokyo (JP)

( * ) Notice: Subject to any disclaimer, the term of this patent is extended or adjusted under 35 U.S.C. 154(b) by 0 days.

(21) Appl. No.: 12/951,964

(22) Filed: Nov. 22, 2010

(65) Prior Publication Data

US 2011/0065667 A1    Mar. 17, 2011

Related U.S. Application Data

(62) Division of application No. 12/741,754, filed as application No. PCT/JP2008/070712 on Nov. 13, 2008, now Pat. No. 7,888,354.

(30) Foreign Application Priority Data

Nov. 13, 2007  (JP) .................. 2007-294040
Jun. 12, 2008  (JP) .................. 2008-153736

(51) Int. Cl.
*C07D 231/10*  (2006.01)
(52) U.S. Cl. .................. 548/364.1; 548/375.1
(58) Field of Classification Search .......... 548/377.1, 548/364.1, 375.1; 514/406
See application file for complete search history.

(56) References Cited

U.S. PATENT DOCUMENTS

| | | | |
|---|---|---|---|
| 6,316,475 B1 | 11/2001 | Bennani et al. | |
| 2006/0178375 A1 | 8/2006 | Ohtake et al. | |
| 2007/0105834 A1 | 5/2007 | Diaz Martin et al. | |
| 2008/0269287 A1 | 10/2008 | Ohtake et al. | |
| 2010/0113776 A1 | 5/2010 | Nakamura et al. | |

FOREIGN PATENT DOCUMENTS

| | | |
|---|---|---|
| WO | 02/12190 A2 | 2/2002 |
| WO | 02/40461 A2 | 5/2002 |
| WO | 02/074758 A2 | 9/2002 |
| WO | 2005/007644 A1 | 1/2005 |
| WO | 2005/097751 A2 | 10/2005 |
| WO | 2005/097778 A1 | 10/2005 |
| WO | 2005/118547 A1 | 12/2005 |
| WO | 2006/014136 A1 | 2/2006 |
| WO | 2006/023462 A1 | 3/2006 |
| WO | 2006/045416 A1 | 5/2006 |
| WO | 2006/046131 A1 | 5/2006 |
| WO | 2006/059778 A1 | 6/2006 |
| WO | 2006/061193 A1 | 6/2006 |
| WO | 2006/103045 A1 | 10/2006 |
| WO | 2006/103057 A1 | 10/2006 |
| WO | 2006/107661 A1 | 10/2006 |
| WO | 2007/009739 A1 | 1/2007 |
| WO | 2007/009741 A1 | 1/2007 |
| WO | 2007/094962 A2 | 8/2007 |
| WO | 2008/072724 A1 | 6/2008 |

OTHER PUBLICATIONS

"Alzheimer's Disease." (URL: <http://www.cnn.com/HEALTH/mentalhealth/alzheimers/#>) Retrieved online Dec. 1, 2011.*

(Continued)

*Primary Examiner* — Rebecca Anderson
*Assistant Examiner* — Samantha Shterengarts
(74) *Attorney, Agent, or Firm* — Sughrue Mion, PLLC

(57) ABSTRACT

The present invention provides a prophylactic or therapeutic agent for dementia, Alzheimer's disease, attention-deficit hyperactivity disorder, schizophrenia, eating disorders, obesity, diabetes, hyperlipidemia, sleep disorders, narcolepsy, sleep apnea syndrome, circadian rhythm disorder, depression, allergic rhinitis or other diseases.

A phenylpyrazole derivative represented by formula (1) or a pharmaceutically acceptable salt thereof:

[Formula 1]

$$
\text{(1)}
$$

{wherein
$R^1$ and $R^2$, which may be the same or different, each represent $C_1$-$C_6$ alkyl or $C_3$-$C_8$ cycloalkyl, or
$R^1$ and $R^2$ are attached to each other together with their adjacent nitrogen atom to form a 4- to 7-membered saturated heterocyclic ring (wherein said saturated heterocyclic ring may be substituted with halogen or $C_1$-$C_6$ alkyl),
n represents an integer of 0 to 2,
T represents a hydrogen atom, halogen or $C_1$-$C_6$ alkyl, and
R represents formula (I):

[Formula 2]

$$
\text{(I)}
$$

or the like}.

7 Claims, No Drawings

OTHER PUBLICATIONS

Faghig, R., et al., "Synthesis and SAR of Aminoalkoxy-biaryl-4-carboxamides: Novel and Selective Histamine H3 Receptor Antagonists", Bioorganic & Medicinal Chemistry Letters, vol. 13, pp. 1325-1328, 2003.

English translation of Explanation of Circumstances Concerning Accelerated Examination filed Feb. 5, 2010, as issued in Japanese Application No. 294040, filed Nov. 13, 2007.

European Search Report issued Aug. 23, 2011 by the European Patent Office, corresponding to European Patent Application No. 08849725.0.

Ishibuchi, S. et al., "Synthesis and Structure-Activity Relationships of 1-Phenylpyrazoles as Xanthine Oxidase Inhibitors," Bioorganic & Medicinal Chemistry Letters, Pergamon, Elsevier Science, GB, vol. 11, No. 7, Apr. 9, 2001, pp. 879-882.

\* cited by examiner

PHENYLPYRAZOLE DERIVATIVES

CROSS REFERENCE TO RELATED APPLICATIONS

This application is a divisional application of U.S. patent application Ser. No. 12/741,754, filed May 6, 2010 (now allowed), which is a National Stage of International Application No. PCT/JP2008/070712 filed Nov. 13, 2008, claiming priorities based on Japanese Patent Application Nos. 2007-294040 filed Nov. 13, 2007, and 2008-153736 filed Jun. 12, 2008, the contents of all of which are incorporated herein by reference in their entirety.

BACKGROUND ART

Histamine is usually stored within intracellular granules in mast cells, lung, liver and gastric mucosa, etc. In response to external stimuli such as antigen binding to cell surface antibody, histamine is released into the extracellular environment. For example, when mast cells are stimulated by an antigen entering from outside, histamine is released from the mast cells and stimulates histamine H1 (H1) receptors located on blood vessels or smooth muscle to cause allergic reactions. Likewise, histamine released from ECL cells (enterochromaffin-like cells) on the gastric mucosa stimulates histamine H2 (H2) receptors on the parietal cells to promote gastric acid secretion. Based on these facts, H1 and H2 receptor antagonists have been developed as therapeutic agents for allergic diseases and gastric ulcer, respectively, both of which are now used widely as medicaments.

Further, it has been elucidated that histamine serves as a neurotransmitter and acts on the third histamine receptor (histamine H3 (H3) receptor) located in central and peripheral nerves to thereby exert various physiological functions. This receptor was cloned in 1999 and determined for its gene sequence and amino acid sequence. However, its amino acid sequence homology was as low as 22% and 21.4% with H1 receptor and H2 receptor, respectively (see Non-patent Document 1). H3 receptors are present in the presynaptic membrane and are shown to serve as autoreceptors controlling the synthesis and release of histamine (see Non-patent Document 2). Moreover, H3 receptors are also shown to control not only the release of histamine, but also the release of other neurotransmitters including acetylcholine, serotonin, dopamine and noradrenaline (see Non-patent Document 3). It is also suggested that H3 receptors would be active in the absence of agonists, and their activity can be inhibited by compounds serving as inverse agonists. These facts suggest that H3 receptor antagonists or inverse agonists would enhance the release of H3 receptor-regulated neurotransmitters and may serve as therapeutic agents for various diseases related to abnormal release of these neurotransmitters.

Experiments in animal models indicate a possibility that H3 receptor antagonists or inverse agonists can be used as therapeutic agents for dementia, Alzheimer's disease (see Non-patent Documents 4 and 5), attention-deficit hyperactivity disorder (see Non-patent Document 6), schizophrenia (see Non-patent Document 7), epilepsy, central convulsion, etc.

Moreover, it is shown that H3 receptors are involved in eating behavior (see Non-patent Document 8); and hence possible target diseases for H3 receptor antagonists or inverse agonists also include metabolic diseases such as eating disorders, obesity, diabetes, hyperlipidemia, etc.

Further, it is shown that histamine regulates the circadian rhythm in the brain and is responsible for maintaining a balance between waking and sleeping states (see Non-patent Documents 9 and 10); and hence possible target diseases for H3 receptor antagonists or inverse agonists also include sleep disorders and diseases associated with sleep disorders such as narcolepsy, sleep apnea syndrome, circadian rhythm disorder, depression, etc.

Furthermore, it is shown that H3 receptors are present in sympathetic nerves on the nasal mucosa, and there is a report showing that the combined use of H3 and H1 receptor antagonists remarkably improves nasal congestion (see Non-patent Document 11). This indicates a possibility that H3 receptor antagonists or inverse agonists are useful for treatment of allergic rhinitis or other diseases, either alone or in combination with H1 receptor antagonists.

H3 receptor antagonists or inverse agonists have been summarized in several reviews (see Non-patent Documents 12 to 15), and reference may be made to these reviews. In the early years, many reports were issued for imidazole compounds starting from histamine itself as a leading compound. However, these compounds have not yet been developed as medicaments because they are feared to have negative effects such as inhibition of a drug-metabolizing enzyme, cytochrome P450 (CYP).

In recent years, many reports have been issued for non-imidazole H3 receptor antagonists or inverse agonists (see Patent Documents 1 to 15). However, there is no report about compounds having the structure disclosed in the present invention.

Patent Document 1: International Patent Publication No. WO2002/012190
Patent Document 2: International Patent Publication No. WO2002/040461
Patent Document 3: International Patent Publication No. WO2005/007644
Patent Document 4: International Patent Publication No. WO2005/097751
Patent Document 5: International Patent Publication No. WO2005/097778
Patent Document 6: International Patent Publication No. WO2005/118547
Patent Document 7: International Patent Publication No. WO2006/014136
Patent Document 8: International Patent Publication No. WO2006/023462
Patent Document 9: International Patent Publication No. WO2006/045416
Patent Document 10: International Patent Publication No. WO2006/046131
Patent Document 11: International Patent Publication No. WO2006/059778
Patent Document 12: International Patent Publication No. WO2006/061193
Patent Document 13: International Patent Publication No. WO2006/107661
Patent Document 14: International Patent Publication No. WO2006/103057
Patent Document 15: International Patent Publication No. WO2007/094962
Non-patent Document 1: Lovenberg T. W. et al., Molecular pharmacology, 55, 1101-1107, 1999
Non-patent Document 2: Arrang J-M. et al., Nature, 302, 832-837, 1983
Non-patent Document 3: Brown R. E. et al., Progress in Neurobiology, 63, 637-672, 2001
Non-patent Document 4: Huang Y-W. et al., Behavioural Brain Research, 151, 287-293, 2004
Non-patent Document 5: Komater V. A. et al., Behavioural Brain Research, 159, 295-300, 2005

Non-patent Document 6: Passani M. B. et al., Neuroscience and Biobehavioral Reviews, 24, 107-113, 2000

Non-patent Document 7: Fox G. B. et al., J. Pharmacol. Exp. Ther., 313, 176-190, Non-patent Document 8: Hancock A. A. et al., Curr. Opin. Investig. Drug, 4, 1190-1197

Non-patent Document 9: Huang Z-L. et al., Prog. Natr. Acad. Sci., 103, 4687-4692, 2006

Non-patent Document 10: Babier A. J. et al., Br. J. Pharmacol., 143, 649-661, 2004

Non-patent Document 11: McLeod R. L. et al., Am. J. Rhinol., 13, 391-399, 1999

Non-patent Document 12: Schwartz J. C. et al., Trends in Pharmacol. Sci., 7, 24-28, 1986

Non-patent Document 13: Passani M. B. et al., Trends in Pharmacol. Sci., 25, 618-625, 2004

Non-patent Document 14: Leurs R. et al., Nature Drug Discovery, 4, 107-122, 2005

Non-patent Document 15: Leurs R. et al., Drug Discovery Today, 10, 1613-1627, 2005

DISCLOSURE OF THE INVENTION

Problems to be Solved by the Invention

The object of the present invention is to provide phenylpyrazole derivatives, more specifically phenylpyrazole derivatives which have a strong inhibitory effect against binding to histamine H3 receptors and which are useful for prevention or treatment of histamine H3 receptor-mediated disorders such as dementia, Alzheimer's disease, attention-deficit hyperactivity disorder, schizophrenia, epilepsy, central convulsion, eating disorders, obesity, diabetes, hyperlipidemia, sleep disorders, narcolepsy, sleep apnea syndrome, circadian rhythm disorder, depression, allergic rhinitis or other diseases.

Means for Solving the Problems

As a result of extensive and intensive efforts, the inventors of the present invention have found that phenylpyrazole derivatives having a specific substituent at the 4-position of pyrazole have a strong inhibitory activity against histamine H3 receptors. This finding led to the completion of the present invention.

Embodiments will be given below for the phenylpyrazole derivatives of the present invention (hereinafter referred to as "the compounds of the present invention").

[1] A phenylpyrazole derivative represented by formula (1) or a pharmaceutically acceptable salt thereof:

[Formula 1]

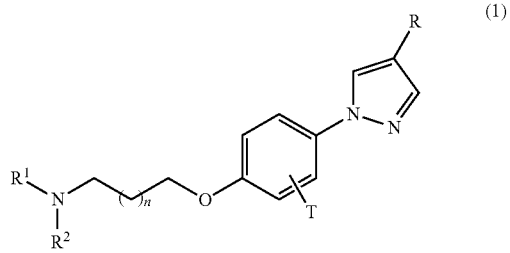

(1)

{wherein $R^1$ and $R^2$, which may be the same or different, each represent $C_1$-$C_6$ alkyl or $C_3$-$C_8$ cycloalkyl, or $R^1$ and $R^2$ are attached to each other together with their adjacent nitrogen atom to form a 4- to 7-membered saturated heterocyclic ring (wherein said saturated heterocyclic ring may be substituted with halogen or $C_1$-$C_6$ alkyl), n represents an integer of 0 to 2, T represents a hydrogen atom, halogen or $C_1$-$C_6$ alkyl, and R represents any one of formulae (I) to (VIII):

[Formula 2]

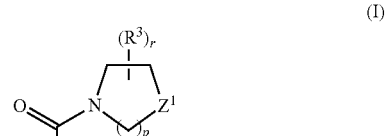

(I)

(II)

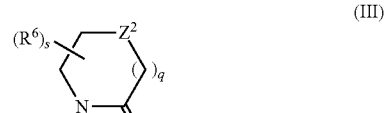

(III)

(IV)

(V)

(VI)

(VII)

(VIII)

(wherein $Z^1$ and $Z^2$, which may be the same or different, each represent —$CH_2$—, —O— or —$NR^{11}$—, p represents an integer of 0 to 3, q represents an integer of 0 to 1, r and s, which may be the same or different, each represent an integer of 0 to 2, $R^3$ represents halogen, $C_1$-$C_6$ alkyl, $C_1$-$C_6$ alkoxy, hydroxy or oxo (provided that when $Z^1$ is —$CH_2$—, the hydrogen atom(s) may be replaced by $R^3$), $R^4$ and $R^5$, which may be the same or different, each represent a hydrogen atom, $C_1$-$C_6$ alkyl (wherein said $C_1$-$C_6$ alkyl may be substituted with halogen, $C_3$-$C_8$ cycloalkyl, $C_1$-$C_6$ alkoxy, hydroxy, hydroxy-$C_1$-$C_6$ alkoxy, $C_2$-$C_7$ alkoxycarbonyl or carboxy), $C_3$-$C_8$ cycloalkyl (wherein said $C_3$-$C_8$ cycloalkyl may be substituted with halogen, $C_1$-$C_6$ alkyl, $C_1$-$C_6$ alkoxy or hydroxy) or the formula —$(CH_2)_m$—

Ar¹ (wherein Ar¹ represents aryl (wherein said aryl may be substituted with halogen, $C_1$-$C_6$ alkyl, $C_1$-$C_6$ alkoxy, hydroxy or cyano) or heteroaryl (wherein said heteroaryl may be substituted with halogen, $C_1$-$C_6$ alkyl, $C_1$-$C_6$ alkoxy, hydroxy or cyano), and m represents an integer of 0 to 2), $R^6$ represents halogen, $C_1$-$C_6$ alkyl, $C_1$-$C_6$ alkoxy, hydroxy or oxo (provided that when $Z^2$ is —$CH_2$—, the hydrogen atom(s) may be replaced by $R^6$), $R^7$ represents a hydrogen atom or $C_1$-$C_6$ alkyl, $R^8$ represents $C_1$-$C_6$ alkyl (wherein said $C_1$-$C_6$ alkyl may be substituted with halogen, $C_3$-$C_8$ cycloalkyl, $C_1$-$C_6$ alkoxy or hydroxy), $C_3$-$C_8$ cycloalkyl (wherein said $C_3$-$C_8$ cycloalkyl may be substituted with halogen, $C_1$-$C_6$ alkyl, $C_1$-$C_6$ alkoxy or hydroxy), $C_1$-$C_6$ alkoxy (wherein said $C_1$-$C_6$ alkoxy may be substituted with halogen, $C_3$-$C_8$ cycloalkyl, $C_1$-$C_6$ alkoxy or hydroxy) or the formula —$(CH_2)_l$—$Ar^2$ (wherein $Ar^2$ represents aryl (wherein said aryl may be substituted with halogen, $C_1$-$C_6$ alkyl, $C_1$-$C_6$ alkoxy, hydroxy or cyano) or heteroaryl (wherein said heteroaryl may be substituted with halogen, $C_1$-$C_6$ alkyl, $C_1$-$C_6$ alkoxy, hydroxy or cyano), and l represents an integer of 0 to 2), G represents —CO— or —$SO_2$—, $R^9$ represents $C_1$-$C_6$ alkyl, $C_3$-$C_8$ cycloalkyl, $C_1$-$C_6$ alkoxy, aryl (wherein said aryl may be substituted with halogen, $C_1$-$C_6$ alkyl, $C_1$-$C_6$ alkoxy, hydroxy or cyano) or heteroaryl (wherein said heteroaryl may be substituted with halogen, $C_1$-$C_6$ alkyl, $C_1$-$C_6$ alkoxy, hydroxy or cyano), $R^{10}$ represents $C_1$-$C_6$ alkyl, $C_1$-$C_6$ alkoxy, amino, $C_1$-$C_6$ alkylamino, $C_2$-$C_{12}$ dialkylamino, a 4- to 7-membered saturated heterocyclic ring (wherein said saturated heterocyclic ring may be substituted with halogen, $C_1$-$C_6$ alkyl, $C_1$-$C_6$ alkoxy, hydroxy or cyano), aryl (wherein said aryl may be substituted with halogen, $C_1$-$C_6$ alkyl, $C_1$-$C_6$ alkoxy, hydroxy or cyano) or heteroaryl (wherein said heteroaryl may be substituted with halogen, $C_1$-$C_6$ alkyl, $C_1$-$C_6$ alkoxy, hydroxy or cyano), and $R^{11}$ represents hydrogen or $C_1$-$C_6$ alkyl)}.

[2] A phenylpyrazole derivative represented by formula (1) or a pharmaceutically acceptable salt thereof:

[Formula 3]

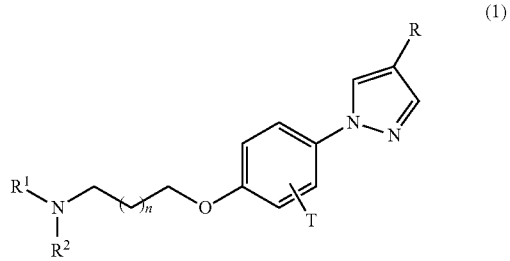

(1)

{wherein $R^1$ and $R^2$, which may be the same or different, each represent $C_1$-$C_6$ alkyl or $C_3$-$C_8$ cycloalkyl, or $R^1$ and $R^2$ are attached to each other together with their adjacent nitrogen atom to form a 4- to 7-membered saturated heterocyclic ring (wherein said saturated heterocyclic ring may be substituted with halogen or $C_1$-$C_6$ alkyl), n represents an integer of 0 to 2, T represents a hydrogen atom, halogen or $C_1$-$C_6$ alkyl, and R represents any one of formulae (I) to (VIII):

[Formula 4]

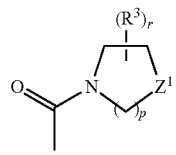

(I)

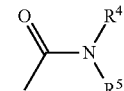

(II)

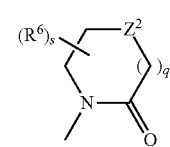

(III)

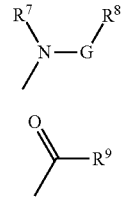

(IV)

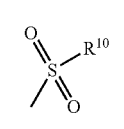

(V)

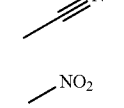

(VI)

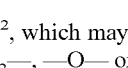

(VII)

(VIII)

(wherein $Z^1$ and $Z^2$, which may be the same or different, each represent —$CH_2$—, —O— or —NH—, p represents an integer of 0 to 3, q represents an integer of 0 to 1, r and s, which may be the same or different, each represent an integer of 0 to 2, $R^3$ represents halogen, $C_1$-$C_6$ alkyl, $C_1$-$C_6$ alkoxy or hydroxy (provided that when $Z^1$ is —$CH_2$— or —NH—, the hydrogen atom(s) may be replaced by $R^3$), $R^4$ and $R^5$, which may be the same or different, each represent a hydrogen atom, $C_1$-$C_6$ alkyl (wherein said $C_1$-$C_6$ alkyl may be substituted with halogen, $C_3$-$C_8$ cycloalkyl, $C_1$-$C_6$ alkoxy or hydroxy), $C_3$-$C_8$ cycloalkyl (wherein said $C_3$-$C_8$ cycloalkyl may be substituted with halogen, $C_1$-$C_6$ alkyl, $C_1$-$C_6$ alkoxy or hydroxy) or the formula —$(CH_2)_m$—$Ar^1$ (wherein $Ar^1$ represents aryl (wherein said aryl may be substituted with halogen, $C_1$-$C_6$ alkyl, $C_1$-$C_6$ alkoxy, hydroxy or cyano) or heteroaryl (wherein said heteroaryl may be substituted with halogen, $C_1$-$C_6$ alkyl, $C_1$-$C_6$ alkoxy, hydroxy or cyano), and m represents an integer of 0 to 2), $R^6$ represents halogen, $C_1$-$C_6$ alkyl, $C_1$-$C_6$ alkoxy, hydroxy or oxo (provided that when $Z^2$ is —$CH_2$— or —NH—, the hydrogen atom(s) may be replaced by $R^6$, and provided that when $Z^2$ is —NH—, $R^6$ is halogen, $C_1$-$C_6$ alkyl, $C_1$-$C_6$ alkoxy or hydroxy), $R^7$ represents a hydrogen atom or $C_1$-$C_6$ alkyl, $R^8$ represents $C_1$-$C_6$ alkyl (wherein said $C_1$-$C_6$ alkyl may be substituted with halogen, $C_3$-$C_8$ cycloalkyl, $C_1$-$C_6$ alkoxy or hydroxy), $C_3$-$C_8$ cycloalkyl (wherein said $C_3$-$C_8$ cycloalkyl may be substituted with halogen, $C_1$-$C_6$ alkyl, $C_1$-$C_6$ alkoxy or hydroxy), $C_1$-$C_6$ alkoxy (wherein said $C_1$-$C_6$ alkoxy may be substituted with halogen, $C_3$-$C_8$ cycloalkyl, $C_1$-$C_6$ alkoxy or hydroxy) or the formula —$(CH_2)_1$—$Ar^2$ (wherein $Ar^2$ represents aryl (wherein said aryl may be substituted with halogen, $C_1$-$C_6$ alkyl, $C_1$-$C_6$ alkoxy, hydroxy or cyano) or heteroaryl (wherein said heteroaryl may be substituted with halogen, $C_1$-$C_6$ alkyl, $C_1$-$C_6$ alkoxy, hydroxy or cyano), and 1 represents an integer of 0 to 2), G represents —CO— or —$SO_2$—, $R^9$ represents $C_1$-$C_6$ alkyl, $C_3$-$C_8$ cycloalkyl, $C_1$-$C_6$ alkoxy, aryl (wherein said aryl may be substituted with halogen, $C_1$-$C_6$ alkyl, $C_1$-$C_6$ alkoxy, hydroxy or cyano) or heteroaryl (wherein said heteroaryl may be substituted with halogen, $C_1$-$C_6$ alkyl, $C_1$-$C_6$ alkoxy, hydroxy or cyano), and $R^{10}$ represents $C_1$-$C_6$ alkyl, $C_1$-$C_6$ alkoxy, amino, $C_1$-$C_6$ alkylamino, $C_2$-$C_{12}$ dialkylamino, a 4- to 7-membered saturated heterocyclic ring (wherein said saturated heterocyclic ring may be substituted with halogen, $C_1$-$C_6$ alkyl, $C_1$-$C_6$ alkoxy, hydroxy or cyano), aryl (wherein said aryl may be substituted with halogen, $C_1$-$C_6$ alkyl, $C_1$-$C_6$ alkoxy, hydroxy or cyano) or heteroaryl (wherein said heteroaryl may be substituted with halogen, $C_1$-$C_6$ alkyl, $C_1$-$C_6$ alkoxy, hydroxy or cyano))}.

[3] A phenylpyrazole derivative represented by formula (1) or a pharmaceutically acceptable salt thereof:

[Formula 5]

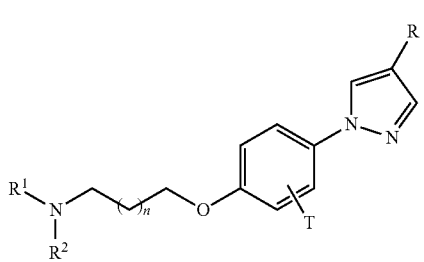
(1)

{wherein
$R^1$ and $R^2$, which may be the same or different, each represent $C_1$-$C_6$ alkyl or $C_3$-$C_8$ cycloalkyl, or $R^1$ and $R^2$ are attached to each other together with their adjacent nitrogen atom to form a 4- to 7-membered saturated heterocyclic ring (wherein said saturated heterocyclic ring may be substituted with halogen or $C_1$-$C_6$ alkyl), n represents an integer of 0 to 2, T represents a hydrogen atom, halogen or $C_1$-$C_6$ alkyl, and R represents any one of formulae (I) to (VIII):

[Formula 6]

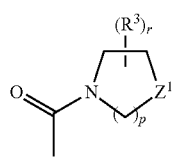
(I)

-continued

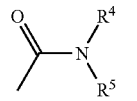
(II)

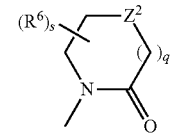
(III)

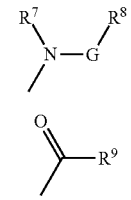
(IV)

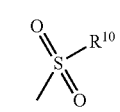
(V)

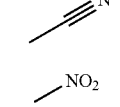
(VI)

(VII)

(VIII)

(wherein $Z^1$ and $Z^2$, which may be the same or different, each represent a carbon atom or an oxygen atom, p represents an integer of 0 to 2, q represents an integer of 0 to 1, r and s, which may be the same or different, each represent an integer of 0 to 2, $R^3$ represents halogen, $C_1$-$C_6$ alkyl, $C_1$-$C_6$ alkoxy or hydroxy, $R^4$ and $R^5$, which may be the same or different, each represent a hydrogen atom, $C_1$-$C_6$ alkyl (wherein said $C_1$-$C_6$ alkyl may be substituted with halogen, $C_3$-$C_8$ cycloalkyl, $C_1$-$C_6$ alkoxy or hydroxy), $C_3$-$C_8$ cycloalkyl (wherein said $C_3$-$C_8$ cycloalkyl may be substituted with halogen, $C_1$-$C_6$ alkyl, $C_1$-$C_6$ alkoxy or hydroxy), $C_1$-$C_6$ alkoxy (wherein said $C_1$-$C_6$ alkoxy may be substituted with halogen, $C_3$-$C_8$ cycloalkyl, $C_1$-$C_6$ alkoxy or hydroxy) or hydroxy) or the formula —$(CH_2)_m$—$Ar^1$ (wherein $Ar^1$ represents aryl (wherein said aryl may be substituted with halogen, $C_1$-$C_6$ alkyl, $C_1$-$C_6$ alkoxy, hydroxy or cyano) or heteroaryl (wherein said heteroaryl may be substituted with halogen, $C_1$-$C_6$ alkyl, $C_1$-$C_6$ alkoxy, hydroxy or cyano), and m represents an integer of 0 to 2), $R^6$ represents halogen, $C_1$-$C_6$ alkyl, $C_1$-$C_6$ alkoxy, hydroxy or oxo, $R^7$ represents a hydrogen atom or $C_1$-$C_6$ alkyl, $R^8$ represents $C_1$-$C_6$ alkyl (wherein said $C_1$-$C_6$ alkyl may be substituted with halogen, $C_3$-$C_8$ cycloalkyl, $C_1$-$C_6$ alkoxy or hydroxy), $C_3$-$C_8$ cycloalkyl (wherein said $C_3$-$C_8$ cycloalkyl may be substituted with halogen, $C_1$-$C_6$ alkyl, $C_1$-$C_6$ alkoxy or hydroxy), $C_1$-$C_6$ alkoxy (wherein said $C_1$-$C_6$ alkoxy may be substituted with halogen, $C_3$-$C_8$ cycloalkyl, $C_1$-$C_6$ alkoxy or hydroxy) or the formula —$(CH_2)_1$—$Ar^2$ (wherein $Ar^2$ represents aryl (wherein said aryl may be substituted with halogen, $C_1$-$C_6$ alkyl, $C_1$-$C_6$ alkoxy, hydroxy or cyano) or heteroaryl (wherein said heteroaryl may be substituted with halogen, $C_1$-$C_6$ alkyl, $C_1$-$C_6$ alkoxy, hydroxy or cyano), and 1 represents an integer of 0 to 2), G represents —CO— or —SO$_2$—, R$^9$ represents C$_1$-C$_6$ alkyl, C$_3$-C$_8$ cycloalkyl, C$_1$-C$_6$ alkoxy, aryl (wherein said aryl may be substituted with halogen, C$_1$-C$_6$ alkyl, C$_1$-C$_6$ alkoxy, hydroxy or cyano) or heteroaryl (wherein said heteroaryl may be substituted with halogen, C$_1$-C$_6$ alkyl, C$_1$-C$_6$ alkoxy, hydroxy or cyano), and R$^{10}$ represents C$_1$-C$_6$ alkyl, C$_1$-C$_6$ alkoxy, amino, C$_1$-C$_6$ alkylamino, C$_2$-C$_{12}$ dialkylamino, a 4- to 7-membered saturated heterocyclic ring (wherein said saturated heterocyclic ring may be substituted with halogen, C$_1$-C$_6$ alkyl, C$_1$-C$_6$ alkoxy, hydroxy or cyano), aryl (wherein said aryl may be substituted with halogen, C$_1$-C$_6$ alkyl, C$_1$-C$_6$ alkoxy, hydroxy or cyano) or heteroaryl (wherein said heteroaryl may be substituted with halogen, C$_1$-C$_6$ alkyl, C$_1$-C$_6$ alkoxy, hydroxy or cyano))}.

[4] The phenylpyrazole derivative or pharmaceutically acceptable salt thereof according to any one of [1] to [3] above, wherein in formula (1), n is 1, T represents a hydrogen atom or halogen, and R$^1$ and R$^2$ are attached to each other together with their adjacent nitrogen atom to form a 5- to 6-membered saturated heterocyclic ring (wherein said saturated heterocyclic ring may be substituted with C$_1$-C$_6$ alkyl).

[5] The phenylpyrazole derivative or pharmaceutically acceptable salt thereof according to any one of [1] to [4] above, wherein in formula (1), R is formula (I).

[6] The phenylpyrazole derivative or pharmaceutically acceptable salt thereof according to any one of [1] to [4] above, wherein in formula (1), R is formula (II).

[7] The phenylpyrazole derivative or pharmaceutically acceptable salt thereof according to any one of [1] to [4] above, wherein in formula (1), R is formula (III).

[8] The phenylpyrazole derivative or pharmaceutically acceptable salt thereof according to [1] above, which is represented by the following formula:

[Formula 7]

{wherein Z$^1$ represents —CH$_2$— or —O—, p represents an integer of 0 to 3, r represents an integer of 0 to 2, T represents a hydrogen atom or halogen, R$^3$ represents halogen, C$_1$-C$_6$ alkyl, C$_1$-C$_6$ alkoxy, hydroxy or oxo (provided that when Z$^1$ is —CH$_2$—, the hydrogen atom(s) may be replaced by R$^3$), and R$^A$ represents C$_1$-C$_6$ alkyl}.

[9] The phenylpyrazole derivative or pharmaceutically acceptable salt thereof according to [1] above, which is represented by the following formula:

[Formula 8]

{wherein Z$^1$ represents —O— or —NR$^{11}$— (wherein R$^{11}$ represents hydrogen or C$_1$-C$_6$ alkyl), p represents an integer of 0 to 3, r represents an integer of 0 to 2, and R$^3$ represents halogen, C$_1$-C$_6$ alkyl, C$_1$-C$_6$ alkoxy, hydroxy or oxo}.

[10] The phenylpyrazole derivative or pharmaceutically acceptable salt thereof according to any one of [1] to [5] above, which is selected from the group consisting of:

4-{[1-(4-{3-[(2R)-2-methylpyrrolidin-1-yl]propoxy}phenyl)-1H-pyrazol-4-yl]carbonyl}morpholine, 4-{[1-(4-{3-[(2S)-2-methylpyrrolidin-1-yl]propoxy}phenyl)-1H-pyrazol-4-yl]carbonyl}morpholine, 4-({1-[4-(3-pyrrolidin-1-ylpropoxy)phenyl]-1H-pyrazol-4-yl}carbonyl)morpholine, 4-({1-[4-(3-piperidin-1-ylpropoxy)phenyl]-1H-pyrazol-4-yl}carbonyl)morpholine, 4-[(1-{4-[3-(2,2-dimethylpyrrolidin-1-yl)propoxy]phenyl}-1H-pyrazol-4-yl)carbonyl]morpholine, azetidin-1-yl-(1-{4-[3-(2-methylpyrrolidin-1-yl)propoxy]phenyl}-1H-pyrazol-4-yl)methanone, 4-[(3,3-difluoropyrrolidin-1-yl)carbonyl]-1-(4-{3-[(2R)-2-methylpyrrolidin-1-yl]propoxy}phenyl)-1H-pyrazole,

[(2R,6S)-2,6-dimethylmorpholin-4-yl][1-(4-{3-[(2R)-2-methylpyrrolidin-1-yl]propoxy}phenyl)-1H-pyrazol-4-yl]methanone,

[1-(4-{3-[(2R)-2-methylpyrrolidin-1-yl]propoxy}phenyl)-1H-pyrazol-4-yl](1,4-oxazepan-4-yl)methanone, (4-methylpiperazin-1-yl)[1-(4-{3-[(2R)-2-methylpyrrolidin-1-yl]propoxy}phenyl)-1H-pyrazol-4-yl]methanone,

[1-(4-{3-[(2R)-2-methylpyrrolidin-1-yl]propoxy}phenyl)-1H-pyrazol-4-yl](pyrrolidin-1-yl)methanone, (1-{4-[3-(3-methylpyrrolidin-1-yl)propoxy]phenyl}-1H-pyrazol-4-yl)(morpholin-4-yl)methanone, (1-{4-[3-(2-ethylpyrrolidin-1-yl)propoxy]phenyl}-1H-pyrazol-4-yl)(morpholin-4-yl)methanone, (1-{4-[3-(2,2-difluoropyrrolidin-1-yl)propoxy]phenyl}-1H-pyrazol-4-yl)(morpholin-4-yl)methanone,

[1-(4-{2-[(2R)-2-methylpyrrolidin-1-yl]ethoxy}phenyl)-1H-pyrazol-4-yl](morpholin-4-yl)methanone,

[1-(4-{4-[(2R)-2-methylpyrrolidin-1-yl]butoxy}phenyl)-1H-pyrazol-4-yl](morpholin-4-yl)methanone,

[1-(3-fluoro-4-{3-[(2R)-2-methylpyrrolidin-1-yl]propoxy}phenyl)-1H-pyrazol-4-yl](morpholin-4-yl)methanone,

[1-(2-methyl-4-{3-[(2R)-2-methylpyrrolidin-1-yl]propoxy}phenyl)-1H-pyrazol-4-yl](morpholin-4-yl)methanone,

[1-(3-bromo-4-{3-[(2R)-2-methylpyrrolidin-1-yl]propoxy}phenyl)-1H-pyrazol-4-yl](morpholin-4-yl)methanone, and (2-hydroxymorpholin-4-yl)[1-(4-{3-[(2R)-2-methylpyrrolidin-1-yl]propoxy}phenyl)-1H-pyrazol-4-yl]methanone.

[11] The phenylpyrazole derivative or pharmaceutically acceptable salt thereof according to any one of [1] to [4] and [6] above, which is selected from the group consisting of:

1-(4-{3-[(2R)-2-methylpyrrolidin-1-yl]propoxy}phenyl)-1H-pyrazole-4-carboxamide,
1-(4-{3-[(2S)-2-methylpyrrolidin-1-yl]propoxy}phenyl)-1H-pyrazole-4-carboxamide,
N-tert-butyl-1-{4-[3-(2-methylpyrrolidin-1-yl)propoxy]phenyl}-1H-pyrazole-4-carboxamide,
N-tert-butyl-1-{4-[3-(2,5-dimethylpyrrolidin-1-yl)propoxy]phenyl}-1H-pyrazole-4-carboxamide,
N-tert-butyl-1-[4-(3-pyrrolidin-1-ylpropoxy)phenyl]-1H-pyrazole-4-carboxamide,
N-tert-butyl-1-{4-[3-(diethylamino)propoxy]phenyl}-1H-pyrazole-4-carboxamide,
N-(4-fluorophenyl)-1-{4-[3-(2-methylpyrrolidin-1-yl)propoxy]phenyl}-1H-pyrazole-4-carboxamide,
N-(4-fluorophenyl)-1-[4-(3-pyrrolidin-1-ylpropoxy)phenyl]-1H-pyrazole-4-carboxamide,
N-(4-methylphenyl)-1-{4-[3-(2-methylpyrrolidin-1-yl)propoxy]phenyl}-1H-pyrazole-4-carboxamide,
1-{4-[3-(2-methylpyrrolidin-1-yl)-propoxy]-phenyl}-1H-pyrazole-4-carboxylic acid 4-fluorobenzylamide,
1-{4-[3-(2-methylpyrrolidin-1-yl)-propoxy]-phenyl}-1H-pyrazole-4-carboxylic acid dimethylamide,
1-(4-{3-[(2R)-2-methylpyrrolidin-1-yl]propoxy}phenyl)-1H-pyrazole-4-carboxylic acid bis-(2-hydroxyethyl)-amide,
N-(2-hydroxyethyl)-1-(4-{3-[(2R)-2-methylpyrrolidin-1-yl]propoxy}phenyl)-1H-pyrazole-4-carboxamide,
tert-butyl N-(2-hydroxyethyl)-N-{[1-(4-{3-[(2R)-2-methylpyrrolidin-1-yl]propoxy}phenyl)-1H-pyrazol-4-yl]carbonyl}glycinate,
N-(2-hydroxyethyl)-N-{[1-(4-{3-[(2R)-2-methylpyrrolidin-1-yl]propoxy}phenyl)-1H-pyrazol-4-yl]carbonyl}glycine, and
N-[2-(2-hydroxyethoxy)ethyl]-1-(4-{3-[(2R)-2-methylpyrrolidin-1-yl]propoxy}phenyl)-1H-pyrazole-4-carboxamide.

[12] A prophylactic or therapeutic agent for dementia, Alzheimer's disease, attention-deficit hyperactivity disorder, schizophrenia, epilepsy, central convulsion, eating disorders, obesity, diabetes, hyperlipidemia, sleep disorders, narcolepsy, sleep apnea syndrome, circadian rhythm disorder, depression or allergic rhinitis, which comprises the phenylpyrazole derivative or pharmaceutically acceptable salt thereof according to any one of [1] to [11] above as an active ingredient.

Advantages of the Invention

The compounds of the present invention are excellent histamine H3 receptor antagonists or inverse agonists.

BEST MODE FOR CARRYING OUT THE INVENTION

The terms and expressions used herein are defined as follows.

As used herein, the term "halogen" refers to a fluorine atom, a chlorine atom, a bromine atom or an iodine atom.

The term "$C_1$-$C_6$ alkyl" refers to a linear or branched alkyl group containing 1 to 6 carbon atoms, including methyl, ethyl, n-propyl, isopropyl, n-butyl, isobutyl, sec-butyl, tert-butyl, n-pentyl, isopentyl, neopentyl and n-hexyl groups.

The term "$C_3$-$C_8$ cycloalkyl" refers to a cyclic alkyl group containing 3 to 8 carbon atoms, including cyclopropyl, cyclobutyl, cyclopentyl, cyclohexyl, cycloheptyl and cyclooctyl groups.

The term "$C_1$-$C_6$ alkoxy" refers to a linear or branched alkoxy group containing 1 to 6 carbon atoms, including methoxy, ethoxy, n-propoxy, isopropoxy, n-butoxy, isobutoxy, sec-butoxy, tert-butoxy, n-pentyloxy, isopentyloxy, neopentyloxy and n-hexyloxy groups.

The term "$C_2$-$C_7$ alkoxycarbonyl" refers to a carbonyl group attached to a linear or branched alkoxy group containing 1 to 6 carbon atoms, including methoxycarbonyl, ethoxycarbonyl, n-propoxycarbonyl, isopropoxycarbonyl, n-butoxycarbonyl, isobutoxycarbonyl, sec-butoxycarbonyl, tert-butoxycarbonyl, n-pentyloxycarbonyl, isopentyloxycarbonyl, neopentyloxycarbonyl and n-hexyloxycarbonyl groups.

The term "hydroxy-$C_1$-$C_6$ alkoxy" refers to a hydroxy-substituted linear or branched alkoxy group containing 1 to 6 carbon atoms, including 2-hydroxyethoxy, 2-hydroxy-n-propoxy, 3-hydroxy-n-propoxy, 2-hydroxy-1-methylethoxy and 6-hydroxy-n-hexyloxy groups.

The term "$C_1$-$C_6$ alkylamino" refers to an amino group substituted with a linear or branched alkyl group containing 1 to 6 carbon atoms, including methylamino, ethylamino, n-propylamino, isopropylamino, n-butylamino, isobutylamino, sec-butylamino, tert-butylamino, n-pentylamino, isopentylamino, neopentylamino and n-hexylamino groups.

The term "$C_2$-$C_{12}$ dialkylamino" refers to an amino group substituted with two linear or branched alkyl groups each containing 1 to 6 carbon atoms, including dimethylamino, diethylamino, di-n-propylamino, N,N-isopropylmethylamino, di-n-butylamino, diisobutylamino, N,N-sec-butylethylamino, N,N-tert-butylmethylamino, di-n-pentylamino, N,N-isopentylmethylamino, N,N-neopentylmethylamino and di-n-hexylamino groups.

The term "4- to 7-membered saturated heterocyclic ring" refers to, e.g., a 1-azetidyl, 1-pyrrolidyl, piperidino, morpholino or 1-azepanyl group.

The expression "attached to each other together with their adjacent nitrogen atom to form a 4- to 7-membered saturated heterocyclic ring" is intended to mean, e.g., a 1-azetidyl, 1-pyrrolidyl, piperidino, morpholino or 1-azepanyl group.

The term "aryl" refers to a phenyl group or a naphthyl group.

The term "heteroaryl" refers to a group composed of a 5- or 6-membered monocyclic or 9- or 10-membered bicyclic aromatic heterocyclic ring. Examples include pyridyl, pyridazinyl, pyrimidinyl, pyrazinyl, quinolinyl, isoquinolinyl, quinazolinyl, quinoxalinyl, pyrrolyl, furanyl, thiophenyl, pyrazolyl, imidazolyl, oxazolyl, isoxazolyl, thiazolyl, isothiazolyl, triazolyl, indolyl, benzofuranyl, benzothiophenyl, benzoimidazolyl, indazolyl, benzoxazolyl, benzothiazolyl and benzotriazolyl groups. More specific examples include 2-pyridyl, 3-pyridyl, 4-pyridyl, pyridazin-3-yl, pyridazin-4-yl, pyrimidin-2-yl, pyrimidin-4-yl, pyrimidin-5-yl, pyrazin-2-yl, quinolin-2-yl, quinolin-4-yl, quinolin-6-yl, quinolin-8-yl, isoquinolin-1-yl, isoquinolin-6-yl, quinazolin-2-yl, quinazolin-5-yl, quinoxalin-2-yl, quinoxalin-6-yl, pyrrol-3-yl, furan-2-yl, furan-3-yl, thiophen-2-yl, thiophen-3-yl, pyrazol-3-yl, pyrazol-4-yl, imidazol-2-yl, oxazol-2-yl, oxazol-4-yl, isoxazol-3-yl, thiazol-2-yl, thiazol-5-yl, isothiazol-4-yl, 1,2,4-triazol-3-yl, indol-2-yl, indol-5-yl, indol-7-yl, benzofuran-3-yl, benzothiophen-3-yl, benzoimidazol-2-yl, indazol-5-yl, benzoxazol-2-yl, benzothiazol-2-yl and benzotriazol-4-yl groups.

Preferred embodiments will be given below for the compounds of the present invention.

n is preferably 1.

T is preferably a hydrogen atom or halogen.

One preferred embodiment of R is formula (I) shown below.

[Formula 9]

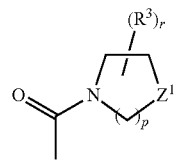

(I)

In formula (I), $Z^1$ represents —$CH_2$—, —O— or —$NR^{11}$— (wherein $R^{11}$ represents hydrogen or $C_1$-$C_6$ alkyl), p represents an integer of 0 to 3, r represents an integer of 0 to 2, and $R^3$ represents halogen, $C_1$-$C_6$ alkyl, $C_1$-$C_6$ alkoxy, hydroxy or oxo (provided that when $Z^1$ is —$CH_2$—, the hydrogen atom(s) may be replaced by $R^3$).

Preferred embodiments for the structure of formula (I) are represented by the following formulae:

[Formula 10]

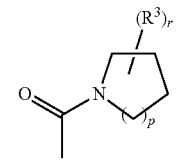

Ia

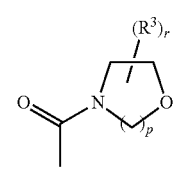

Ib

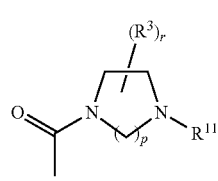

Ic (wherein $R^3$, $R^{11}$, p and r are as defined above).

$R^3$ is preferably halogen, $C_1$-$C_6$ alkyl or hydroxy.

$R^{11}$ is preferably $C_1$-$C_6$ alkyl.

In formula (Ia), p preferably represents an integer of 1 to 2.

In formulae (Ib) and (Ic), p preferably represents an integer of 2 to 3.

A more preferred embodiment for the structure of formula (I) is represented by the following formula.

[Formula 11]

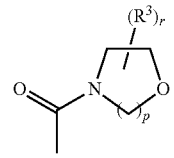

Another preferred embodiment of R is formula (II) shown below.

[Formula 12]

(II)

In formula (II), $R^4$ and $R^5$, which may be the same or different, preferably each represent a hydrogen atom, $C_1$-$C_6$ alkyl (wherein said $C_1$-$C_6$ alkyl may be substituted with halogen, $C_3$-$C_8$ cycloalkyl, $C_1$-$C_6$ alkoxy, hydroxy, or hydroxy-$C_1$-$C_6$ alkoxy) or the formula —$(CH_2)_m$—$Ar^1$ (wherein $Ar^1$ represents aryl (wherein said aryl may be substituted with halogen, $C_1$-$C_6$ alkyl, $C_1$-$C_6$ alkoxy, hydroxy or cyano), and m represents an integer of 0 to 2).

Yet another preferred embodiment of R is formula (III) shown below.

[Formula 13]

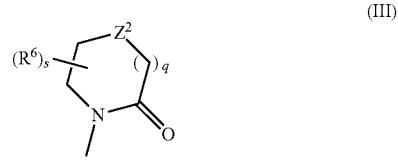

(III)

In formula (III), $Z^2$ represents —$CH_2$—, —O— or —$NR^{11}$— (wherein $R^{11}$ represents hydrogen or $C_1$-$C_6$ alkyl), q represents an integer of 0 to 1, s represents an integer of 0 to 2, and $R^6$ represents halogen, $C_1$-$C_6$ alkyl, $C_1$-$C_6$ alkoxy, hydroxy or oxo (provided that when $Z^2$ is —$CH_2$—, the hydrogen atom(s) may be replaced by $R^6$).

Preferred embodiments for the structure of formula (III) are represented by the following formulae:

[Formula 14]

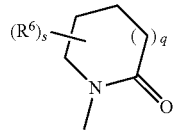

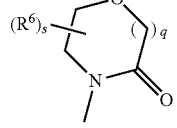

(wherein $R^6$, s and q are as defined above).

s preferably represents an integer of 0 to 1.

Likewise, in a preferred embodiment of —NR¹R², R¹ and R² are attached to each other together with their adjacent nitrogen atom to form a 5- to 6-membered saturated heterocyclic ring (e.g., 1-pyrrolidyl, piperidino) (wherein said saturated heterocyclic ring may be substituted with $C_1$-$C_6$ alkyl). In the case of 1-pyrrolidyl, it is preferably substituted with one $C_1$-$C_6$ alkyl at the 2-position.

A more preferred embodiment of —NR¹R² is a group represented by the following formula.

[Formula 15]

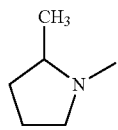

An even more preferred embodiment of —NR¹R² is a group represented by the following formula.

[Formula 16]

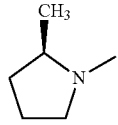

Moreover, to determine pharmaceutical utility, various aspects of compounds should be evaluated, including not only their main activity, but also their side effects and toxicity. More specifically, when compounds are targeted for H3 receptor inhibition, since opioid receptors are involved in the regulatory mechanism of brain functions, the compounds may have side effects such as dependence, dysphoria, depression-like symptoms if they also have an affinity for μ, δ and κ receptors. On the other hand, when compounds have an antagonistic effect against σ1 receptors, they will affect acetylcholine release and NMDA receptor functions, and hence cannot exert a sufficient enhancing effect on cognitive functions. These findings are reported in J. Pharmacol. Exp. Ther., 2002, Arp, 301(1), 249-257 and Neuropsychopharmacology, 2007, March, 32(3), 514-521. Thus, there is a demand for compounds that have no affinity for opioid receptors and selectively act on H3 receptors.

Compounds preferred in terms of low affinity for opioid receptors are phenylpyrazole derivatives or pharmaceutically acceptable salts thereof, which have a specific substituent at the 4-position of pyrazole and further have other substituents as defined below:

[Formula 17]

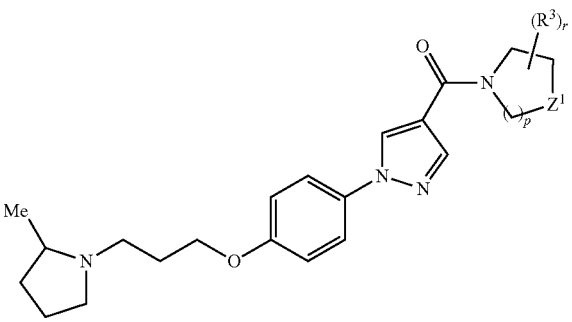

{wherein $Z^1$ represents —O— or —NR¹¹— (wherein R¹¹ represents hydrogen or $C_1$-$C_6$ alkyl),
p represents an integer of 0 to 3,
r represents an integer of 0 to 2, and
R³ represents halogen, $C_1$-$C_6$ alkyl, $C_1$-$C_6$ alkoxy, hydroxy or oxo}.

A preferred embodiment for the above formula is as follows: $Z^1$ is preferably —O—, R³ is preferably halogen, $C_1$-$C_6$ alkyl or hydroxy, and r is preferably 0.

Compounds preferred in terms of low cytotoxicity are phenylpyrazole derivatives or pharmaceutically acceptable salts thereof, which have a specific substituent at the 4-position of pyrazole and further have other substituents as defined below:

[Formula 18]

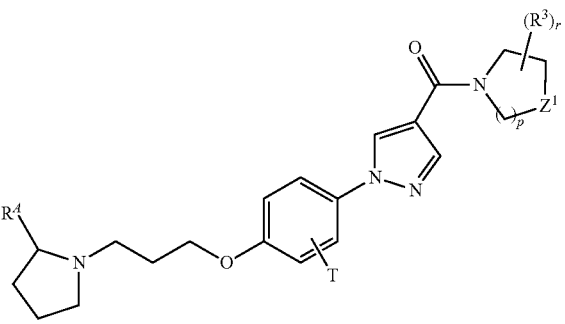

{wherein $Z^1$ represents —CH₂— or —O—,
p represents an integer of 0 to 3,
r represents an integer of 0 to 2,
T represents a hydrogen atom or halogen,
R³ represents halogen, $C_1$-$C_6$ alkyl, $C_1$-$C_6$ alkoxy, hydroxy or oxo (provided that when $Z^1$ is —CH₂—, the hydrogen atom(s) may be replaced by R³), and
$R^A$ represents $C_1$-$C_6$ alkyl}.

A preferred embodiment for the above formula is as follows: $Z^1$ is preferably —O—, $R^A$ is preferably methyl, R³ is preferably $C_1$-$C_6$ alkyl or hydroxy, and r is preferably 0.

As used herein, the term "pharmaceutically acceptable salt" is intended to include a salt with an inorganic acid such as sulfuric acid, hydrochloric acid, hydrobromic acid, phosphoric acid or nitric acid; a salt with an organic acid such as acetic acid, oxalic acid, lactic acid, tartaric acid, fumaric acid, maleic acid, citric acid, benzenesulfonic acid, methanesulfonic acid, p-toluenesulfonic acid, benzoic acid, camphorsulfonic acid, ethanesulfonic acid, glucoheptonic acid, gluconic acid, glutamic acid, glycolic acid, malic acid, malonic acid, mandelic acid, galactaric acid or naphthalene-2-sulfonic acid; a salt with one or more metal ions such as lithium ion, sodium ion, potassium ion, calcium ion, magnesium ion, zinc ion and/or aluminum ion; as well as a salt with ammonia or an amine such as arginine, lysine, piperazine, choline, diethylamine, 4-phenylcyclohexylamine, 2-aminoethanol or benzathine.

The compounds of the present invention may be present in the form of various solvates. They may also be in hydrate form in terms of applicability as pharmaceutical preparations.

The compounds of the present invention encompass all of the following: enantiomers, diastereomers, equilibrium compounds, mixtures thereof at any ratio, racemates, etc.

The compounds of the present invention also encompass compounds in which one or more hydrogen atoms, carbon atoms, nitrogen atoms, oxygen atoms or sulfur atoms are replaced by their radioisotopes or stable isotopes. These labeled compounds are useful for metabolism and/or pharmacokinetics study, biological analysis as receptor ligands, or other purposes.

The compounds of the present invention may be formulated into pharmaceutical preparations in combination with one or more pharmaceutically acceptable carriers, excipients or diluents. Examples of such carriers, excipients and diluents include water, lactose, dextrose, fructose, sucrose, sorbitol, mannitol, polyethylene glycol, propylene glycol, starch, gum, gelatin, alginate, calcium silicate, calcium phosphate, cellulose, water syrup, methylcellulose, polyvinylpyrrolidone, alkyl parahydroxy benzosorbate, talc, magnesium stearate, stearic acid, glycerine, as well as various oils such as sesame oil, olive oil, soybean oil, and the like.

Moreover, the above carriers, excipients or diluents may optionally be blended with commonly used additives such as extenders, binders, disintegrating agents, pH adjustors, solubilizers and so on, and then formulated using standard techniques into oral or parenteral dosage forms including tablets, pills, capsules, granules, powders, solutions, emulsions, suspensions, ointments, injections, skin plasters, etc. The compounds of the present invention may be given to adult patients at 0.001 to 500 mg per administration, once or several times a day, by the oral or parenteral route. This dosage may be increased or decreased as appropriate for the type of disease to be treated, the age, body weight and symptom of a patient, etc.

Profiles desired for the compounds of the present invention include excellent efficacy, good in vivo kinetics (good oral absorption, no tissue-specific accumulation), excellent physical properties, low toxicity, etc.

The compounds of the present invention can be prepared in the following manner.

(Process for Preparing the Compounds of the Present Invention)

The compounds of the present invention can be prepared by known organic chemistry procedures, for example, according to the following reaction schemes. In Reaction Schemes 1 to 10 shown below, R, $R^1$ to $R^{10}$, T, G, $Z^1$, $Z^2$, p, q, r, s and n are as defined above. $X^1$ to $X^3$, which may be the same or different, each represent a leaving group such as a halogen atom (e.g., a chlorine atom, a bromine atom, an iodine atom) or an organic sulfonyloxy group (e.g., a methanesulfonyloxy group, a benzenesulfonyloxy group, a p-toluenesulfonyloxy group, a trifluoromethanesulfonyloxy group), $Y^1$ to $Y^4$, which may be the same or different, each represent a leaving group (e.g., a halogen atom or an organic sulfonyloxy group) or a hydroxyl group, $Z^3$ represents a carbon atom or an oxygen atom, and t represents an integer of 0 or 1.

Explanation will be given below of the process shown in Reaction Scheme 1 for preparing the compound of the present invention. This process is intended to prepare the compound (1) of the present invention from compound (2).

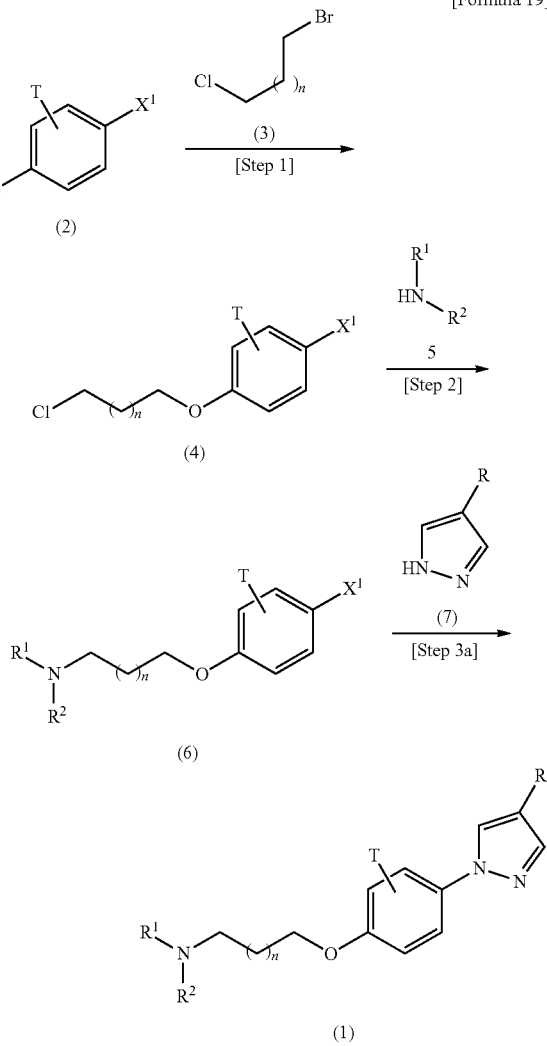

(Step 1)

Step 1 is intended to obtain compound (4) by coupling reaction between compound (2) and known compound (3). Compound (2) is known or may be easily synthesized from a known compound. This coupling reaction may be accomplished by standard procedures for reaction between phenol and alkyl halide in the presence of a base with or without a solvent. If necessary, for example, an additive such as potassium iodide or sodium bromide may be added. Examples of a base available for use in this reaction include pyridine, triethylamine, diisopropylethylamine, potassium tert-butoxide, potassium carbonate, cesium carbonate, sodium bicarbonate, sodium hydroxide, potassium hydroxide, and sodium hydride. Examples of a solvent available for use in this reaction include alcohols (e.g., methanol, ethanol, isopropanol); ethers (e.g., tetrahydrofuran, 1,4-dioxane); hydrocarbons (e.g., toluene, benzene); halogenated hydrocarbons (e.g., chloroform, dichloromethane); amides (e.g., N,N-dimethylformamide, N,N-dimethylacetamide, N-methyl-2-pyrrolidone); ketones (e.g., acetone, 2-butanone); dimethyl sulfoxide; acetonitrile; water; or mixed solvents thereof. Among them, preferred are tetrahydrofuran, N,N-dimethylformamide, acetonitrile, and 2-butanone. The reaction temperature in this reaction generally ranges from 0° C. to 150° C., preferably from 15° C. to 100° C., and the reaction time generally ranges from 1 to 48 hours, preferably from 1 to 12 hours.

(Step 2)

Step 2 is intended to obtain compound (6) by condensation between compounds (4) and (5) through coupling reaction. Compound (5) is known or may be easily synthesized from a known compound. This coupling reaction may be accomplished by standard procedures for reaction between amine and alkyl halide in the presence or absence of a base with or without a solvent. If necessary, for example, an additive such as potassium iodide or sodium bromide may be added. Examples of a base available for use in this reaction include pyridine, triethylamine, diisopropylethylamine, potassium tert-butoxide, potassium carbonate, cesium carbonate, sodium bicarbonate, sodium hydroxide, potassium hydroxide, and sodium hydride. Examples of a solvent available for use in this reaction include alcohols (e.g., methanol, ethanol, isopropanol); ethers (e.g., tetrahydrofuran, 1,4-dioxane); hydrocarbons (e.g., toluene, benzene); halogenated hydrocarbons (e.g., chloroform, dichloromethane); amides (e.g., N,N-dimethylformamide, N,N-dimethylacetamide, N-methyl-2-pyrrolidone); ketones (e.g., acetone, 2-butanone); dimethyl sulfoxide; acetonitrile; water; or mixed solvents thereof. Among them, preferred are tetrahydrofuran, N,N-dimethylformamide, and acetonitrile. The reaction temperature in this reaction generally ranges from 0° C. to 150° C., preferably from 15° C. to 100° C., and the reaction time generally ranges from 1 to 48 hours, preferably from 1 to 12 hours.

(Step 3a)

Step 3a is intended to obtain the compound (1) of the present invention by condensation between compounds (6) and (7) through coupling reaction. Compound (7) is known or may be easily synthesized from a known compound. This coupling reaction may be accomplished by standard procedures for aromatization of a nitrogen atom in an azole compound in the presence of a base using a ligand and a catalyst in a solvent, for example, according to the method described in Kunz et al., Synlett, 2003, vol. 15, pp. 2428-2439 or equivalent methods thereof. Examples of a catalyst available for use in this reaction include copper catalysts commonly used for condensation reaction, as exemplified by copper(0), copper (I) iodide, copper(I) chloride, copper(I) oxide, copper(I) bromide tristriphenylphosphine complex, and copper(I) trifluoromethanesulfonante benzene complex. Examples of a ligand available for use in this reaction include those commonly used for condensation reaction in the presence of a copper catalyst, as exemplified by N,N'-dimethylethylenediamine, N,N'-dimethylcyclohexane-1,2-diamine, 2-aminopyridine, 1,10-phenanthroline, 2-hydroxybenzaldehyde oxime, and ethylene glycol. Examples of a base available for use in this reaction include potassium carbonate, potassium phosphate, potassium hydroxide, potassium tert-butoxide, cesium carbonate, sodium carbonate, sodium bicarbonate, sodium acetate, sodium methoxide, and tetrabutylammonium hydroxide. Among them, preferred are potassium carbonate and cesium carbonate. Examples of a solvent available for use in this reaction include alcohols (e.g., methanol, ethanol, isopropanol); ethers (e.g., tetrahydrofuran, 1,4-dioxane); hydrocarbons (e.g., toluene, benzene); halogenated hydrocarbons (e.g., chloroform, dichloromethane); amides (e.g., N,N-dimethylformamide, N,N-dimethylacetamide, N-methyl-2-pyrrolidone); ketones (e.g., acetone, 2-butanone); dimethyl sulfoxide; acetonitrile; water; or mixed solvents thereof. Among them, preferred are toluene, N,N-dimethylformamide, and N-methyl-2-pyrrolidone. The reaction temperature in this reaction generally ranges from 0° C. to 150° C., preferably from 40° C. to 120° C., and the reaction time generally ranges from 1 to 48 hours, preferably from 1 to 12 hours.

(Reaction Scheme 2)

[Formula 20]

(Step 4)

Alternatively, compound (6) can also be obtained by coupling reaction between compounds (2) and (8). Compound (8) is known or may be easily synthesized from a known compound. This coupling reaction may be accomplished in the same manner as shown in Step 1 when $Y^1$ is a leaving group such as a halogen atom.

When $Y^1$ is a hydroxyl group, this coupling reaction may be Mitsunobu reaction, for example, which is accomplished in a solvent in the presence of a reagent composed of an organophosphorus compound (e.g., triphenylphosphine, tributylphosphine) in combination with an azo compound (e.g., diethyl azodicarboxylate, diisopropyl azodicarboxylate, di-tert-butyl azodicarboxylate) or in the presence of a phosphorus ylide reagent (e.g., cyanomethyltributylphosphorane). Examples of a solvent available for use in this reaction include ethers (e.g., tetrahydrofuran, 1,4-dioxane); hydrocarbons (e.g., toluene, benzene); halogenated hydrocarbons (e.g., chloroform, dichloromethane); amides (e.g., N,N-dimethylformamide, N,N-dimethylacetamide, N-methyl-2-pyrrolidone); dimethyl sulfoxide; acetonitrile; or mixed solvents thereof. Among them, preferred are tetrahydrofuran and toluene. The reaction temperature in this reaction generally ranges from 0° C. to 120° C., preferably from 15° C. to 80° C., and the reaction time generally ranges from 1 to 48 hours, preferably from 1 to 12 hours.

Explanation will be given below of the process shown in Reaction Scheme 3 for preparing the compound of the present invention. This process is intended to prepare the compound (1-2) or (1-3) of the present invention from compound (1-1).

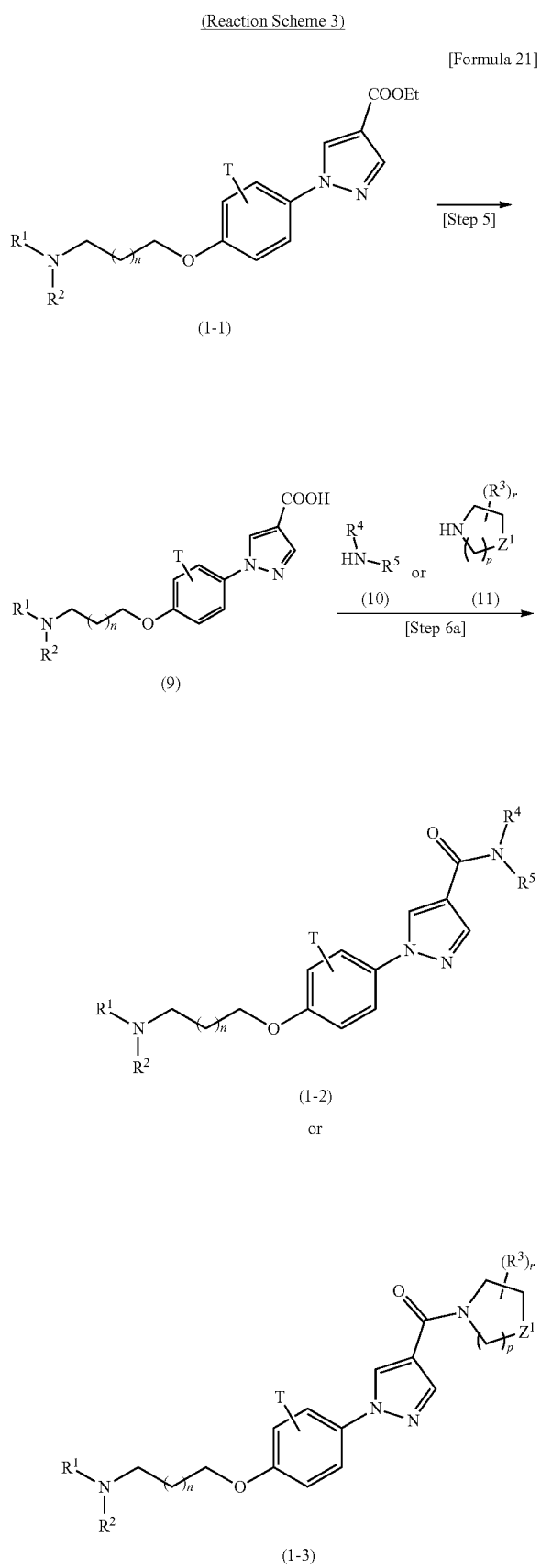

(Reaction Scheme 3)

(Step 5)

Step 5 is intended to obtain compound (9) by hydrolysis of the ethoxycarbonyl group in compound (1-1) into a carboxylic acid form. This hydrolysis reaction may be accomplished by standard reaction for ester hydrolysis, for example, in the presence of a strong acid with or without a solvent, or alternatively, in the presence of a base in a solvent, according to the method described in T. W. Greene and P. G. M. Wuts ed., Protective Groups in Organic Synthesis, third edition, John Wiley and Sons or equivalent methods thereof. The reaction temperature in this reaction generally ranges from 0° C. to 120° C., preferably from 15° C. to 80° C., and the reaction time generally ranges from 1 to 48 hours, preferably from 1 to 12 hours.

(Step 6a)

Step 6a is intended to obtain the compound (1-2) or (1-3) of the present invention by condensation between compound (9) and compound (10) or (11), respectively, through coupling reaction. Compounds (10) and (11) are known or may be easily synthesized from known compounds. This coupling reaction may be accomplished by standard procedures for amidation of a carboxylic acid, for example, through conversion of a carboxylic acid into a carboxylic acid halide (e.g., carboxylic acid chloride, carboxylic acid bromide) and the subsequent reaction with an amine, through reaction of a mixed acid anhydride (e.g., obtained from a carboxylic acid and a chlorocarbonate ester) with an amine, through conversion of a carboxylic acid into an active ester (e.g., 1-benzotriazolyl ester, succinimidyl ester) and the subsequent reaction with an amine, or through reaction of a carboxylic acid with an amine in the presence of a dehydration condensing agent. All of these reactions may be accomplished in the presence or absence of a base in a solvent. Examples of a dehydration condensing agent available for use in this reaction include 3-(3-dimethylaminopropyl)-1-ethylcarbodiimide hydrochloride, dicyclohexylcarbodiimide, diphenylphosphorylazide, and carbonyldiimidazole. If necessary, it is possible to use an activator such as 1-hydroxybenzotriazole or hydroxysuccinimide. Examples of a base available for use in this reaction include pyridine, triethylamine, diisopropylethylamine, potassium carbonate, sodium carbonate, and sodium bicarbonate. Examples of a solvent available for use in this reaction include ethers (e.g., tetrahydrofuran, 1,4-dioxane); hydrocarbons (e.g., toluene, benzene); halogenated hydrocarbons (e.g., chloroform, dichloromethane); amides (e.g., N,N-dimethylformamide, N,N-dimethylacetamide, N-methyl-2-pyrrolidone); ketones (e.g., acetone, 2-butanone); dimethyl sulfoxide; acetonitrile; water; or mixed solvents thereof. Among them, preferred is toluene, tetrahydrofuran or N,N-dimethylformamide. The reaction temperature in this reaction generally ranges from 0° C. to 120° C., preferably from 15° C. to 40° C., and the reaction time generally ranges from 1 to 48 hours, preferably from 1 to 12 hours.

(Reaction Scheme 4)

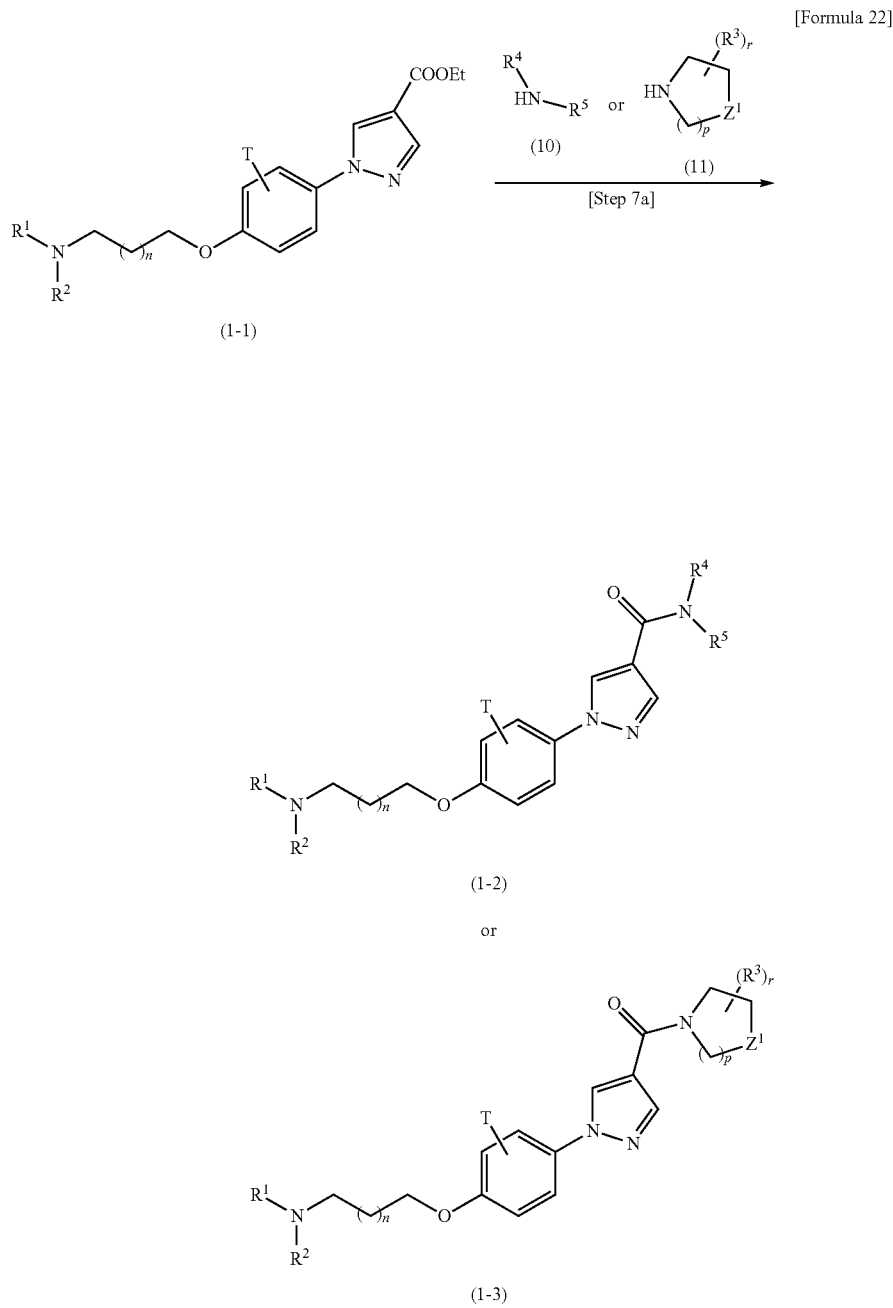

(Step 7a)

Alternatively, the compound (1-2) or (1-3) of the present invention can also be obtained by coupling reaction between compound (1-1) and compound (10) or (11), respectively. This coupling reaction may be accomplished by standard ester-amide exchange reaction for a carboxylic acid ester, for example, through reaction of a carboxylic acid ester with a primary or secondary amine with or without a solvent. If necessary, for example, an additive such as sodium methoxide, sodium hydride, n-butyllithium or trimethylaluminum may be added. In the case of using a solvent in this reaction, examples of a solvent include alcohols (e.g., methanol, ethanol, isopropanol); ethers (e.g., tetrahydrofuran, 1,4-dioxane); hydrocarbons (e.g., toluene, benzene, xylene); amides (e.g., N,N-dimethylformamide, N,N-dimethylacetamide, N-methyl-2-pyrrolidone); ketones (e.g., acetone, 2-butanone); dimethyl sulfoxide; acetonitrile; water; or mixed solvents thereof. Among them, preferred are toluene, tetrahydrofuran, and dimethyl sulfoxide. The reaction temperature in this reaction generally ranges from 15° C. to 150° C., preferably from 15° C. to 100° C., and the reaction time generally ranges from 1 to 48 hours, preferably from 1 to 12 hours.

Explanation will be given below of the process shown in Reaction Scheme 5 for preparing the compound of the present invention. This process is intended to prepare the compound (1-4) or (1-5) of the present invention from compound (9).

(Reaction Scheme 5)

[Formula 23]

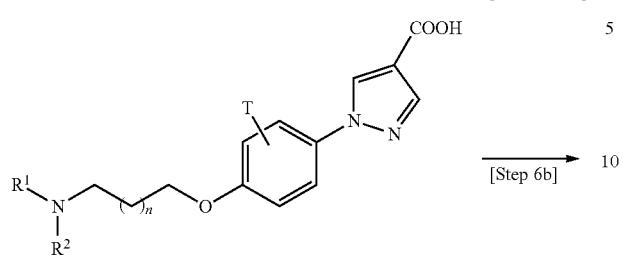

(9)

[Step 6b]

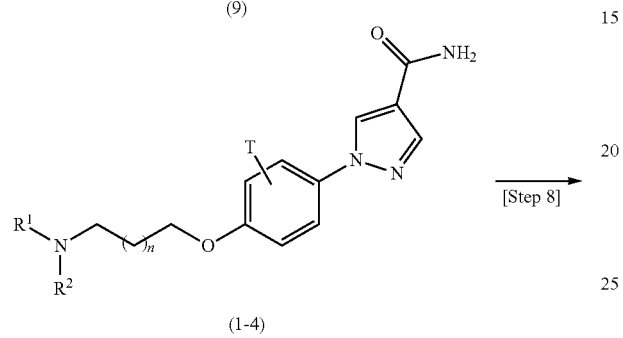

(1-4)

[Step 8]

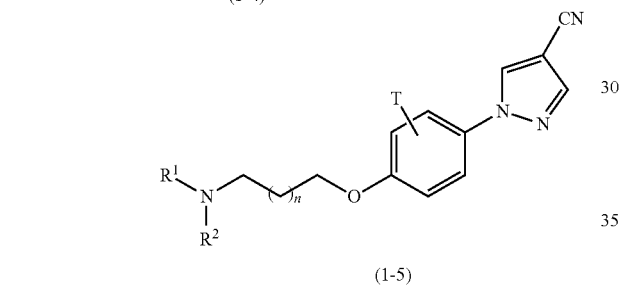

(1-5)

(Reaction Scheme 6)

[Formula 24]

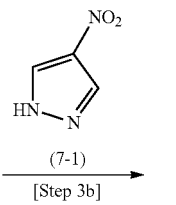

(7-1)

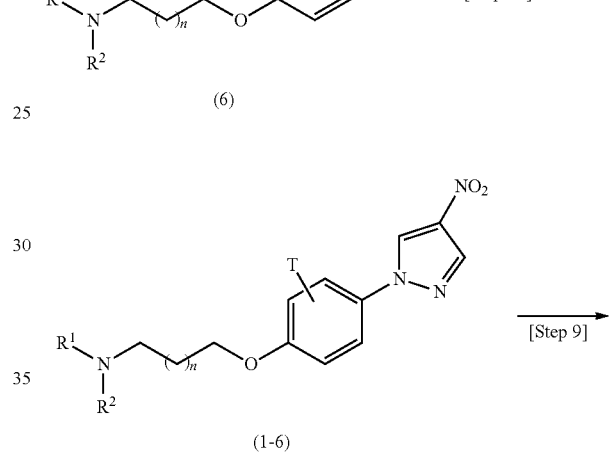

[Step 3b]

(6)

[Step 9]

(1-6)

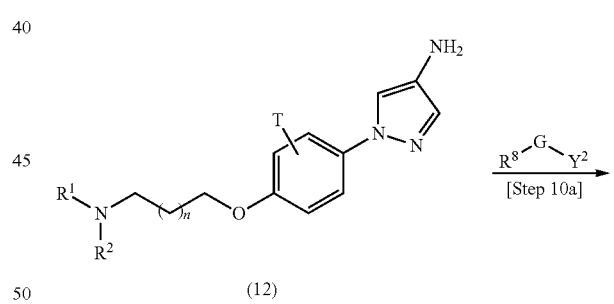

(12)

$R^8\text{—}G\text{—}Y^2$

[Step 10a]

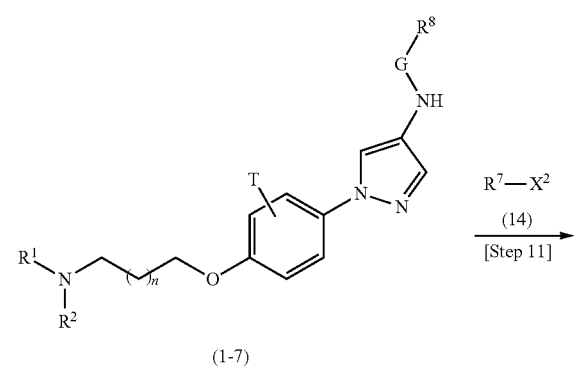

(1-7)

$R^7\text{—}X^2$ (14)

[Step 11]

(Step 6b)

Step 6b is intended to obtain the compound (1-4) of the present invention by reaction between compound (9) and ammonia. This reaction may be accomplished in the same manner as shown in Step 6a. More specifically, for example, it may be accomplished by reaction of a carboxylic acid with aqueous ammonia in the presence of a dehydration condensing agent.

(Step 8)

Step 8 is intended to obtain the compound (1-5) of the present invention by conversion of the carbamoyl group in compound (1-4) into a nitrile group. This step may be accomplished by standard reaction for converting a carbamoyl group into a nitrile group, for example, in the presence of a dehydrating agent with or without a solvent. If necessary, for example, an additive such as N,N-dimethylformamide or sodium chloride may be added. Examples of a dehydrating agent available for use in this reaction include phosphorus pentaoxide, phosphorus pentachloride, phosphorus trichloride, phosphoryl chloride, thionyl chloride, oxalyl chloride, trifluoroacetic anhydride, and trifluoromethanesulfonic anhydride. In the case of using a solvent in this reaction, examples of a solvent include ethers (e.g., tetrahydrofuran, 1,4-dioxane); hydrocarbons (e.g., toluene, benzene); amides (e.g., N,N-dimethylformamide, N,N-dimethylacetamide, N-methyl-2-pyrrolidone); acetonitrile; or mixed solvents thereof. The reaction temperature in this reaction generally ranges from 0° C. to 120° C., preferably from 15° C. to 80° C., and the reaction time generally ranges from 1 to 48 hours, preferably from 1 to 12 hours.

Explanation will be given below of the process shown in Reaction Scheme 6 for preparing the compound of the present invention. This process is intended to prepare the compound (1-6), (1-7) or (1-8) of the present invention from compound (6).

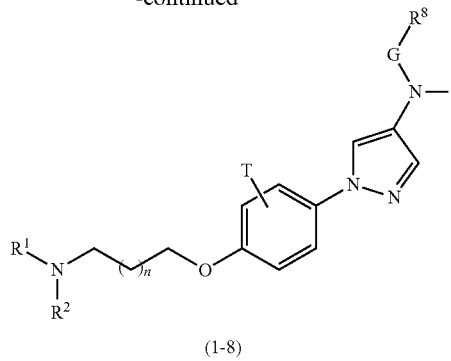

(1-8)

(Step 3b)
Step 3b is intended to obtain the compound (1-6) of the present invention by condensation between compounds (6) and (7-1) through coupling reaction. This reaction may be accomplished in the same manner as shown in Step 3a.

(Step 9)
Step 9 is intended to obtain compound (12) by reduction of the nitro group in compound (1-6). This step may be accomplished by standard reduction reaction for converting a nitro group into an amino group, for example, through catalytic reduction by hydrogenation in the presence of a catalyst (e.g., palladium on carbon, platinum, Raney Nickel, rhodium-alumina), through reduction under acidic conditions using zinc, iron, tin or tin(II) chloride, or through reduction using a metal hydride (e.g., lithium aluminum hydride). More specifically, for example, this step may be performed with the use of palladium on carbon as a catalyst in catalytic reduction by hydrogenation in a methanol solvent.

(Step 10a)
Step 10a is intended to obtain the compound (1-7) of the present invention by condensation between compounds (12) and (13) through coupling reaction. Compound (13) is known or may be easily synthesized from a known compound. This coupling reaction may be accomplished in the same manner as shown in Step 6a when G is CO and $Y^2$ is a hydroxyl group.

When $Y^2$ is a halogen atom, this coupling reaction may be accomplished by reacting compound (12) with compound (13) in the presence or absence of a base with or without a solvent. Examples of a base available for use in this reaction include pyridine, triethylamine, diisopropylethylamine, potassium carbonate, sodium bicarbonate, and sodium hydroxide. Examples of a solvent available for use in this reaction include ethers (e.g., tetrahydrofuran, 1,4-dioxane); hydrocarbons (e.g., toluene, benzene); halogenated hydrocarbons (e.g., chloroform, dichloromethane); amides (e.g., N,N-dimethylformamide, N,N-dimethylacetamide, N-methyl-2-pyrrolidone); or mixed solvents thereof. Among them, preferred are tetrahydrofuran and toluene. The reaction temperature in this reaction generally ranges from 0° C. to 120° C., preferably from 15° C. to 80° C., and the reaction time generally ranges from 1 to 48 hours, preferably from 1 to 12 hours.

(Step 11)
Step 11 is intended to obtain the compound (1-8) of the present invention by reaction between compounds (1-7) and (14). Compound (14) is known or may be easily synthesized from a known compound. This reaction may be accomplished by standard procedures for alkylation of an amide or sulfonamide, for example, by reacting compound (1-7) with compound (14) in the presence of a base in a solvent. If necessary, for example, an additive such as tetrabutylammonium bromide or 18-crown-6-ether may be added. Examples of a base available for use in this reaction include sodium hydride, potassium hydride, potassium tert-butoxide, potassium hydroxide, sodium hydroxide, sodium methoxide, and n-butyllithium. Examples of a solvent available for use in this reaction include alcohols (e.g., methanol, ethanol, isopropanol); ethers (e.g., tetrahydrofuran, 1,4-dioxane); hydrocarbons (e.g., toluene, benzene); amides (e.g., N,N-dimethylformamide, N,N-dimethylacetamide, N-methyl-2-pyrrolidone); dimethyl sulfoxide; acetonitrile; water; or mixed solvents thereof. Among them, preferred are tetrahydrofuran and N,N-dimethylformamide. The reaction temperature in this reaction generally ranges from 0° C. to 150° C., preferably from 15° C. to 100° C., and the reaction time generally ranges from 1 to 48 hours, preferably from 1 to 12 hours.

Explanation will be given below of the process shown in Reaction Scheme 7 for preparing the compound of the present invention. This process is intended to prepare the compound (1-8) of the present invention from compound (12).

(Reaction Scheme 7)

[Formula 25]

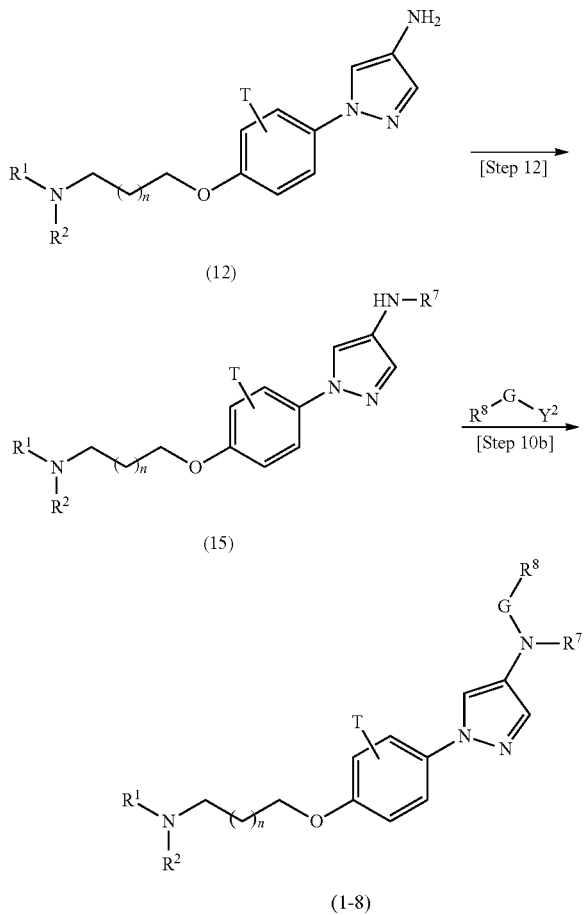

(Step 12)
Step 12 is intended to obtain compound (15) by alkylation of the primary amino group in compound (12). This alkylation reaction may be accomplished by standard alkylation for converting a primary amino group into a secondary amino group, for example, through reaction in the presence of a base using an alkylating agent (e.g., alkyl halide, alkyl methanesulfonate), through reductive amination with an aldehyde, through conversion into an acid amide with a carboxylic acid or a derivative thereof and the subsequent reduction with a metal hydride (e.g., borane), or through dehydration condensation with an alcohol.

(Step 10b)

Step 10b is intended to obtain the compound (1-8) of the present invention by condensation between compounds (15) and (13) through coupling reaction. This coupling reaction may be accomplished in the same manner as shown in Step 10a.

Explanation will be given below of the process shown in Reaction Scheme 8 for preparing the compound of the present invention. This process is intended to prepare the compound (1-9) or (1-10) of the present invention from compound (12).

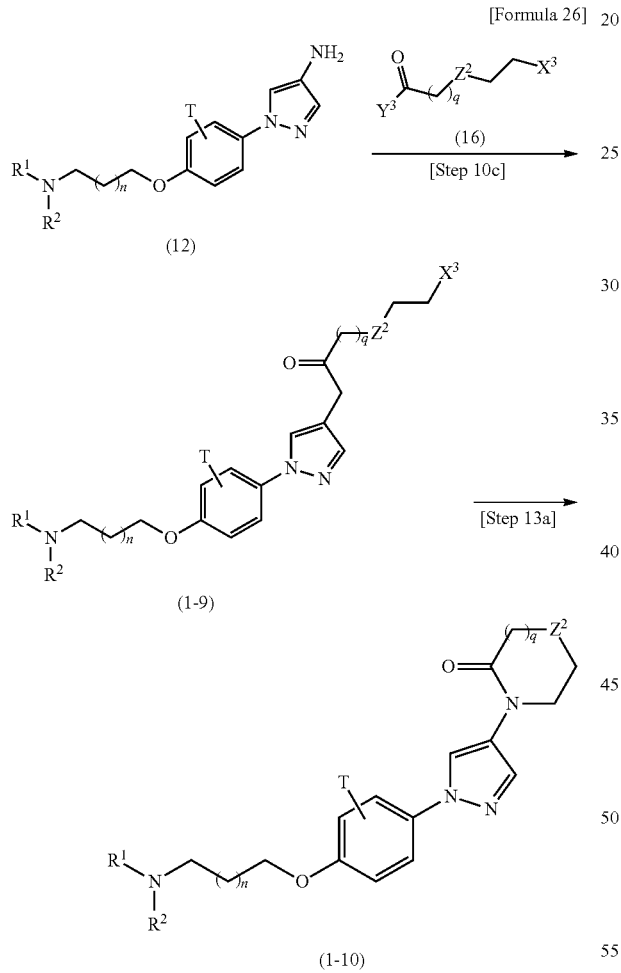

(Step 10c)

Step 10c is intended to obtain the compound (1-9) of the present invention by condensation between compounds (12) and (16) through coupling reaction. Compound (16) is known or may be easily synthesized from a known compound. This coupling reaction may be accomplished in the same manner as shown in Step 10a.

(Step 13a)

Step 13a is intended to obtain the compound (1-10) of the present invention by intramolecular cyclization of compound (1-9). This intramolecular cyclization reaction may be accomplished according to the method as described in, e.g., Journal of Medicinal Chemistry, 2002, vol. 45, pp. 3972-3983 or equivalent methods thereof. Examples of a base available for use in this reaction include sodium hydride, potassium hydride, potassium carbonate, potassium tert-butoxide, and sodium hydroxide. Examples of a solvent available for use in this reaction include ethers (e.g., tetrahydrofuran, 1,4-dioxane); hydrocarbons (e.g., toluene, benzene); amides (e.g., N,N-dimethylformamide, N,N-dimethylacetamide, N-methyl-2-pyrrolidone); ketones (e.g., acetone, 2-butanone); dimethyl sulfoxide; acetonitrile; or mixed solvents thereof. Among them, preferred are tetrahydrofuran and toluene. The reaction temperature in this reaction generally ranges from 0° C. to 150° C., preferably from 15° C. to 80° C., and the reaction time generally ranges from 1 to 48 hours, preferably from 1 to 12 hours.

Explanation will be given below of the process shown in Reaction Scheme 9 for preparing the compound of the present invention. This process is intended to prepare the compound (1-11) of the present invention from compound (12).

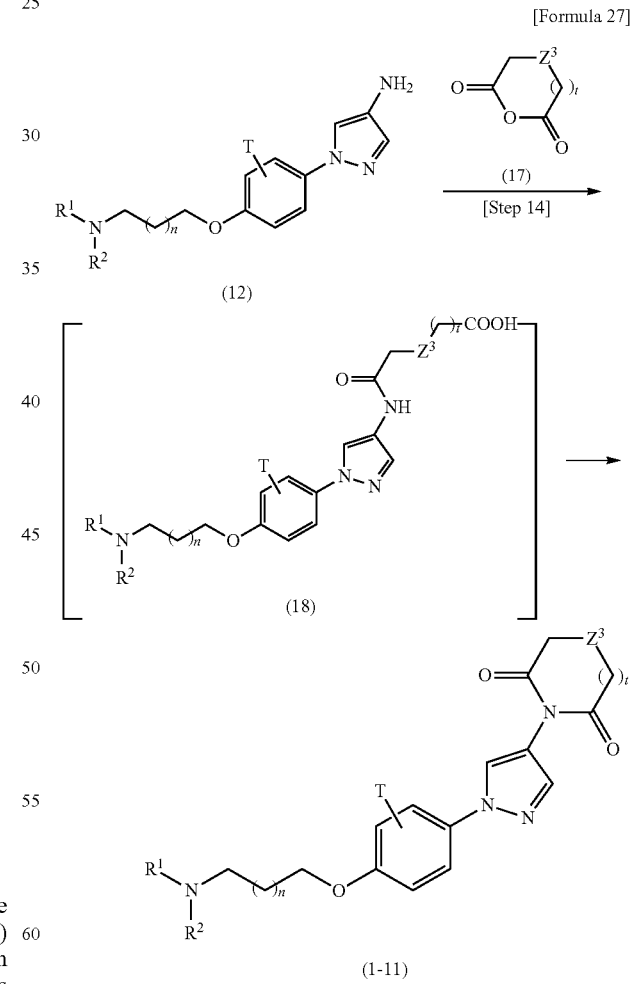

(Step 14)

Step 14 is intended to obtain the compound (1-11) of the present invention by condensation between compounds (12) and (17). Compound (17) is known or may be easily synthesized from a known compound. This condensation reaction may be accomplished by standard procedures for condensation between amine and acid anhydride, for example, by reacting compound (12) with compound (17) under heating conditions in the presence or absence of an acid with or without a solvent. Examples of an acid available for use in this reaction include sulfuric acid, and hydrochloric acid. Examples of a solvent available for use in this reaction include ethers (e.g., tetrahydrofuran, 1,4-dioxane); hydrocarbons (e.g., toluene, benzene); halogenated hydrocarbons (e.g., chloroform, dichloromethane); or mixed solvents thereof. Among them, preferred is toluene or tetrahydrofuran. The reaction temperature in this reaction generally ranges from 0° C. to 150° C., preferably from 40° C. to 120° C., and the reaction time generally ranges from 1 to 48 hours, preferably from 1 to 12 hours. Moreover, compound (18), which is a reaction intermediate in this step, may further be converted into compound (1-11) by intramolecular dehydration cyclization. This dehydration cyclization reaction may be accomplished by standard procedures for dehydration condensation, for example, by heating in the presence of acetic anhydride with or without a solvent.

Explanation will be given below of the process shown in Reaction Scheme 10 for preparing the compound of the present invention. This process is intended to prepare the compound (1-12) of the present invention from compound (12).

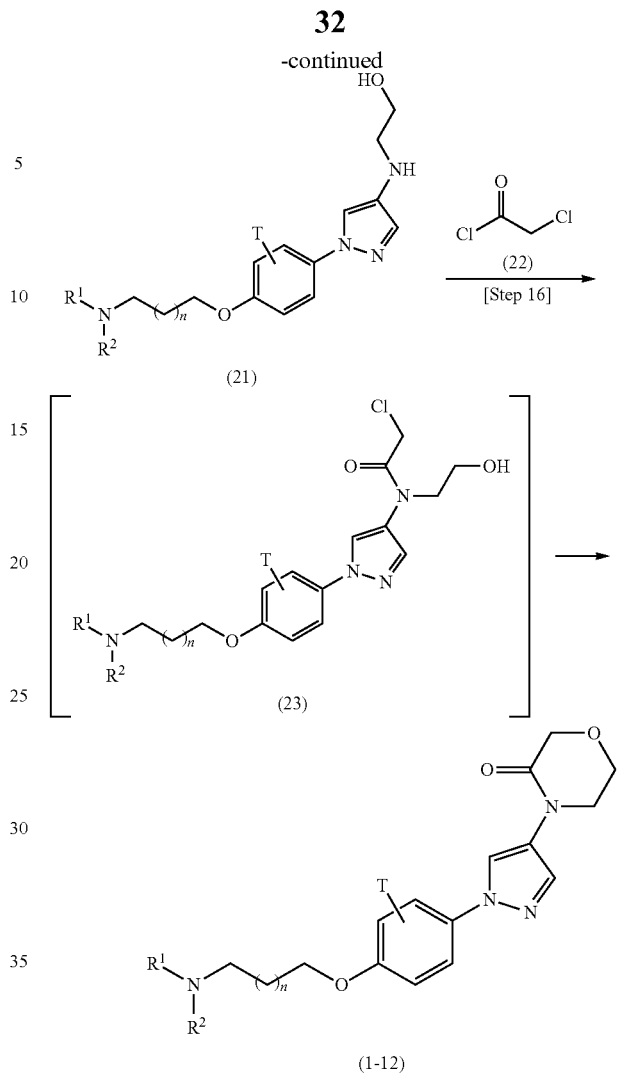

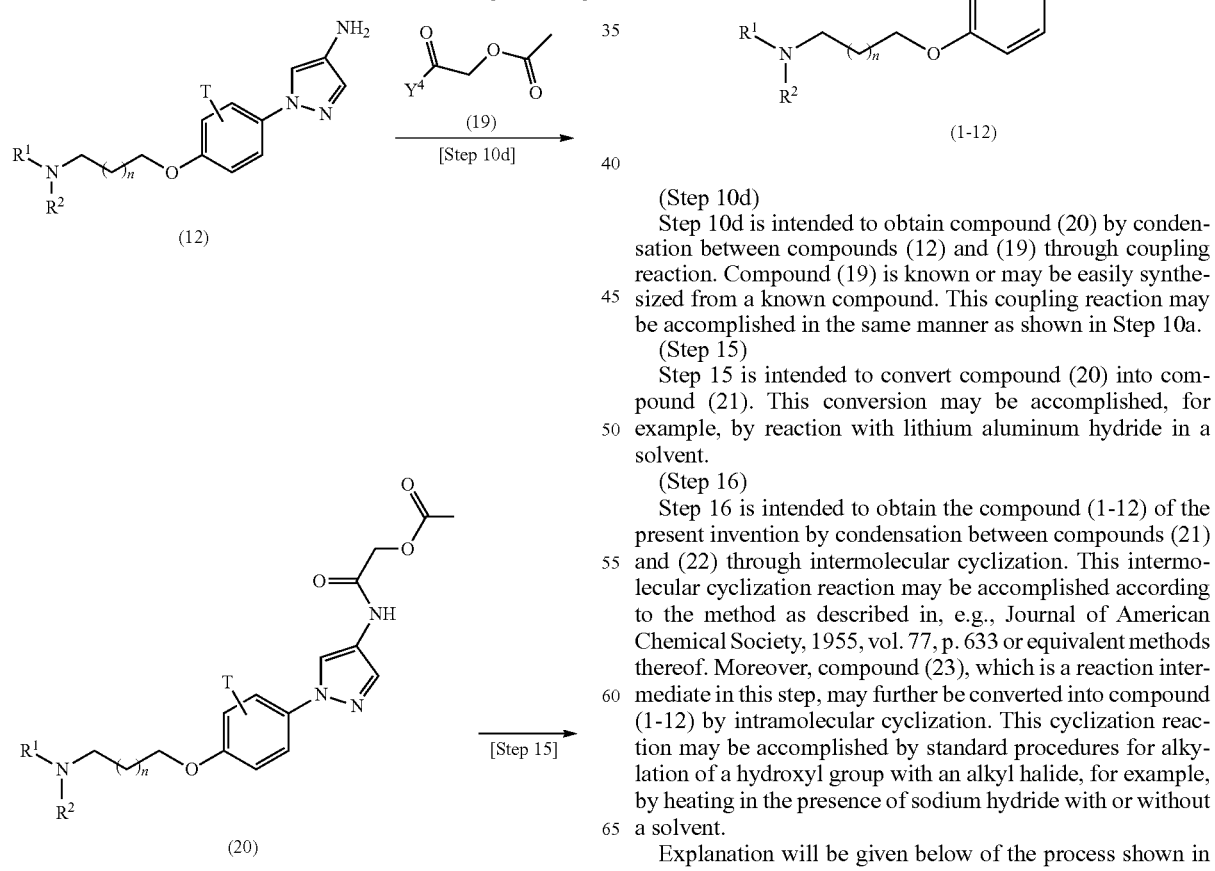

(Step 10d)

Step 10d is intended to obtain compound (20) by condensation between compounds (12) and (19) through coupling reaction. Compound (19) is known or may be easily synthesized from a known compound. This coupling reaction may be accomplished in the same manner as shown in Step 10a.

(Step 15)

Step 15 is intended to convert compound (20) into compound (21). This conversion may be accomplished, for example, by reaction with lithium aluminum hydride in a solvent.

(Step 16)

Step 16 is intended to obtain the compound (1-12) of the present invention by condensation between compounds (21) and (22) through intermolecular cyclization. This intermolecular cyclization reaction may be accomplished according to the method as described in, e.g., Journal of American Chemical Society, 1955, vol. 77, p. 633 or equivalent methods thereof. Moreover, compound (23), which is a reaction intermediate in this step, may further be converted into compound (1-12) by intramolecular cyclization. This cyclization reaction may be accomplished by standard procedures for alkylation of a hydroxyl group with an alkyl halide, for example, by heating in the presence of sodium hydride with or without a solvent.

Explanation will be given below of the process shown in Reaction Scheme 11 for preparing the compound of the present invention. This process is intended to prepare the compound (1-14) or (1-15) of the present invention from compound (1-13), i.e., the compound (1-2) of the present invention in which $R^4$ is a 2-hydroxyethyl group and $R^5$ is a tert-butoxycarbonylmethyl group.

(Reaction Scheme 11)

[Formula 29]

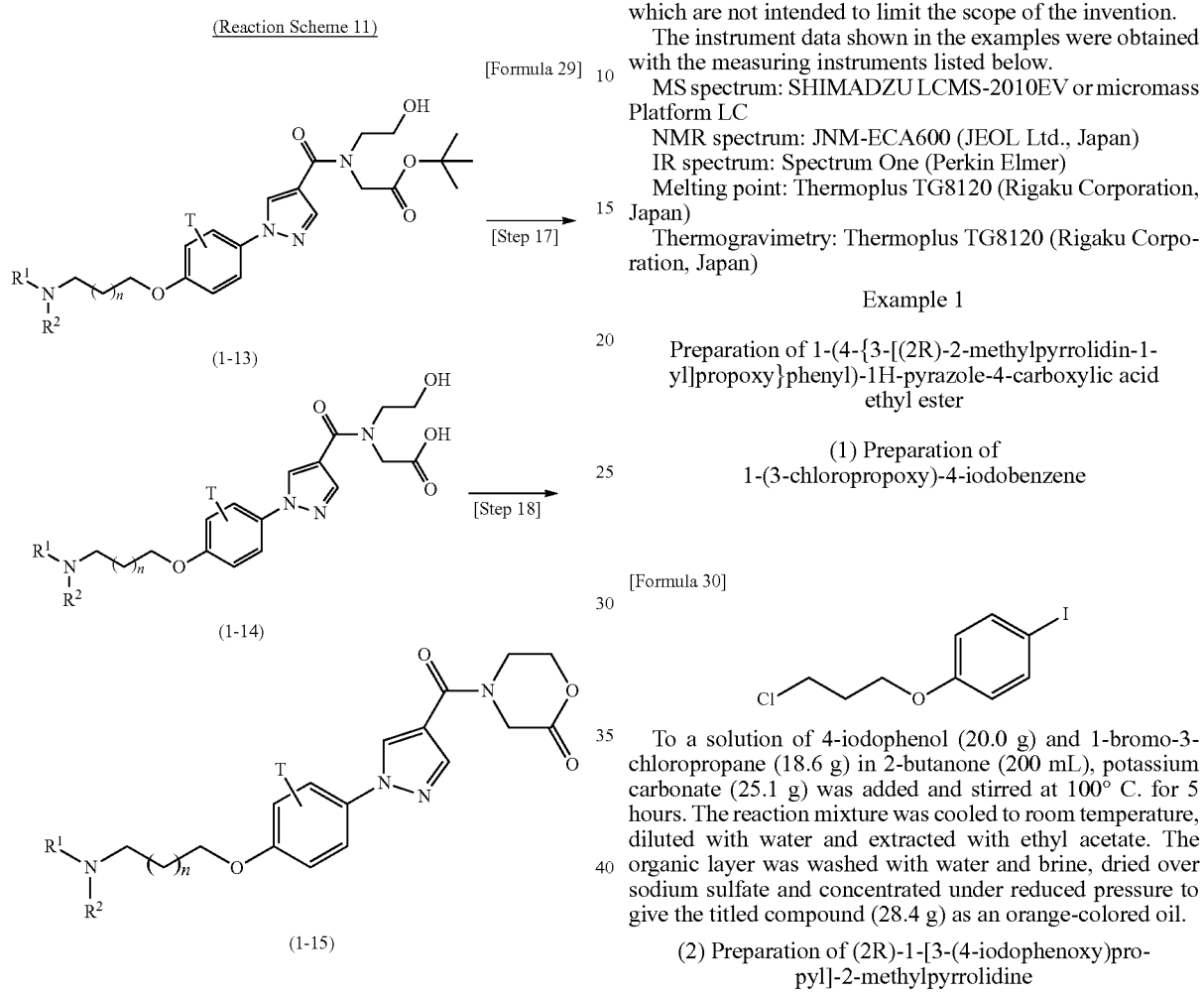

(Step 17)

Step 17 is intended to obtain the compound (1-14) of the present invention by hydrolysis of the tert-butoxycarbonyl group in compound (1-13) into a carboxylic acid form. This hydrolysis reaction may be accomplished by standard reaction for ester hydrolysis, for example, in the presence of a strong acid with or without a solvent, or alternatively, in the presence of a base in a solvent, according to the method described in T. W. Greene and P. G. M. Wuts ed., Protective Groups in Organic Synthesis, third edition, John Wiley and Sons or equivalent methods thereof. More specifically, for example, the hydrolysis reaction may be performed with trifluoroacetic acid in a solvent (e.g., chloroform) or with aqueous sodium hydroxide in a solvent (e.g., methanol). The reaction temperature in this reaction generally ranges from 0° C. to 120° C., preferably from 15° C. to 80° C., and the reaction time generally ranges from 1 to 48 hours, preferably from 1 to 12 hours.

(Step 18)

Step 18 is intended to obtain the compound (1-15) of the present invention by intramolecular cyclization of compound (1-14). This intramolecular cyclization reaction may be accomplished by standard procedures for converting a carboxylic acid into an ester, for example, through dehydration condensation between carboxylic acid and alcohol under acidic conditions or in the presence of a dehydrating agent with or without a solvent.

The present invention will be further described in more detail by way of the following examples and test examples, which are not intended to limit the scope of the invention.

The instrument data shown in the examples were obtained with the measuring instruments listed below.

MS spectrum: SHIMADZU LCMS-2010EV or micromass Platform LC

NMR spectrum: JNM-ECA600 (JEOL Ltd., Japan)

IR spectrum: Spectrum One (Perkin Elmer)

Melting point: Thermoplus TG8120 (Rigaku Corporation, Japan)

Thermogravimetry: Thermoplus TG8120 (Rigaku Corporation, Japan)

Example 1

Preparation of 1-(4-{3-[(2R)-2-methylpyrrolidin-1-yl]propoxy}phenyl)-1H-pyrazole-4-carboxylic acid ethyl ester (1) Preparation of 1-(3-chloropropoxy)-4-iodobenzene

[Formula 30]

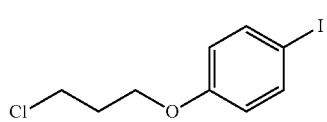

To a solution of 4-iodophenol (20.0 g) and 1-bromo-3-chloropropane (18.6 g) in 2-butanone (200 mL), potassium carbonate (25.1 g) was added and stirred at 100° C. for 5 hours. The reaction mixture was cooled to room temperature, diluted with water and extracted with ethyl acetate. The organic layer was washed with water and brine, dried over sodium sulfate and concentrated under reduced pressure to give the titled compound (28.4 g) as an orange-colored oil.

(2) Preparation of (2R)-1-[3-(4-iodophenoxy)propyl]-2-methylpyrrolidine

[Formula 31]

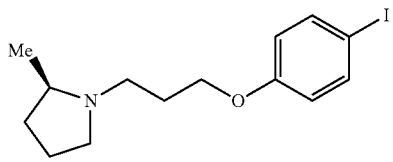

A suspension of 1-(3-chloropropoxy)-4-iodobenzene obtained in Example 1-(1) (2.79 g), (R)-2-methylpyrrolidine (0.961 g), sodium iodide (0.282 g) and potassium carbonate (2.60 g) in acetonitrile (2.8 mL) was stirred in a sealed tube at 100° C. for 5 hours. The reaction mixture was cooled to room temperature, diluted with water and extracted with ethyl acetate. The organic layer was washed with water and brine, dried over sodium sulfate and concentrated under reduced pressure. The resulting residue was purified by silica gel column chromatography (eluting solvent: n-hexane:ethyl acetate=10:1) to give the titled compound (3.27 g) as a yellow oil.

(3) Preparation of 1-(4-{3-[(2R)-2-methylpyrrolidin-1-yl]propoxy}phenyl)-1H-pyrazole-4-carboxylic acid ethyl ester

[Formula 32]

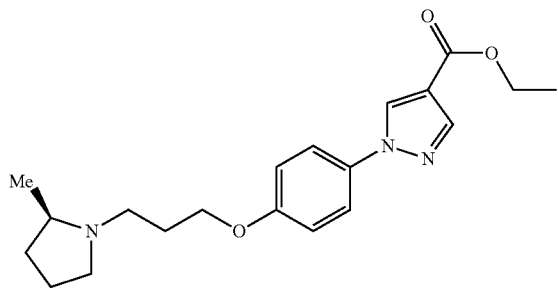

A suspension of (2R)-1-[3-(4-iodophenoxy)propyl]-2-methylpyrrolidine obtained in Example 1-(2) (1.60 g), 1H-pyrazole-4-carboxylic acid ethyl ester (0.779 g), (rac-trans-N,N'-dimethylcyclohexane-1,2-diamine (0.263 g), copper iodide (0.088 g) and cesium carbonate (3.02 g) in N,N-dimethylformamide (2.5 mL) was stirred at 120° C. for 4 hours. The reaction mixture was cooled to room temperature, diluted with water and extracted with ethyl acetate. The organic layer was concentrated under reduced pressure, and the resulting residue was purified by silica gel column chromatography (eluting solvent: n-hexane:ethyl acetate=3:1) to give the titled compound (1.11 g) as a yellow oil.

1H NMR (600 MHz, CHLOROFORM-d) δ ppm 1.09 (d, J=6.0 Hz, 3H), 1.37 (t, J=7.3 Hz, 3H), 1.39-1.45 (m, 1H), 1.65-1.73 (m, 1H), 1.74-1.82 (m, 1H), 1.89-2.06 (m, 3H), 2.12 (q, J=8.7 Hz, 1H), 2.18-2.23 (m, 1H), 2.26-2.34 (m, 1H), 2.95-3.02 (m, 1H), 3.18 (td, J=8.6, 2.5 Hz, 1H), 4.03-4.10 (m, 2H), 4.33 (q, J=7.3 Hz, 2H), 6.99 (d, J=9.2 Hz, 2H), 7.58 (d, J=9.2 Hz, 2H), 8.07 (s, 1H), 8.30 (s, 1H)

MS (ESI/APCI Dual) (Positive) m/z; 358 (M+H)$^+$

Example 2

Preparation of 1-(4-{3-[(2R)-2-methylpyrrolidin-1-yl]propoxy}phenyl)-1H-pyrazole-4-carboxamide (1) Preparation of 1-(4-{3-[(2R)-2-methylpyrrolidin-1-yl]propoxy}phenyl)-1H-pyrazole-4-carboxylic acid hydrochloride

[Formula 33]

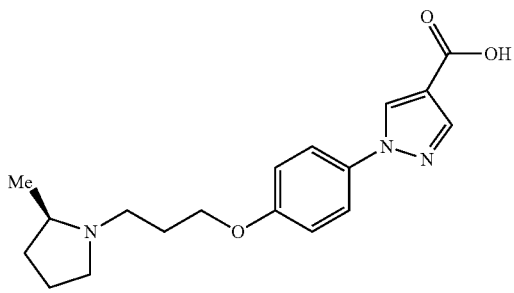

To 1-(4-{3-[(2R)-2-methylpyrrolidin-1-yl]propoxy}phenyl)-1H-pyrazole-4-carboxylic acid ethyl ester obtained in Example 1-(3) (1.11 g), concentrated hydrochloric acid (7.0 mL) was added at room temperature and stirred at 80° C. for 2 hours. The reaction mixture was concentrated under reduced pressure to give the titled compound (1.08 g) as a light-brown solid.

(2) Preparation of 1-(4-{3-[(2R)-2-methylpyrrolidin-1-yl]propoxy}phenyl)-1H-pyrazole-4-carboxamide

[Formula 34]

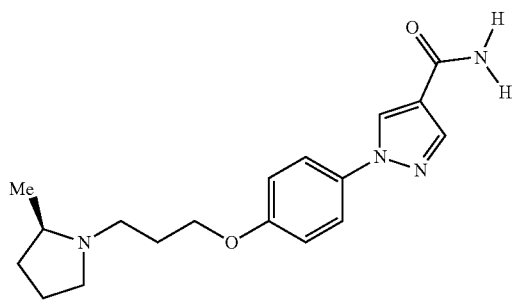

To a suspension of 1-(4-{3-[(2R)-2-methylpyrrolidin-1-yl]propoxy}phenyl)-1H-pyrazole-4-carboxylic acid hydrochloride obtained in Example 2-(1) (1.08 g) in N,N-dimethylformamide (11 mL), 1-hydroxybenzotriazole monohydrate (0.539 g) was added at room temperature and stirred for 5 minutes. To the reaction mixture, 1-ethyl-3-(3-dimethylaminopropyl)carbodiimide hydrochloride (0.679 g) was added and stirred at room temperature for 30 minutes, followed by addition of aqueous ammonia (25%, 0.702 g) and stirring overnight at room temperature. After addition of water and saturated aqueous sodium bicarbonate, the reaction mixture was extracted with ethyl acetate. The organic layer was washed with water and brine, dried over sodium sulfate and concentrated under reduced pressure. The resulting residue was purified by silica gel column chromatography (eluting solvent: chloroform:methanol=20:1) to give the titled compound (0.504 g) as a colorless solid.

1H NMR (600 MHz, CHLOROFORM-d) δ ppm 1.08 (d, J=6.0 Hz, 3H), 1.36-1.46 (m, 1H), 1.65-1.83 (m, 2H), 1.87-2.06 (m, 3H), 2.11 (q, J=9.0 Hz, 1H), 2.17-2.24 (m, 1H), 2.25-2.33 (m, 1H), 2.93-3.03 (m, 1H), 3.13-3.20 (m, 1H), 4.02-4.10 (m, 2H), 5.60 (br. s, 2H), 6.94-7.02 (m, 2H), 7.52-7.60 (m, 2H), 7.91 (s, 1H), 8.29 (s, 1H)

MS (ESI/APCI Dual) (Positive) m/z; 329 (M+H)$^+$

Example 3

Preparation of 1-(4-{3-[(2R)-2-methylpyrrolidin-1-yl]propoxy}phenyl)-1H-pyrazole-4-carbonitrile

[Formula 35]

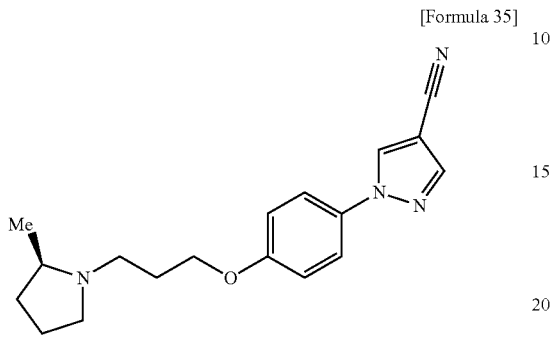

To a solution of 1-(4-{3-[(2R)-2-methylpyrrolidin-1-yl]propoxy}phenyl)-1H-pyrazole-4-carboxamide obtained in Example 2-(2) (0.466 g) in N,N-dimethylformamide (5.0 mL), thionyl chloride (1.0 mL) was added dropwise under ice cooling and stirred at 0° C. for 30 minutes. The reaction mixture was adjusted to pH 8 by addition of water and saturated aqueous sodium bicarbonate, and then extracted with ethyl acetate. The organic layer was washed with brine, dried over sodium sulfate and concentrated under reduced pressure. The resulting residue was purified by silica gel column chromatography (eluting solvent: n-hexane:ethyl acetate=1:1), and the resulting crystal was washed with hexane:diisopropyl ether (1:1) to give the titled compound (0.253 g) as a colorless solid.

1H NMR (600 MHz, CHLOROFORM-d) δ ppm 1.08 (d, J=6.0 Hz, 3H), 1.37-1.46 (m, 1H), 1.65-1.83 (m, 2H), 1.88-2.06 (m, 3H), 2.11 (q, J=8.7 Hz, 1H), 2.16-2.24 (m, 1H), 2.25-2.34 (m, 1H), 2.93-3.03 (m, 1H), 3.12-3.23 (m, 1H), 4.02-4.11 (m, 2H), 6.95-7.02 (m, 2H), 7.50-7.57 (m, 2H), 7.95 (s, 1H), 8.18 (s, 1H)

MS (ESI/APCI Dual) (Positive) m/z; 311 (M+H)+

Example 4

Preparation of 1-(4-{3-[(2S)-2-methylpyrrolidin-1-yl]propoxy}phenyl)-1H-pyrazole-4-carboxamide (1) Preparation of (2S)-1-[3-(4-iodophenoxy)propyl]-2-methylpyrrolidine

[Formula 36]

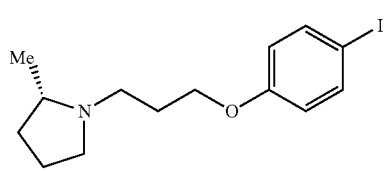

The same procedure as shown in Example 1-(2) was repeated to give the titled compound, except that (R)-2-methylpyrrolidine was replaced by (S)-2-methylpyrrolidine.

(2) Preparation of 1-(4-{3-[(2S)-2-methylpyrrolidin-1-yl]propoxy}phenyl)-1H-pyrazole-4-carboxylic acid hydrochloride

[Formula 37]

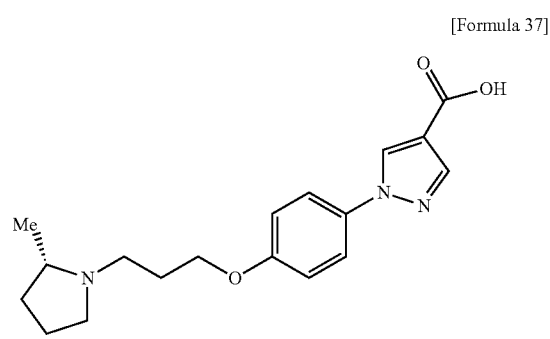

The same procedures as shown in Example 1-(3) and Example 2-(1) were repeated to give the titled compound, except that (2R)-1-[3-(4-iodophenoxy)propyl]-2-methylpyrrolidine was replaced by (2S)-1-[3-(4-iodophenoxy)propyl]-2-methylpyrrolidine obtained in Example 4-(1).

(3) Preparation of 1-(4-{3-[(2S)-2-methylpyrrolidin-1-yl]propoxy}phenyl)-1H-pyrazole-4-carboxamide

[Formula 38]

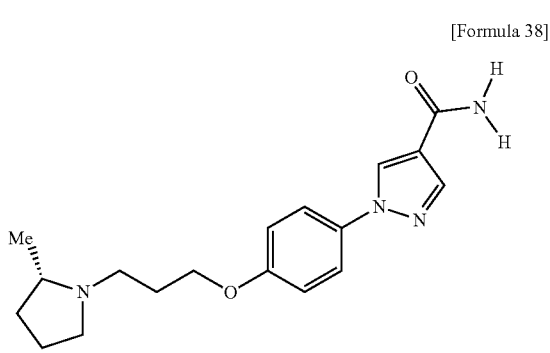

The same procedure as shown in Example 2-(2) was repeated to give the titled compound, except that 1-(4-{3-[(2R)-2-methylpyrrolidin-1-yl]propoxy}phenyl)-1H-pyrazole-4-carboxylic acid hydrochloride was replaced by 1-(4-{3-[(2S)-2-methylpyrrolidin-1-yl]propoxy}phenyl)-1H-pyrazole-4-carboxylic acid hydrochloride obtained in Example 4-(2).

1H NMR (600 MHz, CHLOROFORM-d) δ ppm 1.08 (d, J=6.0 Hz, 3H) 1.37-1.44 (m, 1H) 1.57-1.72 (m, 2H) 1.87-1.94 (m, 1H) 1.95-2.03 (m, 1H) 2.08-2.13 (m, 2H) 2.16-2.22 (m, 1H) 2.25-2.32 (m, 1H) 2.94-3.00 (m, 1H) 3.19-3.24 (m, 1H) 4.02-4.08 (m, 2H) 6.97 (d, J=8.7 Hz, 2H) 7.56 (d, J=8.7 Hz, 2H) 7.93 (s, 1H) 8.30 (s, 1H)

MS (ESI/APCI Dual) (Positive) m/z; 329 (M+H)+

Example 5

Preparation of 1-(4-{3-[(2S)-2-methylpyrrolidin-1-yl]propoxy}phenyl)-1H-pyrazole-4-carbonitrile

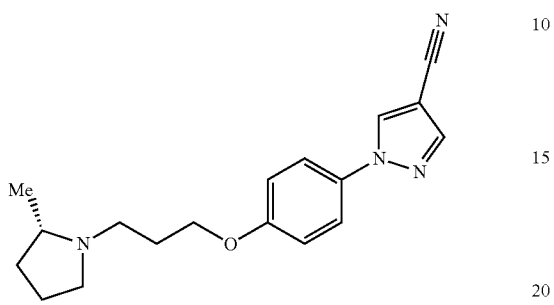

[Formula 39]

The same procedure as shown in Example 3 was repeated to give the titled compound, except that 1-(4-{3-[(2R)-2-methylpyrrolidin-1-yl]propoxy}phenyl)-1H-pyrazole-4-carboxamide was replaced by 1-(4-{3-[(2S)-2-methylpyrrolidin-1-yl]propoxy}phenyl)-1H-pyrazole-4-carboxamide obtained in Example 4-(3).

1H NMR (600 MHz, CHLOROFORM-d) δ ppm 1.08 (d, J=6.4 Hz, 3H) 1.38-1.44 (m, 1H) 1.59-1.82 (m, 2H) 1.88-1.95 (m, 1H) 1.96-2.04 (m, 2H) 2.08-2.13 (m, 1H) 2.16-2.23 (m, 1H) 2.25-2.34 (m, 1H) 2.93-3.01 (m, 1H) 3.14-3.20 (m, 1H) 4.04-4.09 (m, 2H) 6.99 (d, J=9.2 Hz, 2H) 7.54 (d, J=9.2 Hz, 2H) 7.95 (s, 1H) 8.18 (s, 1H)

MS (ESI/APCI Dual) (Positive) m/z; 311 (M+H)+

Example 6

Preparation of 4-{[1-(4-{3-[(2R)-2-methylpyrrolidin-1-yl]propoxy}phenyl)-1H-pyrazol-4-yl]carbonyl}morpholine (1) Preparation of 4-(1H-pyrazol-4-ylcarbonyl)morpholine

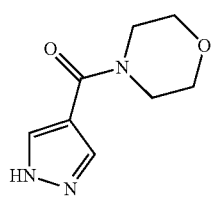

[Formula 40]

A suspension of 1H-pyrazole-4-carboxylic acid (1.05 g), 1-{3-(dimethylamino)propyl}-3-ethylcarbodiimide hydrochloride (2.5 g), 1-hydroxybenzotriazole hydrate (1.6 g) and morpholine (1.2 g) in chloroform (18 mL) was stirred overnight at room temperature. The reaction mixture was concentrated under reduced pressure, and the resulting residue was purified by NH-type silica gel column chromatography (eluting solvent: chloroform:methanol=100:0 to 95:5) and silica gel column chromatography (eluting solvent: chloroform:methanol=100:0 to 90:10). The resulting colorless solid was washed with ethyl acetate to give the titled compound (1.00 g) as a colorless solid.

(2) Preparation of 4-{[1-(4-{3-[(2R)-2-methylpyrrolidin-1-yl]propoxy}phenyl)-1H-pyrazol-4-yl]carbonyl}morpholine

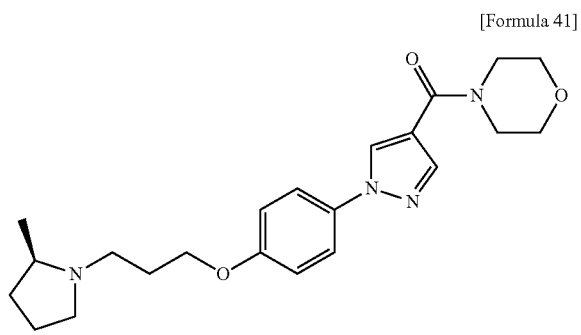

[Formula 41]

A suspension of (2R)-1-[3-(4-iodophenoxy)propyl]-2-methylpyrrolidine obtained in Example 1-(2) (0.30 g), 4-(1H-pyrazol-4-ylcarbonyl)morpholine obtained in Example 6-(1) (0.19 g), (rac-trans-N,N'-dimethylcyclohexane-1,2-diamine (0.049 g), copper iodide (0.017 g) and cesium carbonate (0.57 g) in N,N-dimethylformamide (0.5 mL) was stirred at 120° C. for 1.5 hours. The reaction mixture was cooled to room temperature, diluted with water and extracted with ethyl acetate. The organic layer was concentrated under reduced pressure, and the resulting residue was purified by NH-type silica gel column chromatography (eluting solvent: n-hexane:ethyl acetate=2:1 to 1:1). The resulting crystal was washed with isopropyl ether to give the titled compound (0.20 g) as a white solid.

1H NMR (600 MHz, CHLOROFORM-d) δ ppm 1.08 (d, J=6.0 Hz, 3H), 1.37-1.46 (m, 1H), 1.64-1.82 (m, 2H), 1.87-2.05 (m, 3H), 2.11 (q, J=8.7 Hz, 1H), 2.16-2.23 (m, 1H), 2.25-2.33 (m, 1H), 2.94-3.02 (m, 1H), 3.13-3.20 (m, 1H), 3.67-3.81 (m, 8H), 4.01-4.10 (m, 2H), 6.94-7.01 (m, 2H), 7.52-7.58 (m, 2H), 7.78 (s, 1H), 8.13 (s, 1H)

MS (ESI/APCI Dual) (Positive) m/z; 399 (M+H)+

Example 7

Preparation of 4-{[1-(4-{3-[(2S)-2-methylpyrrolidin-1-yl]propoxy}phenyl)-1H-pyrazol-4-yl]carbonyl}morpholine

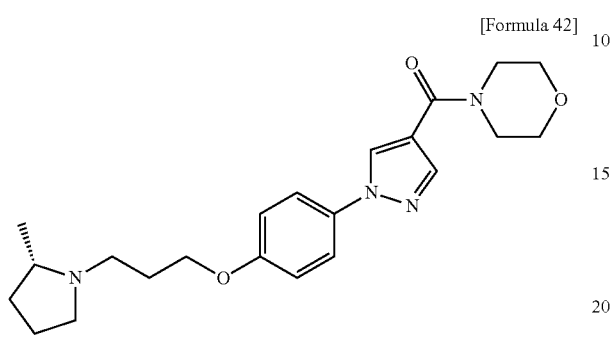

[Formula 42]

The same procedure as shown in Example 6-(2) was repeated to give the titled compound, except that (2R)-1-[3-(4-iodophenoxy)propyl]-2-methylpyrrolidine was replaced by (2S)-1-[3-(4-iodophenoxy)propyl]-2-methylpyrrolidine prepared in Example 4-(1).

1H NMR (600 MHz, CHLOROFORM-d) δ ppm 1.08 (d, J=6.0 Hz, 3H), 1.37-1.46 (m, 1H), 1.64-1.82 (m, 2H), 1.87-2.05 (m, 3H), 2.11 (q, J=8.7 Hz, 1H), 2.16-2.23 (m, 1H), 2.25-2.33 (m, 1H), 2.94-3.02 (m, 1H), 3.13-3.20 (m, 1H), 3.67-3.81 (m, 8H), 4.01-4.10 (m, 2H), 6.94-7.01 (m, 2H), 7.52-7.58 (m, 2H), 7.78 (s, 1H), 8.13 (s, 1H)

MS (ESI/APCI Dual) (Positive) m/z; 399 (M+H)+

Example 8

Preparation of 4-({1-[4-(3-pyrrolidin-1-ylpropoxy)phenyl]-1H-pyrazol-4-yl}carbonyl)morpholine

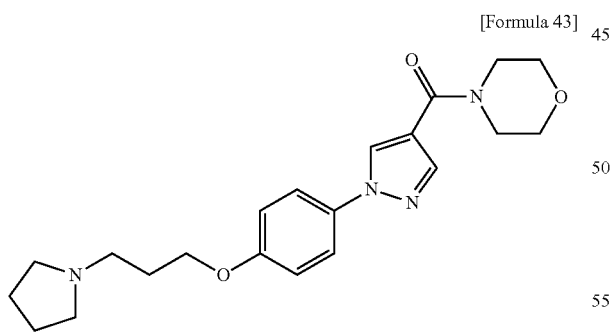

[Formula 43]

The same procedures as shown in Example 1-(2) and Example 6-(2) were repeated to give the titled compound, except that (R)-2-methylpyrrolidine was replaced by pyrrolidine.

1H NMR (600 MHz, CHLOROFORM-d) δ ppm 1.75-1.82 (m, 4H), 1.98-2.05 (m, 2H), 2.49-2.56 (m, 4H), 2.59-2.67 (m, 2H), 3.67-3.81 (m, 8H), 4.06 (t, J=6.4 Hz, 2H), 6.94-7.01 (m, 2H), 7.52-7.58 (m, 2H), 7.77 (s, 1H), 8.13 (s, 1H)

MS (ESI/APCI Dual) (Positive) m/z; 385 (M+H)+

Example 9

Preparation of 4-({1-[4-(3-piperidin-1-ylpropoxy)phenyl]-1H-pyrazol-4-yl}carbonyl)morpholine

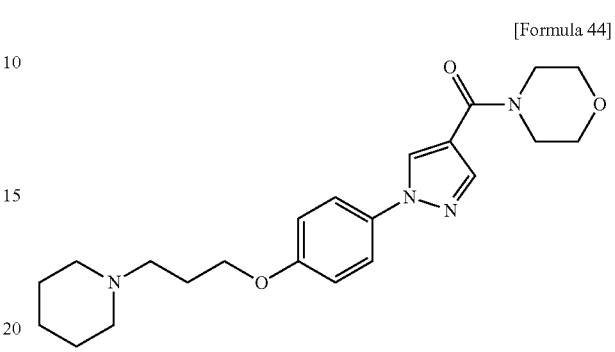

[Formula 44]

The same procedures as shown in Example 1-(2) and Example 6-(2) were repeated to give the titled compound, except that (R)-2-methylpyrrolidine was replaced by piperidine.

1H NMR (600 MHz, CHLOROFORM-d) δ ppm 1.41-1.48 (m, 2H), 1.55-1.63 (m, 4H), 1.96-2.03 (m, 2H), 2.34-2.50 (m, 6H), 3.70-3.80 (m, 8H), 4.05 (t, J=6.4 Hz, 2H), 6.98 (d, J=9.2 Hz, 2H), 7.56 (d, J=9.2 Hz, 2H), 7.78 (s, 1H), 8.14 (s, 1H)

MS (ESI/APCI Dual) (Positive) m/z; 399 (M+H)+

Example 10

Preparation of 4-[(1-{4-[3-(2,2-dimethylpyrrolidin-1-yl)propoxy]phenyl}-1H-pyrazol-4-yl)carbonyl]morpholine

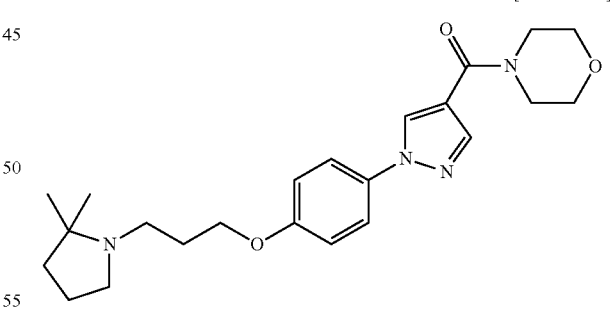

[Formula 45]

The same procedures as shown in Example 1-(2) and Example 6-(2) were repeated to give the titled compound, except that (R)-2-methylpyrrolidine was replaced by 2,2-dimethylpiperidine.

1H NMR (600 MHz, CHLOROFORM-d) δ ppm 0.97 (s, 6H), 1.60-1.66 (m, 2H), 1.71-1.80 (m, 2H), 1.90-1.98 (m, 2H), 2.54 (t, J=7.1 Hz, 2H), 2.76 (t, J=7.3 Hz, 2H), 3.68-3.80 (m, 8H), 4.06 (t, J=6.4 Hz, 2H), 6.95-7.00 (m, 2H), 7.53-7.58 (m, 2H), 7.78 (s, 1H), 8.13 (s, 1H)

MS (ESI/APCI Dual) (Positive) m/z; 413 (M+H)+

Example 11

Preparation of N-tert-butyl-1-{4-[3-(2-methylpyrrolidin-1-yl)propoxy]phenyl}-1H-pyrazole-4-carboxamide (1) Preparation of N-tert-butyl-1H-pyrazole-4-carboxamide

[Formula 46]

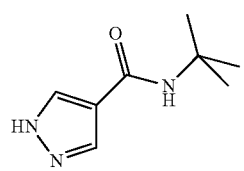

The same procedure as shown in Example 6-(1) was repeated to give the titled compound, except that morpholine was replaced by 2-methylpropane-2-amine.

(2) Preparation of 1-[3-(4-iodophenoxy)propyl]-2-methylpyrrolidine

[Formula 47]

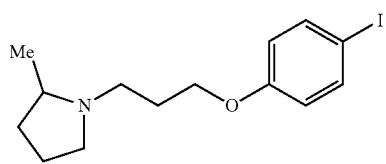

The same procedure as shown in Example 1-(2) was repeated to give the titled compound, except that (R)-2-methylpyrrolidine was replaced by 2-methylpyrrolidine.

(3) Preparation of N-tert-butyl-1-{4-[3-(2-methylpyrrolidin-1-yl)propoxy]phenyl}-1H-pyrazole-4-carboxamide

[Formula 48]

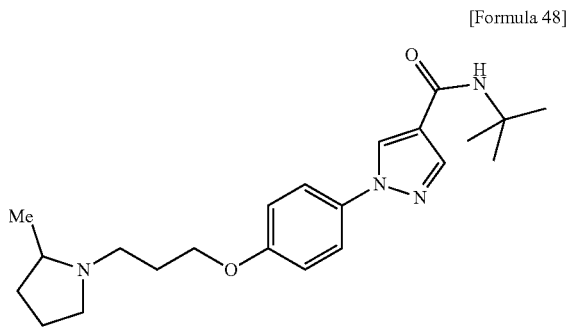

The same procedure as shown in Example 1-(3) was repeated to give the titled compound, except that (2R)-1-[3-(4-iodophenoxy)propyl]-2-methylpyrrolidine was replaced by 1-[3-(4-iodophenoxy)propyl]-2-methylpyrrolidine obtained in Example 11-(2), and 1H-pyrazole-4-carboxylic acid ethyl ester was replaced by N-tert-butyl-1H-pyrazole-4-carboxamide obtained in Example 11-(1).

1H NMR (600 MHz, CHLOROFORM-d) δ ppm 1.11 (d, J=6.4 Hz, 3H), 1.47 (s, 9H), 1.75-1.82 (m, 1H), 1.90-1.96 (m, 1H), 1.98-2.05 (m, 2H), 2.11-2.17 (m, 1H), 2.20-2.25 (m, 1H), 2.29-2.36 (m, 1H), 2.96-3.02 (m, 1H), 3.17-3.21 (m, 1H), 4.03-4.09 (m, 2H), 5.63 (br. s., 1H), 6.98 (d, J=9.2 Hz, 2H), 7.55 (d, J=9.2 Hz, 2H), 7.82 (s, 1H), 8.21 (s, 1H)
MS (ESI/APCI Dual) (Positive) m/z; 385 (M+H)+

Example 12

Preparation of N-tert-butyl-1-{4-[3-(2,5-dimethylpyrrolidin-1-yl)propoxy]phenyl}-1H-pyrazole-4-carboxamide

[Formula 49]

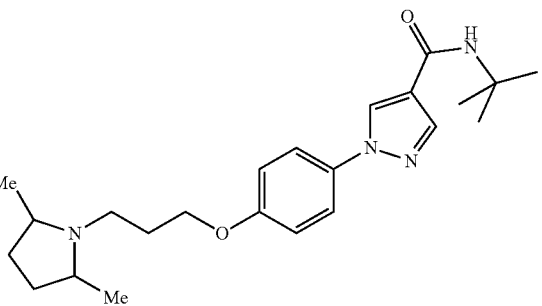

The same procedures as shown in Example 11-(2) and Example 11-(3) were repeated to give the titled compound, except that 2-methylpyrrolidine was replaced by 2,5-dimethylpyrrolidine.

1H NMR (600 MHz, CHLOROFORM-d) δ ppm 1.11 (d, J=6.0 Hz, 6H), 1.33-1.41 (m, 2H), 1.47 (s, 9H), 1.77-1.85 (m, 2H), 1.91-2.04 (m, 2H), 2.55-2.64 (m, 2H), 2.73-2.77 (m, 2H), 4.04 (t, J=6.2 Hz, 2H), 5.61 (s, 1H), 6.97 (d, J=8.7 Hz, 2H), 7.56 (d, J=9.2 Hz, 2H), 7.82 (s, 1H), 8.21 (s, 1H)
MS (ESI/APCI Dual) (Positive) m/z; 399 (M+H)+

Example 13

Preparation of N-tert-butyl-1-[4-(3-pyrrolidin-1-ylpropoxy)phenyl]-1H-pyrazole-4-carboxamide

[Formula 50]

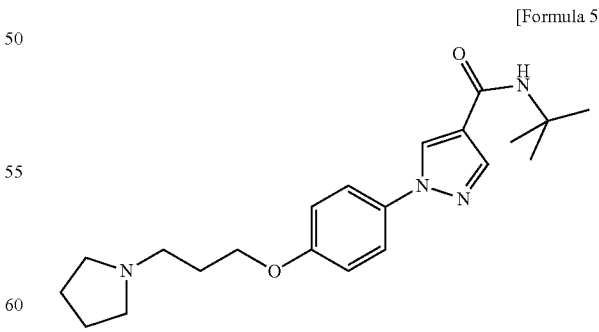

The same procedures as shown in Example 11-(2) and Example 11-(3) were repeated to give the titled compound, except that 2-methylpyrrolidine was replaced by pyrrolidine.

1H NMR (600 MHz, CHLOROFORM-d) δ ppm 1.46 (s, 9H), 1.76-1.81 (m, 4H), 1.98-2.05 (m, 2H), 2.49-2.56 (m, 4H), 2.58-2.67 (m, 2H), 4.05 (t, J=6.6 Hz, 2H), 5.60 (s, 1H), 6.92-7.01 (m, 2H), 7.50-7.58 (m, 2H), 7.81 (s, 1H), 8.20 (s, 1H)

MS (ESI/APCI Dual) (Positive) m/z; 371 (M+H)+

Example 14

Preparation of N-tert-butyl-1-{4-[3-(diethylamino)propoxy]phenyl}-1H-pyrazole-4-carboxamide

[Formula 51]

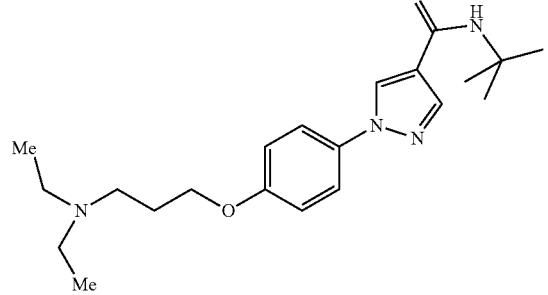

The same procedures as shown in Example 11-(2) and Example 11-(3) were repeated to give the titled compound, except that 2-methylpyrrolidine was replaced by diethylamine.

1H NMR (600 MHz, CHLOROFORM-d) δ ppm 2.55 (q, J=7.0 Hz, 4H), 2.59-2.63 (m, 2H), 4.05 (t, J=6.4 Hz, 2H), 5.60 (s, 1H), 6.97 (d, 2H), 7.55 (d, J=9.2 Hz, 2H), 7.82 (s, 1H), 8.20 (s, 1H)

MS (ESI/APCI Dual) (Positive) m/z; 373 (M+H)+

Example 15

Preparation of N-(4-fluorophenyl)-1-{4-[3-(2-methylpyrrolidin-1-yl)propoxy]phenyl}-1H-pyrazole-4-carboxamide (1) Preparation of 1-{4-[3-(2-methylpyrrolidin-1-yl)propoxy]phenyl}-1H-pyrazole-4-carboxylic acid hydrochloride

[Formula 52]

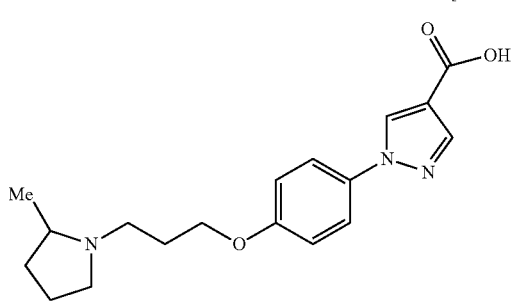

The same procedures as shown in Example 1-(3) and Example 2-(1) were repeated to give the titled compound, except that (2R)-1-[3-(4-iodophenoxy)propyl]-2-methylpyrrolidine was replaced by 1-[3-(4-iodophenoxy)propyl]-2-methylpyrrolidine obtained in Example 11-(2).

(2) N-(4-Fluorophenyl)-1-{4-[3-(2-methylpyrrolidin-1-yl)propoxy]phenyl}-1H-pyrazole-4-carboxamide

[Formula 53]

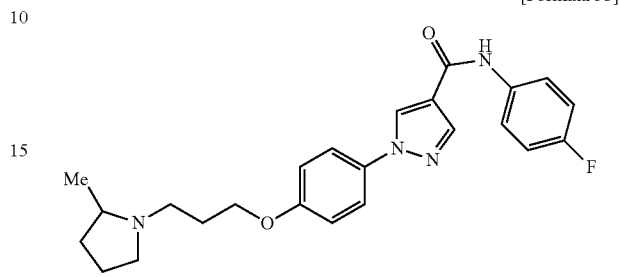

The same procedure as shown in Example 2-(2) was repeated to give the titled compound, except that 1-(4-{3-[(2R)-2-methylpyrrolidin-1-yl]propoxy}phenyl)-1H-pyrazole-4-carboxylic acid hydrochloride was replaced by 1-{4-[3-(2-methylpyrrolidin-1-yl)propoxy]phenyl}-1H-pyrazole-4-carboxylic acid hydrochloride obtained in Example 15-(1), and aqueous ammonia was replaced by 4-fluoroaniline.

1H NMR (600 MHz, CHLOROFORM-d) δ ppm 1.10 (d, J=6.0 Hz, 3H), 1.40-2.35 (m, 9H), 2.97-3.03 (m, 1H), 3.17-3.23 (m, 1H), 4.05-4.12 (m, 2H), 6.99-7.02 (m, 2H), 7.15-7.20 (m, 2H), 7.48 (s, 1H), 7.56-7.62 (m, 2H), 8.00 (s, 1H), 8.37 (s, 1H)

MS (ESI/APCI Dual) (Positive) m/z; 423 (M+H)+

Example 16

Preparation of N-(4-fluorophenyl)-1-[4-(3-pyrrolidin-1-ylpropoxy)phenyl]-1H-pyrazole-4-carboxamide

[Formula 54]

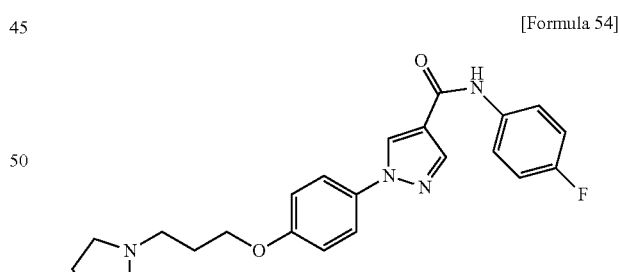

The same procedures as shown in Example 1-(2), Example 1-(3), Example 2-(1) and Example 15-(2) were repeated to give the titled compound, except that 2-methylpyrrolidine was replaced by pyrrolidine.

1H NMR (600 MHz, CHLOROFORM-d) δ ppm 1.77-1.83 (m, 4H), 2.00-2.07 (m, 2H), 2.52-2.58 (m, 4H), 2.66 (t, J=7.6 Hz, 2H), 4.07 (t, J=6.4 Hz, 2H), 6.99 (d, J=9.2 Hz, 2H), 7.06 (t, J=8.5 Hz, 2H), 7.47 (s, 1H), 7.54-7.61 (m, 2H), 7.58 (d, J=9.2 Hz, 2H), 8.00 (s, 1H), 8.37 (s, 1H)

MS (ESI/APCI Dual) (Positive) m/z; 409 (M+H)+

Example 17

Preparation of N-(4-methylphenyl)-1-{4-[3-(2-methylpyrrolidin-1-yl)propoxy]phenyl}-1H-pyrazole-4-carboxamide

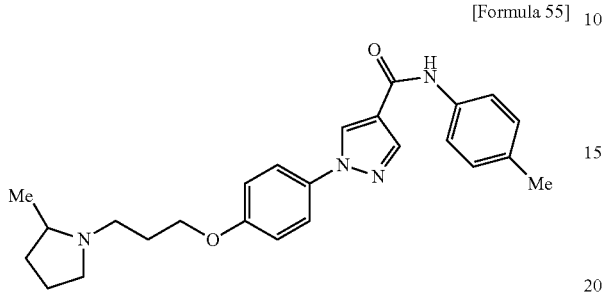

[Formula 55]

The same procedure as shown in Example 15-(2) was repeated to give the titled compound, except that 4-fluoroaniline was replaced by 4-methylaniline.

1H NMR (600 MHz, CHLOROFORM-d) δ ppm 1.12 (br. s., 3H), 1.46 (br. s., 1H), 1.66-1.87 (m, 2H), 1.89-2.39 (m, 9H), 3.01 (br. s., 1H), 3.21 (br. s., 1H), 4.04-4.12 (m, 2H), 7.00 (d, J=9.2 Hz, 2H), 7.18 (d, J=8.3 Hz, 2H), 7.42 (s, 1H), 7.49 (d, J=8.3 Hz, 2H), 7.60 (d, J=9.2 Hz, 2H), 7.99 (br. s., 1H), 8.36 (s, 1H)

MS (ESI/APCI Dual) (Positive) m/z; 419 (M+H)$^+$

Example 18

Preparation of 1-{4-[3-(2-methylpyrrolidin-1-yl)propoxy]-phenyl}-1H-pyrazole-4-carboxylic acid 4-fluorobenzylamide

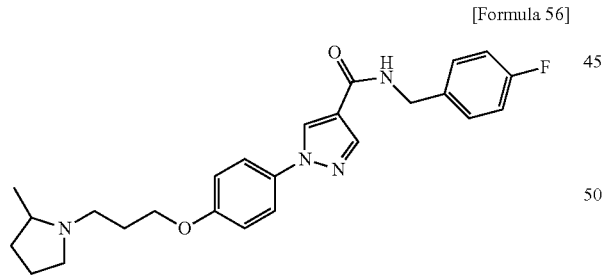

[Formula 56]

The same procedure as shown in Example 15-(2) was repeated to give the titled compound, except that 4-fluoroaniline was replaced by 4-fluorobenzylamine.

1H NMR (600 MHz, CHLOROFORM-d) δ ppm 1.08 (d, J=6.0 Hz, 3H), 1.41 (dddd, J=12.5, 10.4, 8.7, 6.0 Hz, 1H), 1.65-1.72 (m, 1H), 1.73-1.82 (m, 1H), 1.87-1.95 (m, 1H), 1.95-2.05 (m, 2H), 2.11 (q, J=9.2 Hz, 1H), 2.16-2.22 (m, 1H), 2.25-2.32 (m, 1H), 2.94-3.01 (m, 1H), 3.14-3.20 (m, 1H), 4.02-4.09 (m, 2H), 4.59 (d, J=6.0 Hz, 2H), 6.05-6.10 (m, 1H), 6.95-6.99 (m, 2H), 7.01-7.06 (m, 2H), 7.30-7.35 (m, 2H), 7.55 (d, J=9.2 Hz, 2H), 7.88 (s, 1H), 8.28 (s, 1H)

MS (ESI/APCI Dual) (Positive) m/z; 437 (M+H)$^+$

Example 19

Preparation of 1-{4-[3-(2-methylpyrrolidin-1-yl)-propoxy]-phenyl}-1H-pyrazole-4-carboxylic acid dimethylamide

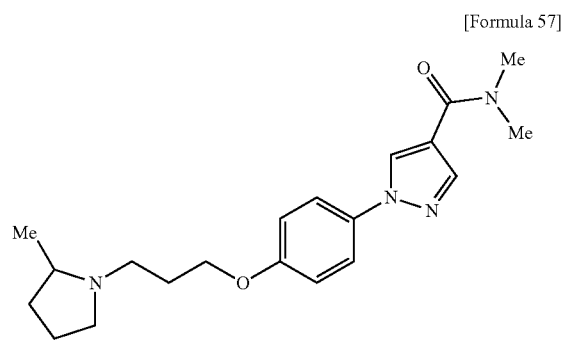

[Formula 57]

The same procedure as shown in Example 15-(2) was repeated to give the titled compound, except that 4-fluoroaniline was replaced by dimethylamine.

1H NMR (600 MHz, CHLOROFORM-d) δ ppm 1.08 (d, J=6.0 Hz, 3H), 1.37-1.45 (m, 1H), 1.64-1.72 (m, 1H), 1.73-1.82 (m, 1H), 1.87-1.95 (m, 1H), 1.95-2.06 (m, 2H), 2.11 (q, J=8.7 Hz, 1H), 2.16-2.23 (m, 1H), 2.25-2.33 (m, 1H), 2.94-3.01 (m, 1H), 3.03-3.33 (m, 7H), 4.02-4.09 (m, 2H), 6.94-7.01 (m, 2H), 7.54-7.59 (m, 2H), 7.86 (s, 1H), 8.17 (s, 1H)

MS (ESI/APCI Dual) (Positive) m/z; 357 (M+H)$^+$

Example 20

Preparation of 1-(4-{3-[(2R)-2-methylpyrrolidin-1-yl]propoxy}phenyl)-1H-pyrazole-4-carboxylic acid bis-(2-hydroxyethyl)-amide

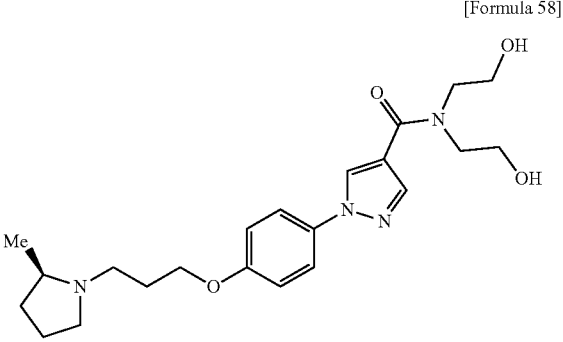

[Formula 58]

The same procedure as shown in Example 15-(2) was repeated to give the titled compound, except that 4-fluoroaniline was replaced by diethanolamine.

1H NMR (600 MHz, CHLOROFORM-d) δ ppm 1.09 (d, J=6.0 Hz, 3H), 1.37-1.47 (m, 1H), 1.65-1.83 (m, 4H), 1.87-2.06 (m, 3H), 2.12 (q, J=9.0 Hz, 1H), 2.16-2.23 (m, 1H), 2.26-2.36 (m, 1H), 2.94-3.02 (m, 1H), 3.13-3.21 (m, 1H), 3.70 (br. s., 4H), 3.83-4.08 (m, 6H), 6.90-6.99 (m, 2H), 7.50-7.56 (m, 2H), 7.99 (s, 1H), 8.32 (s, 1H)

MS (ESI/APCI Dual) (Positive) m/z; 417 (M+H)$^+$

Example 21

Preparation of azetidin-1-yl-(1-{4-[3-(2-methylpyrrolidin-1-yl)propoxy]phenyl}-1H-pyrazol-4-yl)methanone

[Formula 59]

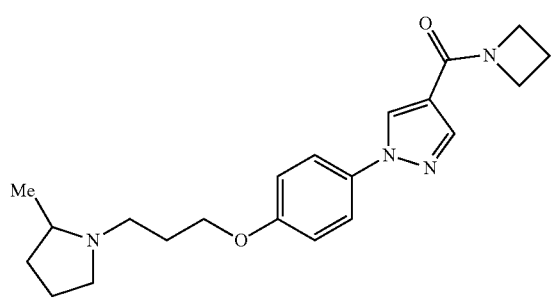

The same procedure as shown in Example 15-(2) was repeated to give the titled compound, except that 4-fluoroaniline was replaced by cyclobutylamine.

1H NMR (600 MHz, CHLOROFORM-d) δ ppm 1.08 (d, J=6.0 Hz, 3H), 1.37-1.45 (m, 1H), 1.65-1.72 (m, 1H), 1.73-1.81 (m, 1H), 1.88-1.95 (m, 1H), 1.95-2.05 (m, 2H), 2.10 (q, J=8.9 Hz, 1H), 2.17-2.22 (m, 1H), 2.25-2.32 (m, 1H), 2.36-2.43 (m, 2H), 2.94-3.01 (m, 1H), 3.17 (td, J=8.6, 2.5 Hz, 1H), 4.02-4.09 (m, 2H), 4.17-4.24 (m, 2H), 4.41-4.48 (m, 2H), 6.95-6.99 (m, 2H), 7.54-7.58 (m, 2H), 7.85 (s, 1H), 8.22 (s, 1H)

MS (ESI/APCI Dual) (Positive) m/z; 369 (M+H)+

Example 22

Preparation of 4-[(3,3-difluoropyrrolidin-1-yl)carbonyl]-1-(4-{3-[(2R)-2-methylpyrrolidin-1-yl]propoxy}phenyl)-1H-pyrazole

[Formula 60]

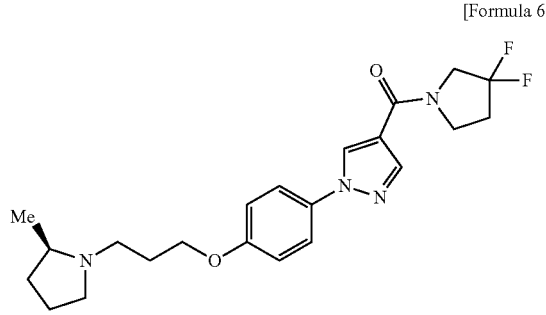

The same procedure as shown in Example 2-(2) was repeated to give the titled compound, except that aqueous ammonia was replaced by 3,3-difluoropyrrolidine.

1H NMR (600 MHz, CHLOROFORM-d) δ ppm 1.10 (d, J=6.0 Hz, 3H), 1.38-1.48 (m, 1H), 1.65-1.84 (m, 2H), 1.88-1.96 (m, 1H), 1.97-2.07 (m, 2H), 2.09-2.16 (m, 1H), 2.17-2.25 (m, 1H), 2.27-2.35 (m, 1H), 2.39-2.56 (m, 2H), 2.95-3.03 (m, 1H), 3.14-3.23 (m, 1H), 3.87-4.14 (m, 6H), 6.99 (d, J=9.2 Hz, 2H), 7.58 (d, J=9.2 Hz, 2H), 7.92 (br. s., 1H), 8.26 (br. s., 1H)

MS (ESI/APCI Dual) (Positive) m/z; 419 (M+H)+

Example 23

Preparation of (4-fluorophenyl)[1-(4-{3-[(2R)-2-methylpyrrolidin-1-yl]propoxy}phenyl)-1H-pyrazol-4-yl]methanone (1) Preparation of 1-(4-{3-[(2R)-2-methylpyrrolidin-1-yl]propoxy}phenyl)-1H-pyrazole-4-carboxylic acid methoxymethylamide

[Formula 61]

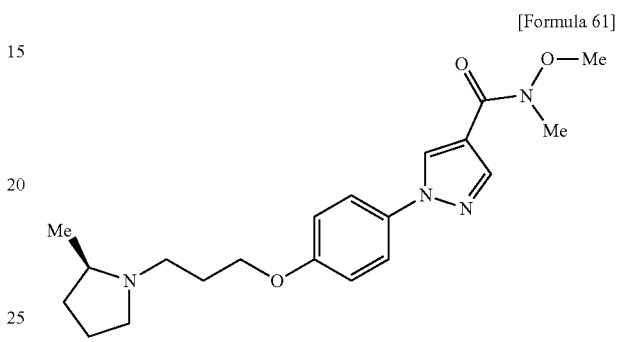

The same procedure as shown in Example 2-(2) was repeated to give the titled compound, except that aqueous ammonia was replaced by N,O-dimethylhydroxylamine.

(2) Preparation of (4-fluorophenyl)[1-(4-{3-[(2R)-2-methylpyrrolidin-1-yl]propoxy}phenyl)-1H-pyrazol-4-yl]methanone

[Formula 62]

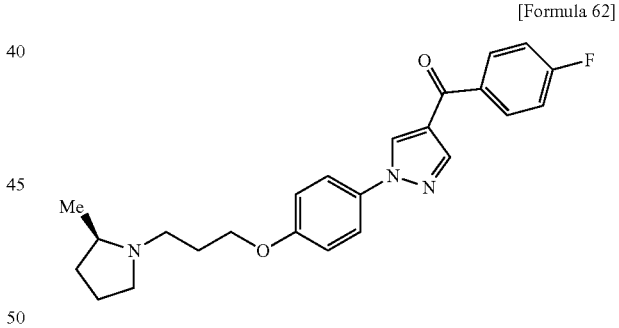

To a solution of 1-(4-{3-[(2R)-2-methylpyrrolidin-1-yl]propoxy}phenyl)-1H-pyrazole-4-carboxylic acid methoxymethylamide obtained in Example 23-(1) (0.25 g) in tetrahydrofuran (3 mL), a solution of 4-fluorophenylmagnesium bromide in tetrahydrofuran (1.0 M, 4.0 mL) was added dropwise in an ice bath and stirred at room temperature for 2 hours. The reaction mixture was diluted with saturated aqueous ammonium chloride and extracted with chloroform. The organic layer was dried over sodium sulfate and concentrated under reduced pressure, and the resulting residue was purified by NH-type silica gel column chromatography (eluting solvent: hexane:ethyl acetate=5:1 to 4:1) and silica gel column chromatography (eluting solvent: chloroform:methanol=95:5) to give the titled compound (0.11 g) as a light-blue solid.

1H NMR (600 MHz, CHLOROFORM-d) δ ppm 1.10 (d, J=6.0 Hz, 3H), 1.39-1.47 (m, 1H), 1.64-1.84 (m, 2H), 1.90-

1.96 (m, 1H), 1.99-2.06 (m, 2H), 2.12-2.21 (m, 1H), 2.24 (s, 1H), 2.34 (s, 1H), 2.97-3.03 (m, 1H), 3.17-3.23 (m, 1H), 4.04-4.10 (m, 2H), 7.00 (d, J=9.2 Hz, 2H), 7.17-7.22 (m, 2H), 7.61 (d, J=9.2 Hz, 2H), 7.93 (dd, J=8.7, 5.5 Hz, 2H), 8.08 (s, 1H), 8.34 (s, 1H)

MS (ESI/APCI Dual) (Positive) m/z; 408 (M+H)+

Example 24

Preparation of [1-(4-{3-[(2R)-2-methylpyrrolidin-1-yl]propoxy}phenyl)-1H-pyrazol-4-yl](phenyl)methanone

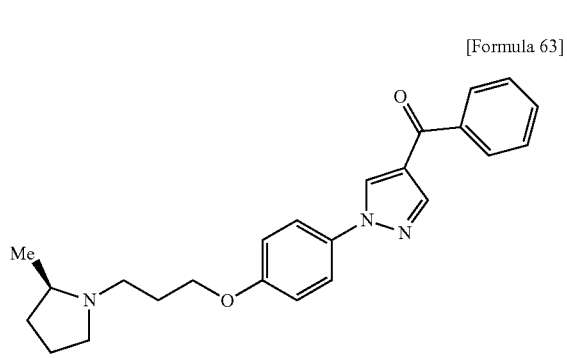

[Formula 63]

The same procedure as shown in Example 23-(2) was repeated to give the titled compound, except that 4-fluorophenylmagnesium bromide was replaced by phenylmagnesium bromide.

1H NMR (600 MHz, CHLOROFORM-d) δ ppm 1.09 (d, J=6.4 Hz, 3H), 1.38-1.45 (m, 1H), 1.64-1.73 (m, 1H), 1.74-1.81 (m, 1H), 1.87-2.07 (m, 3H), 2.11 (q, J=9.0 Hz, 1H), 2.18-2.23 (m, 1H), 2.27-2.32 (m, 1H), 2.96-3.01 (m, 1H), 3.15-3.19 (m, 1H), 4.04-4.10 (m, 2H), 7.00 (d, J=9.2 Hz, 2H), 7.49-7.53 (m, 2H), 7.57-7.63 (m, 3H), 7.89 (d, J=6.9 Hz, 2H), 8.11 (s, 1H), 8.35 (s, 1H)

MS (ESI/APCI Dual) (Positive) m/z; 390 (M+H)+

Example 25

Preparation of (1-{4-[3-(2-methylpyrrolidin-1-yl)propoxy]phenyl}-1H-pyrazol-4-yl)(pyridin-2-yl)methanone (1) Preparation of (1H-pyrazol-4-yl)-pyridin-2-ylmethanone

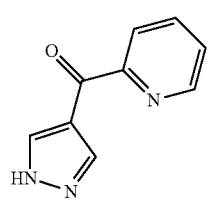

[Formula 64]

To a solution of 4-iodopyrazole (1.0 g) in tetrahydrofuran (10 mL), a solution of n-butyllithium in hexane (2.6 M, 4.8 mL) was added dropwise at −10° C. and stirred at room temperature for 1 hour. The reaction mixture was cooled to −10° C. and ethyl picolinate (0.86 g) was added thereto, followed by stirring at room temperature for 1.5 hours. The reaction mixture was diluted with saturated aqueous ammonium chloride and extracted with diethyl ether. The organic layer was washed with brine, dried over sodium sulfate and concentrated under reduced pressure. The resulting residue was purified by NH-type silica gel column chromatography (eluting solvent: hexane:ethyl acetate=1:1 to 1:2) to give the titled compound (0.090 g) as a colorless solid.

(2) Preparation of (1-{4-[3-(2-methylpyrrolidin-1-yl)propoxy]phenyl}-1H-pyrazol-4-yl)(pyridin-2-yl)methanone

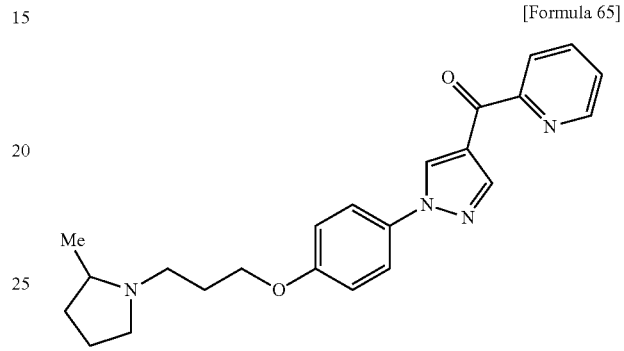

[Formula 65]

The same procedure as shown in Example 1-(3) was repeated to give the titled compound, except that (2R)-1-[3-(4-iodophenoxy)propyl]-2-methylpyrrolidine was replaced by 1-[3-(4-iodophenoxy)propyl]-2-methylpyrrolidine obtained in Example 11-(2), and 1H-pyrazole-4-carboxylic acid ethyl ester was replaced by (1H-pyrazol-4-yl)-pyridin-2-ylmethanone obtained in Example 25-(1).

1H NMR (600 MHz, CHLOROFORM-d) δ ppm 1.09 (d, J=6.4 Hz, 3H), 1.38-1.45 (m, 1H), 1.63-1.72 (m, 1H), 1.74-1.82 (m, 1H), 1.89-1.96 (m, 1H), 1.97-2.05 (m, 2H), 2.09-2.14 (m, 1H), 2.17-2.24 (m, 1H), 2.27-2.33 (m, 1H), 2.94-3.01 (m, 1H), 3.16-3.20 (m, 1H), 4.04-4.10 (m, 2H), 7.00 (d, J=8.7 Hz, 2H), 7.48-7.51 (m, 1H), 7.65 (d, J=8.7 Hz, 2H), 7.87-7.91 (m, 1H), 8.18-8.20 (m, 1H), 8.54 (s, 1H), 8.74-8.76 (m, 1H), 9.04 (s, 1H)

MS (ESI/APCI Dual) (Positive) m/z; 391 (M+H)+

Example 26

Preparation of [1-(4-{3-[(2R)-2-methylpyrrolidin-1-yl]propoxy}phenyl)-1H-pyrazol-4-yl](pyridin-4-yl)methanone

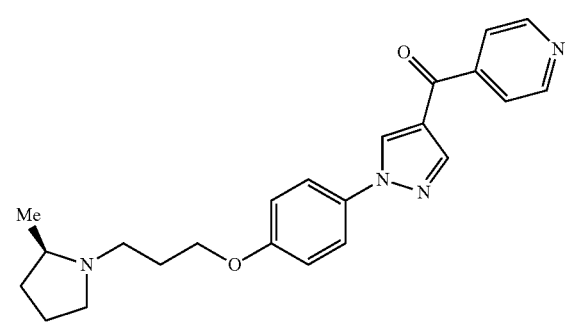

[Formula 66]

The same procedures as shown in Example 25-(1) and Example 25-(2) were repeated to give the titled compound, except that ethyl picolinate was replaced by ethyl isonicotinate, and 1-[3-(4-iodophenoxy)propyl]-2-methylpyrrolidine was replaced by (2R)-1-[3-(4-iodophenoxy)propyl]-2-methylpyrrolidine obtained in Example 1-(2).

1H NMR (600 MHz, CHLOROFORM-d) δ ppm 1.08 (d, J=6.0 Hz, 3H), 1.38-1.44 (m, 1H), 1.65-1.72 (m, 1H), 1.73-1.81 (m, 1H), 1.88-1.95 (m, 1H), 1.96-2.05 (m, 2H), 2.11 (q, J=9.0 Hz, 1H), 2.17-2.23 (m, 1H), 2.26-2.32 (m, 1H), 2.95-3.01 (m, 1H), 3.17 (td, J=8.5, 2.8 Hz, 1H), 4.04-4.10 (m, 2H), 7.00 (d, J=9.2 Hz, 2H), 7.60 (d, J=9.2 Hz, 2H), 7.67 (d, J=6.0 Hz, 2H), 8.10 (s, 1H), 8.35 (s, 1H), 8.83 (d, J=6.0 Hz, 2H)

MS (ESI/APCI Dual) (Positive) m/z; 391 (M+H)⁺

Example 27

Preparation of 1-[1-(4-{3-[(2R)-2-methylpyrrolidin-1-yl]propoxy}phenyl)-1H-pyrazol-4-yl]ethanone

[Formula 67]

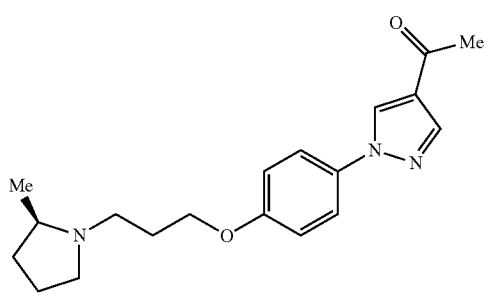

The same procedure as shown in Example 23-(2) was repeated to give the titled compound, except that 4-fluorophenylmagnesium bromide was replaced by methylmagnesium iodide.

1H NMR (600 MHz, CHLOROFORM-d) δ ppm 1.08 (d, J=6.0 Hz, 3H), 1.38-1.45 (m, 1H), 1.64-1.72 (m, 1H), 1.74-1.81 (m, 1H), 1.88-1.94 (m, 1H), 1.96-2.04 (m, 2H), 2.08-2.14 (m, 1H), 2.17-2.23 (m, 1H), 2.26-2.32 (m, 1H), 2.48 (s, 3H), 2.95-3.00 (m, 1H), 3.15-3.19 (m, 1H), 4.03-4.09 (m, 2H), 6.99 (d, J=9.2 Hz, 2H), 7.58 (d, J=9.2 Hz, 2H), 8.05 (s, 1H), 8.28 (s, 1H)

MS (ESI/APCI Dual) (Positive) m/z; 328 (M+H)⁺

Example 28

Preparation of 1-(4-{3-[(2R)-2-methylpyrrolidin-1-yl]propoxy}phenyl)-4-nitro-1H-pyrazole

[Formula 68]

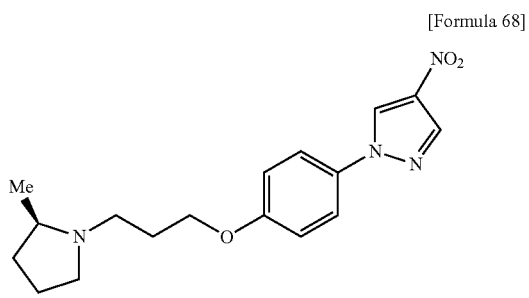

The same procedure as shown in Example 1-(3) was repeated to give the titled compound, except that 1H-pyrazole-4-carboxylic acid ethyl ester was replaced by 4-nitro-1H-pyrazole.

1H NMR (600 MHz, CHLOROFORM-d) δ ppm 1.08 (d, J=6.0 Hz, 3H), 1.36-1.47 (m, 1H), 1.65-1.83 (m, 2H), 1.87-1.95 (m, 1H), 1.96-2.06 (m, 2H), 2.11 (q, J=9.0 Hz, 1H), 2.16-2.24 (m, 1H), 2.25-2.33 (m, 1H), 2.91-3.03 (m, 1H), 3.12-3.23 (m, 1H), 4.02-4.13 (m, 2H), 6.96-7.07 (m, 2H), 7.53-7.63 (m, 2H), 8.23 (s, 1H), 8.51 (s, 1H)

MS (ESI/APCI Dual) (Positive) m/z; 331 (M+H)⁺

Example 29

Preparation of 4-chloro-N-[1-(4-{3-[(2R)-2-methylpyrrolidin-1-yl]propoxy}phenyl)-1H-pyrazol-4-yl]butylamide (1) Preparation of 1-(4-{3-[(2R)-2-methylpyrrolidin-1-yl]propoxy}phenyl)-1H-pyrazol-4-ylamine

[Formula 69]

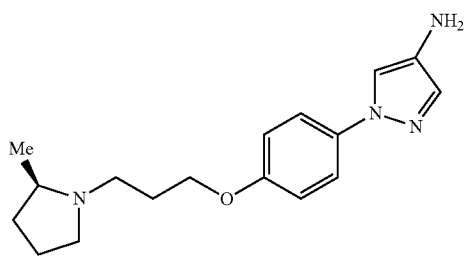

To a solution of 1-(4-{3-[(2R)-2-methylpyrrolidin-1-yl]propoxy}phenyl)-4-nitro-1H-pyrazole obtained in Example 28 (0.67 g) in methanol (10 mL), 10% palladium on carbon (0.067 g) was added and stirred under a hydrogen atmosphere at room temperature for 4 hours. The reaction mixture was filtered through celite, and the filtrate was concentrated under reduced pressure. The resulting residue was purified by NH-type silica gel column chromatography (eluting solvent: hexane:ethyl acetate=3:1 to 1:1) to give the titled compound (0.258 g) as a yellow solid.

(2) Preparation of 4-chloro-N-[1-(4-{3-[(2R)-2-methylpyrrolidin-1-yl]propoxy}phenyl)-1H-pyrazol-4-yl]butylamide

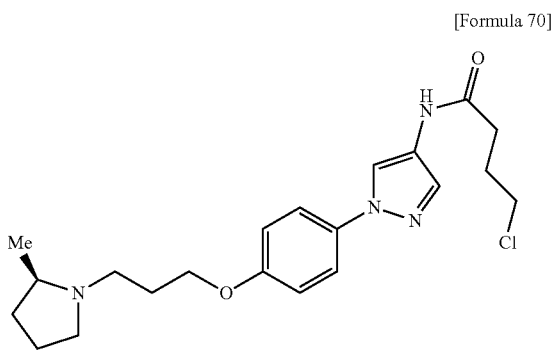

[Formula 70]

To a solution of 1-(4-{3-[(2R)-2-methylpyrrolidin-1-yl]propoxy}phenyl)-1H-pyrazol-4-ylamine obtained in Example 29-(1) (0.256 g) and pyridine (0.135 g) in chloroform (2.6 mL), 4-chlorobutyryl chloride (0.132 g) was added and stirred at room temperature for 30 minutes. The reaction mixture was diluted with saturated aqueous ammonium chloride and extracted with chloroform. The organic layer was washed with water and brine, dried over sodium sulfate and concentrated under reduced pressure to give the titled compound (0.224 g) as a light-yellow solid.

1H NMR (600 MHz, DMSO-$d_6$) δ ppm 1.36 (d, J=6.4 Hz, 3H), 1.54-1.67 (m, 1H), 1.82-2.21 (m, 6H), 2.30-2.52 (m, 3H), 2.97-3.13 (m, 2H), 3.33-3.45 (m, 2H), 3.52-3.72 (m, 3H), 4.00-4.16 (m, 2H), 7.02 (d, J=9.2 Hz, 2H), 7.54-7.74 (m, 3H), 8.42 (s, 1H), 10.19 (s, 1H)

MS (ESI/APCI Dual) (Positive) m/z; 405 (M+H)$^+$

Example 30

Preparation of 1-[1-(4-{3-[(2R)-2-methylpyrrolidin-1-yl]propoxy}phenyl)-1H-pyrazol-4-yl]pyrrolidine-2-one

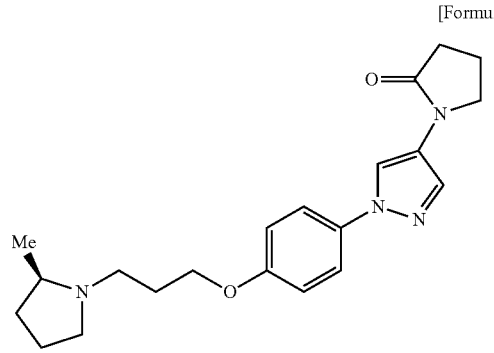

[Formula 71]

To a suspension of 4-chloro-N-[1-(4-{3-[(2R)-2-methylpyrrolidin-1-yl]propoxy}phenyl)-1H-pyrazol-4-yl]butylamide obtained in Example 29-(2) (0.224 g) in tetrahydrofuran (2.0 mL), sodium hydride (55% in mineral oil, 0.111 g) was added and stirred at room temperature for 30 minutes. The reaction mixture was diluted with water and extracted with chloroform. The organic layer was washed with brine, dried over sodium sulfate and concentrated under reduced pressure. The resulting residue was purified by NH-type silica gel column chromatography (eluting solvent: chloroform:methanol=100:1), and the resulting crystal was washed with diisopropyl ether to give the titled compound (0.127 g) as a light-yellow solid.

1H NMR (600 MHz, CHLOROFORM-d) δ ppm 1.09 (d, J=6.4 Hz, 3H), 1.36-1.46 (m, 1H), 1.64-1.84 (m, 2H), 1.87-2.07 (m, 3H), 2.07-2.16 (m, 1H), 2.16-2.33 (m, 4H), 2.57 (t, J=8.0 Hz, 2H), 2.94-3.02 (m, 1H), 3.13-3.22 (m, 1H), 3.80 (t, J=7.3 Hz, 2H), 4.00-4.09 (m, 2H), 6.92-6.99 (m, 2H), 7.54-7.61 (m, 2H), 7.65 (s, 1H), 8.43 (s, 1H)

MS (ESI/APCI Dual) (Positive) m/z; 369 (M+H)$^+$

Example 31

Preparation of 1-[1-(4-{3-[(2S)-2-methylpyrrolidin-1-yl]propoxy}phenyl)-1H-pyrazol-4-yl]pyrrolidine-2-one

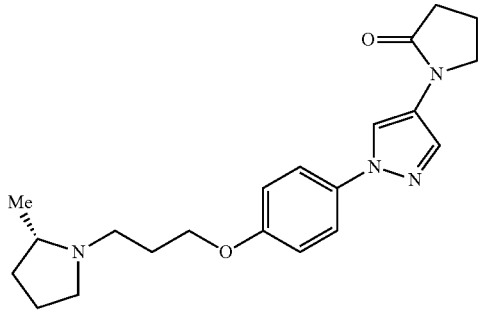

[Formula 72]

The same procedures as shown in Example 28, Example 29-(1), Example 29-(2) and Example 30 were repeated to give the titled compound, except that (2R)-1-[3-(4-iodophenoxy)propyl]-2-methylpyrrolidine was replaced by (2S)-1-[3-(4-iodophenoxy)propyl]-2-methylpyrrolidine obtained in Example 4-(1).

1H NMR (600 MHz, CHLOROFORM-d) δ ppm 1.09 (d, J=6.4 Hz, 3H), 1.36-1.46 (m, 1H), 1.64-1.84 (m, 2H), 1.87-2.07 (m, 3H), 2.07-2.16 (m, 1H), 2.16-2.33 (m, 4H), 2.57 (t, J=8.0 Hz, 2H), 2.94-3.02 (m, 1H), 3.13-3.22 (m, 1H), 3.80 (t, J=7.3 Hz, 2H), 4.00-4.09 (m, 2H), 6.92-6.99 (m, 2H), 7.54-7.61 (m, 2H), 7.65 (s, 1H), 8.43 (s, 1H)

MS (ESI/APCI Dual) (Positive) m/z; 369 (M+H)$^+$

Example 32

Preparation of 1-{1-[4-(3-pyrrolidin-1-ylpropoxy)phenyl]-1H-pyrazol-4-yl}pyrrolidine-2-one

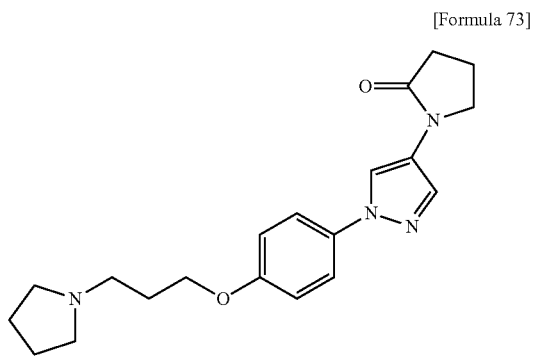

[Formula 73]

The same procedures as shown in Example 1-(2), Example 28, Example 29-(1), Example 29-(2) and Example 30 were repeated to give the titled compound, except that 2-methylpyrrolidine was replaced by pyrrolidine.

1H NMR (600 MHz, CHLOROFORM-d) δ ppm 1.72-1.82 (m, 4H), 2.02 (q, J=6.9 Hz, 2H), 2.19-2.28 (m, 2H), 2.47-2.66 (m, 8H), 3.76-3.84 (m, 2H), 4.06 (t, J=6.4 Hz, 2H), 6.96 (d, J=9.2 Hz, 2H), 7.58 (d, J=9.2 Hz, 2H), 7.65 (s, 1H), 8.44 (s, 1H)

MS (ESI/APCI Dual) (Positive) m/z; 355 (M+H)+

Example 33

Preparation of (1-{4-[3-(2-methylpyrrolidin-1-yl)propoxy]phenyl}-1H-pyrazol-4-yl)carbamic acid 2-chloroethyl ester

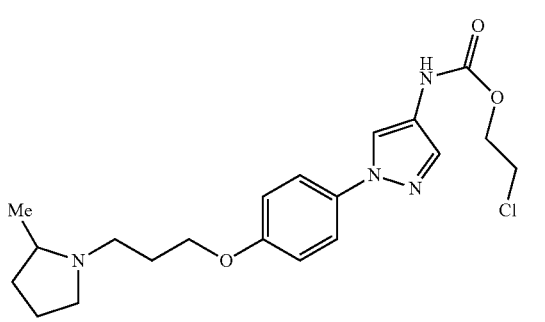

[Formula 74]

The same procedure as shown in Example 29-(2) was repeated to give the titled compound, except that 4-chlorobutyryl chloride was replaced by 2-chloroethyl chloroformate.

1H NMR (600 MHz, CHLOROFORM-d) δ ppm 1.91-2.38 (m, 7H), 2.49-3.51 (m, 4H), 3.67-3.97 (m, 4H), 4.02-4.16 (m, 2H), 4.36-4.51 (m, 3H), 6.70 (s, 1H), 6.87-6.97 (m, 2H), 7.51-7.61 (m, 3H), 8.09 (s, 1H)

MS (ESI/APCI Dual) (Positive) m/z; 407 (M+H)+

Example 34

Preparation of 3-(1-{4-[3-(2-methylpyrrolidin-1-yl)propoxy]phenyl}-1H-pyrazol-4-yl)-1,3-oxazolidin-2-one

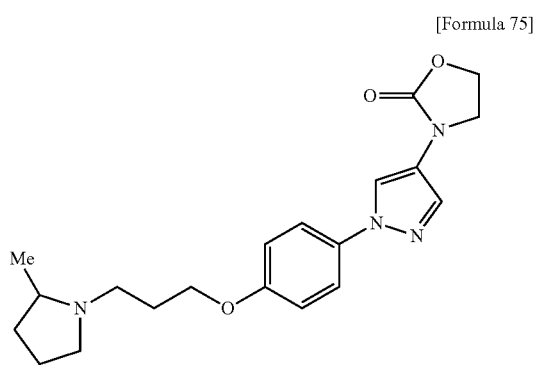

[Formula 75]

The same procedure as shown in Example 30 was repeated to give the titled compound, except that 4-chloro-N-[1-(4-{3-[(2R)-2-methylpyrrolidin-1-yl]propoxy}phenyl)-1H-pyrazol-4-yl]butylamide was replaced by (1-{4-[3-(2-methylpyrrolidin-1-yl)propoxy]phenyl}-1H-pyrazol-4-yl)carbamic acid 2-chloroethyl ester obtained in Example 33.

1H NMR (600 MHz, CHLOROFORM-d) δ ppm 1.08 (d, J=6.0 Hz, 3H), 1.37-1.45 (m, 1H), 1.64-1.82 (m, 2H), 1.87-2.05 (m, 3H), 2.11 (q, J=8.9 Hz, 1H), 2.16-2.23 (m, 1H), 2.25-2.32 (m, 1H), 2.94-3.01 (m, 1H), 3.14-3.20 (m, 1H), 3.97-4.08 (m, 4H), 4.52-4.57 (m, 2H), 6.93-6.98 (m, 2H), 7.54-7.57 (m, 2H), 7.59 (s, 1H), 8.18 (s, 1H)

MS (ESI/APCI Dual) (Positive) m/z; 371 (M+H)+

Example 35

Preparation of 5-chloropentanoyl acid (1-{4-[3-(2-methylpyrrolidin-1-yl)propoxy]phenyl}-1H-pyrazol-4-yl)amide

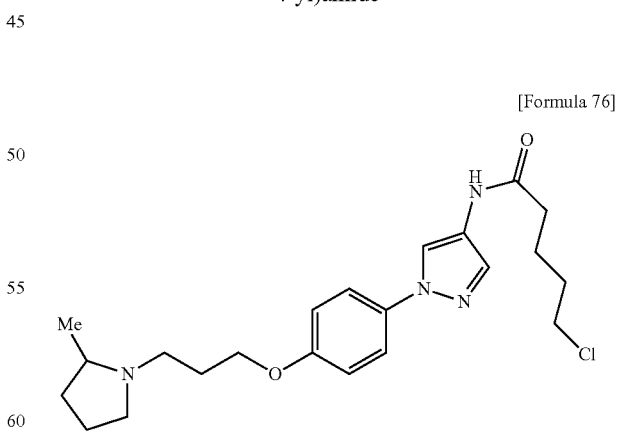

[Formula 76]

The same procedure as shown in Example 29-(2) was repeated to give the titled compound, except that 4-chlorobutyryl chloride was replaced by 5-chlorovaleryl chloride.

1H NMR (600 MHz, DMSO-d6) δ ppm 1.28-1.42 (m, 3H), 1.54-1.79 (m, 5H), 1.83-2.32 (m, 7H), 3.06 (br. s., 2H), 3.24-

3.48 (m, 2H), 3.54-3.68 (m, 3H), 4.04 (br. s., 2H), 7.01 (d, J=9.2 Hz, 2H), 7.60-7.74 (m, 3H), 8.39 (s, 1H), 10.09 (s, 1H)
MS (ESI) (Positive) m/z; 419 (M+H)⁺

Example 36

Preparation of 1-(1-{4-[3-(2-methylpyrrolidin-1-yl)propoxy]phenyl}-1H-pyrazol-4-yl)piperidin-2-one

[Formula 77]

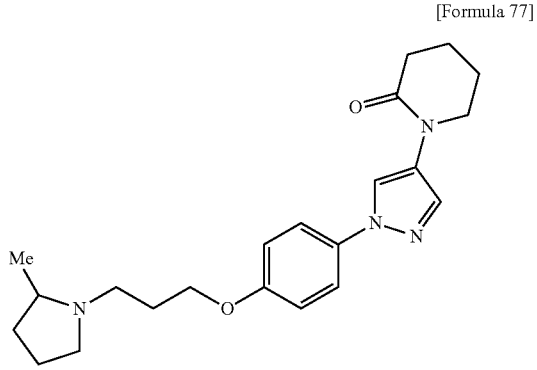

The same procedure as shown in Example 30 was repeated to give the titled compound, except that 4-chloro-N-[1-(4-{3-[(2R)-2-methylpyrrolidin-1-yl]propoxy}phenyl)-1H-pyrazol-4-yl]butylamide was replaced by 5-chloropentanoyl acid (1-{4-[3-(2-methylpyrrolidin-1-yl)propoxy]phenyl}-1H-pyrazol-4-yl)amide obtained in Example 35.

1H NMR (600 MHz, CHLOROFORM-d) δ ppm 1.08 (d, J=6.0 Hz, 3H), 1.36-1.45 (m, 1H), 1.63-1.82 (m, 2H), 1.85-2.05 (m, 7H), 2.10 (q, J=8.9 Hz, 1H), 2.16-2.22 (m, 1H), 2.24-2.32 (m, 1H), 2.58 (t, J=6.6 Hz, 2H), 2.94-3.01 (m, 1H), 3.14-3.20 (m, 1H), 3.72 (t, J=6.2 Hz, 2H), 4.00-4.08 (m, 2H), 6.95 (d, J=8.7 Hz, 2H), 7.54-7.59 (m, 2H), 7.70 (s, 1H), 8.49 (s, 1H)
MS (ESI/APCI Dual) (Positive) m/z; 383 (M+H)⁺

Example 37

Preparation of N-[1-(4-{3-[(2R)-2-methylpyrrolidin-1-yl]propoxy}phenyl)-1H-pyrazol-4-yl]acetamide

[Formula 78]

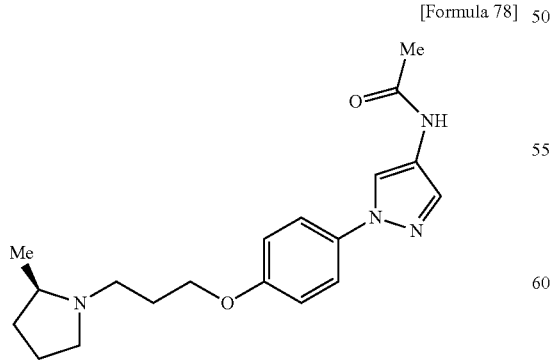

The same procedure as shown in Example 29-(2) was repeated to give the titled compound, except that 4-chlorobutyryl chloride was replaced by acetyl chloride.

1H NMR (600 MHz, CHLOROFORM-d) δ ppm 1.09 (d, J=6.0 Hz, 3H), 1.38-1.47 (m, 1H), 1.64-1.73 (m, 1H), 1.74-1.83 (m, 1H), 1.88-2.06 (m, 3H), 2.12 (q, J=8.9 Hz, 1H), 2.15-2.24 (m, 4H), 2.26-2.33 (m, 1H), 2.95-3.02 (m, 1H), 3.18 (td, J=8.6, 2.5 Hz, 1H), 4.01-4.09 (m, 2H), 6.96 (d, J=9.2 Hz, 2H), 7.18 (s, 1H), 7.55 (d, J=2.3 Hz, 2H), 7.57 (s, 1H), 8.37 (s, 1H)
MS (ESI/APCI Dual) (Positive) m/z; 343 (M+H)⁺

Example 38

Preparation of N-methyl-N-[1-(4-{3-[(2R)-2-methylpyrrolidin-1-yl]propoxy}phenyl)-1H-pyrazol-4-yl]acetamide

[Formula 79]

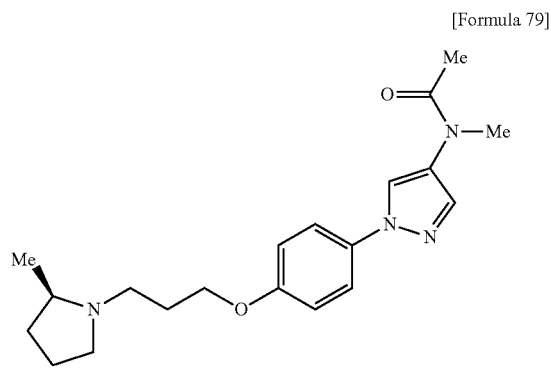

To a solution of N-[1-(4-{3-[(2R)-2-methylpyrrolidin-1-yl]propoxy}phenyl)-1H-pyrazol-4-yl]acetamide obtained in Example 37 (0.34 g) in tetrahydrofuran (3.5 mL), sodium hydride (55% in mineral oil, 0.048 g) was added and iodomethane (0.225 g) was then added dropwise under ice cooling, followed by stirring at room temperature for 1.5 hours. The reaction mixture was diluted with water and extracted with ethyl acetate. The organic layer was washed with water and brine, dried over sodium sulfate and concentrated under reduced pressure. The resulting residue was purified by NH-type silica gel column chromatography (eluting solvent: ethyl acetate:hexane=1:1→ethyl acetate), and the resulting crystal was washed with diisopropyl ether to give the titled compound (0.187 g) as a white solid.

1H NMR (600 MHz, CHLOROFORM-d) δ ppm 1.08 (d, J=6.0 Hz, 3H), 1.37-1.47 (m, 1H), 1.60-1.83 (m, 2H), 1.86-2.07 (m, 5H), 2.07-2.15 (m, 1H), 2.16-2.24 (m, 1H), 2.25-2.34 (m, 2H), 2.93-3.03 (m, 1H), 3.14-3.21 (m, 1H), 3.24 (s, 2H), 3.40 (s, 1H), 4.00-4.10 (m, 2H), 6.92-7.01 (m, 2H), 7.50-7.60 (m, 8/3H), 7.66 (s, ⅓H), 7.77 (s, ⅔H), 8.42 (s, ⅓H)
MS (ESI/APCI Dual) (Positive) m/z; 357 (M+H)⁺

Example 39

Preparation of N-ethyl-N-(1-{4-[3-(2-methylpyrrolidin-1-yl)propoxy]phenyl}-1H-pyrazol-4-yl)acetamide

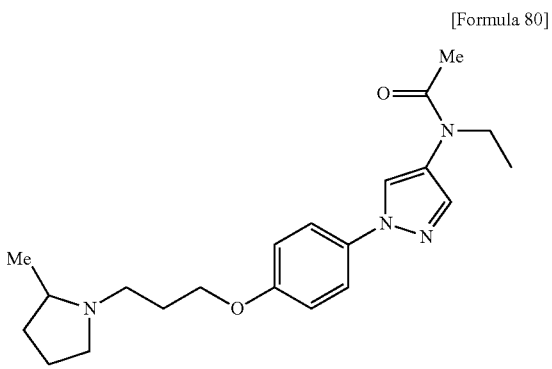

[Formula 80]

The same procedure as shown in Example 38 was repeated to give the titled compound, except that iodomethane was replaced by iodoethane.

1H NMR (600 MHz, CHLOROFORM-d) δ ppm 1.10 (d, J=6.0 Hz, 3H), 1.15 (t, J=7.1 Hz, 3H.⅝), 1.24-1.32 (m, 1H), 1.34 (t, J=7.3 Hz, 3H.⅛), 1.38-1.46 (m, 1H), 1.66-1.74 (m, 1H), 1.74-1.83 (m, 1H), 1.89-2.34 (m, 8H), 2.30 (s, 1H), 2.96-3.03 (m, 1H), 3.19 (td, J=8.6, 2.5 Hz, 1H), 3.69 (q, J=6.9 Hz, 2H.⅝), 3.78 (q, J=7.0 Hz, 2H.⅛), 4.03-4.11 (m, 2H), 6.95-7.01 (m, 2H), 7.54-7.65 (m, 3H), 7.77 (s, 1H.⅝), 8.41 (s, 1H.⅛)

MS (ESI/APCI Dual) (Positive) m/z; 371 (M+H)+

Example 40

Preparation of 4-cyano-N-(1-{4-[3-(2-methylpyrrolidin-1-yl)propoxy]phenyl}-1H-pyrazol-4-yl)benzamide

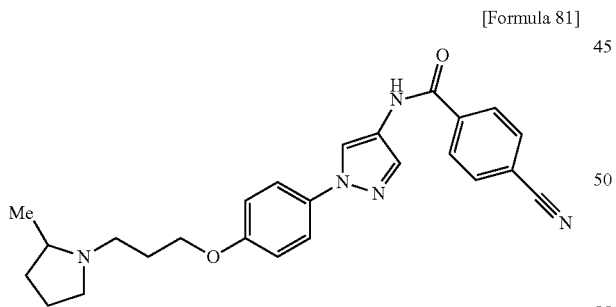

[Formula 81]

The same procedure as shown in Example 29-(2) was repeated to give the titled compound, except that 4-chlorobutyryl chloride was replaced by 4-cyanobenzoyl chloride.

1H NMR (600 MHz, CHLOROFORM-d) δ ppm 1.10 (d, J=6.0 Hz, 3H), 1.38-1.47 (m, 1H), 1.66-1.74 (m, 1H), 1.74-1.83 (m, 1H), 1.89-2.06 (m, 3H), 2.12 (q, J=8.7 Hz, 1H), 2.19-2.24 (m, 1H), 2.27-2.33 (m, 1H), 2.96-3.02 (m, 1H), 3.18 (td, J=8.7, 2.8 Hz, 1H), 4.03-4.11 (m, 2H), 6.99 (d, J=9.2 Hz, 2H), 7.60 (d, J=9.2 Hz, 2H), 7.72 (s, 1H), 7.81 (d, J=8.3 Hz, 2H), 7.92 (s, 1H), 7.99 (d, J=8.7 Hz, 2H), 8.55 (s, 1H)

MS (ESI/APCI Dual) (Positive) m/z; 430 (M+H)+

Example 41

Preparation of 4-methoxy-N-(1-{4-[3-(2-methylpyrrolidin-1-yl)propoxy]phenyl}-1H-pyrazol-4-yl)benzamide

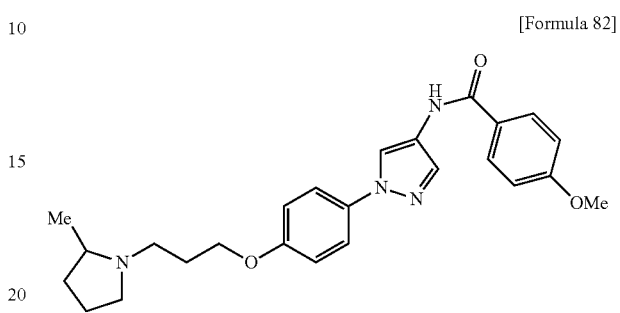

[Formula 82]

The same procedure as shown in Example 29-(2) was repeated to give the titled compound, except that 4-chlorobutyryl chloride was replaced by 4-methoxybenzoyl chloride.

1H NMR (600 MHz, CHLOROFORM-d) δ ppm 1.10 (d, J=6.0 Hz, 3H), 1.39-1.46 (m, 1H), 1.65-1.82 (m, 2H), 1.89-2.06 (m, 3H), 2.12 (q, J=8.7 Hz, 1H), 2.18-2.24 (m, 1H), 2.27-2.33 (m, 1H), 2.96-3.02 (m, 1H), 3.19 (td, J=8.6, 2.5 Hz, 1H), 3.88 (s, 3H), 4.03-4.10 (m, 2H), 6.96-7.01 (m, 4H), 7.60 (d, J=9.2 Hz, 2H), 7.69 (s, 1H), 7.74 (s, 1H), 7.85 (d, J=8.7 Hz, 2H), 8.55 (s, 1H)

MS (ESI/APCI Dual) (Positive) m/z; 435 (M+H)+

Example 42

Preparation of 4-hydroxy-N-[1-(4-{3-[(2R)-2-methylpyrrolidin-1-yl]propoxy}phenyl)-1H-pyrazol-4-yl]benzamide

[Formula 83]

A suspension of 1-(4-{3-[(2R)-2-methylpyrrolidin-1-yl]propoxy}phenyl)-1H-pyrazol-4-ylamine obtained in Example 29-(1) (0.191 g), 4-hydroxybenzoic acid (0.097 g), 1-hydroxybenzotriazole monohydrate (0.107 g) and 3-(3-dimethylaminopropyl)-1-ethylcarbodiimide hydrochloride (0.18 g) in chloroform (6.4 mL) was stirred at room temperature for 4 days. The reaction mixture was concentrated under reduced pressure, and the residue was purified by NH-type silica gel column chromatography (eluting solvent:

chloroform→chloroform:methanol=10:1) to give the titled compound (0.137 g) as a colorless amorphous substance.

1H NMR (600 MHz, DMSO-$d_6$) δ ppm 1.00 (d, J=6.0 Hz, 3H), 1.24-1.32 (m, 1H), 1.58-1.70 (m, 2H), 1.80-1.95 (m, 3H), 2.04 (q, J=8.7 Hz, 1H), 2.09-2.15 (m, 1H), 2.20-2.29 (m, 1H), 2.87-2.96 (m, 1H), 3.08 (td, J=8.4, 3.0 Hz, 1H), 4.05 (t, J=6.2 Hz, 2H), 6.87 (d, J=8.7 Hz, 2H), 7.03 (d, J=8.7 Hz, 2H), 7.68 (d, J=9.2 Hz, 2H), 7.83 (s, 1H), 7.86 (d, J=8.7 Hz, 2H), 8.53 (s, 1H), 10.14 (br. s., 1H), 10.32 (s, 1H)

MS (ESI/APCI Dual) (Positive) m/z; 421 (M+H)$^+$

Example 43

Preparation of N-[1-(4-{3-[(2R)-2-methylpyrrolidin-1-yl]propoxy}phenyl)-1H-pyrazol-4-yl]pyridine-3-carboxamide

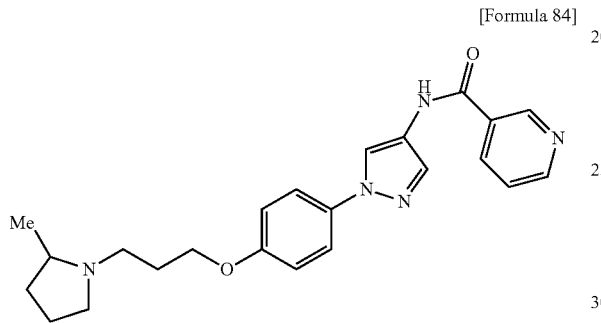

[Formula 84]

The same procedure as shown in Example 29-(2) was repeated to give the titled compound, except that 4-chlorobutyryl chloride was replaced by nicotinoyl chloride hydrochloride.

1H NMR (600 MHz, CHLOROFORM-d) δ ppm 1.09 (d, J=6.0 Hz, 3H), 1.37-1.47 (m, 1H), 1.65-1.83 (m, 2H), 1.87-2.06 (m, 3H), 2.11 (q, J=9.0 Hz, 1H), 2.17-2.24 (m, 1H), 2.25-2.33 (m, 1H), 2.94-3.02 (m, 1H), 3.14-3.21 (m, 1H), 4.02-4.10 (m, 2H), 6.95-7.00 (m, 2H), 7.43-7.48 (m, 1H), 7.56-7.62 (m, 2H), 7.73 (s, 1H), 7.96 (s, 1H), 8.19-8.23 (m, 1H), 8.54 (s, 1H), 8.76-8.80 (m, 1H), 9.08-9.12 (m, 1H)

MS (ESI/APCI Dual) (Positive) m/z; 406 (M+H)$^+$

Example 44

Preparation of N-[1-(4-{3-[(2R)-2-methylpyrrolidin-1-yl]propoxy}phenyl)-1H-pyrazol-4-yl]pyridine-4-carboxamide

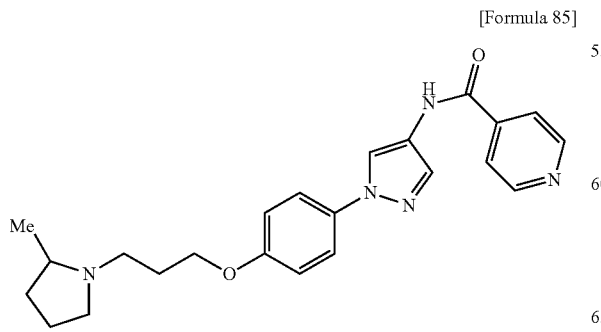

[Formula 85]

The same procedure as shown in Example 29-(2) was repeated to give the titled compound, except that 4-chlorobutyryl chloride was replaced by isonicotinoyl chloride hydrochloride.

1H NMR (600 MHz, CHLOROFORM-d) δ ppm 1.09 (d, J=6.4 Hz, 3H), 1.38-1.46 (m, 1H), 1.65-1.82 (m, 2H), 1.87-2.06 (m, 3H), 2.11 (q, J=8.7 Hz, 1H), 2.17-2.23 (m, 1H), 2.26-2.33 (m, 1H), 2.95-3.01 (m, 1H), 3.15-3.20 (m, 1H), 4.02-4.09 (m, 2H), 6.95-6.99 (m, 2H), 7.56-7.60 (m, 2H), 7.71 (d, J=4.6 Hz, 3H), 8.02 (s, 1H), 8.54 (s, 1H), 8.77-8.84 (m, 2H)

MS (ESI/APCI Dual) (Positive) m/z; 406 (M+H)$^+$

Example 45

Preparation of 2-(4-hydroxyphenyl)-N-[1-(4-{3-[(2R)-2-methylpyrrolidin-1-yl]propoxy}phenyl)-1H-pyrazol-4-yl]acetamide

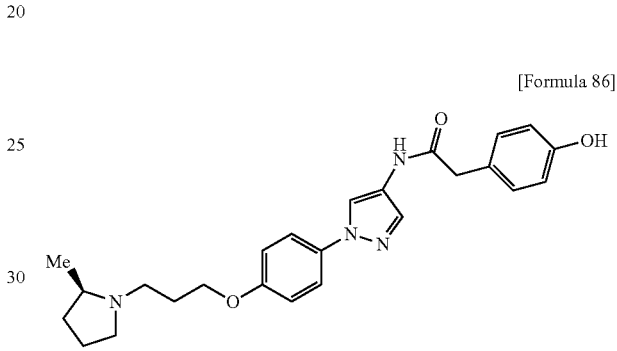

[Formula 86]

The same procedure as shown in Example 42 was repeated to give the titled compound, except that 4-hydroxybenzoic acid was replaced by 4-hydroxyphenylacetic acid.

1H NMR (600 MHz, CHLOROFORM-d) δ ppm 1.11 (d, J=6.0 Hz, 3H), 1.44 (dddd, J=17.0, 4.0, 2.5, 2.2 Hz, 1H), 1.66-1.75 (m, 1H), 1.75-1.84 (m, 1H), 1.88-2.03 (m, 3H), 2.11-2.25 (m, 2H), 2.29-2.38 (m, 1H), 2.97-3.05 (m, 1H), 3.15-3.21 (m, 1H), 3.63 (s, 2H), 4.02 (t, J=6.9 Hz, 2H), 6.77-6.82 (m, 2H), 6.86-6.92 (m, 2H), 7.12 (d, J=8.7 Hz, 2H), 7.34 (s, 1H), 7.43-7.51 (m, 3H), 8.32 (s, 1H)

MS (ESI/APCI Dual) (Positive) m/z; 435 (M+H)$^+$

Example 46

Preparation of N-[1-(4-{3-[(2R)-2-methylpyrrolidin-1-yl]propoxy}phenyl)-1H-pyrazol-4-yl]-2-(pyridin-3-yl)acetamide

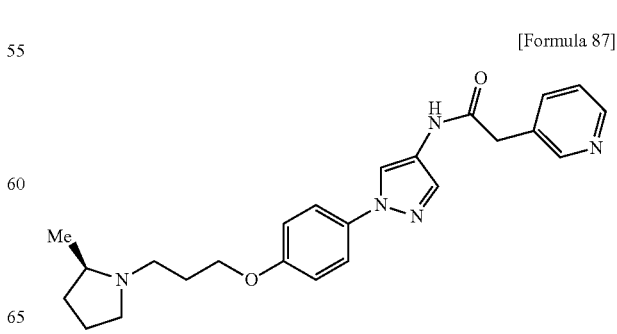

[Formula 87]

The same procedure as shown in Example 42 was repeated to give the titled compound, except that 4-hydroxybenzoic acid was replaced by 3-pyridylacetic acid.

1H NMR (600 MHz, CHLOROFORM-d) δ ppm 1.08 (d, J=6.0 Hz, 3H), 1.36-1.46 (m, 1H), 1.63-1.82 (m, 2H), 1.86-2.05 (m, 3H), 2.10 (q, J=9.2 Hz, 1H), 2.15-2.22 (m, 1H), 2.24-2.33 (m, 1H), 2.92-3.02 (m, 1H), 3.13-3.20 (m, 1H), 3.72 (s, 2H), 3.99-4.08 (m, 2H), 6.91-6.98 (m, 2H), 7.30-7.41 (m, 2H), 7.49-7.57 (m, 3H), 7.72 (d, J=7.8 Hz, 1H), 8.36 (s, 1H), 8.53-8.61 (m, 2H)

MS (ESI/APCI Dual) (Positive) m/z; 420 (M+H)+

Example 47

Preparation of N-[1-(4-{3-[(2R)-2-methylpyrrolidin-1-yl]propoxy}phenyl)-1H-pyrazol-4-yl]-2-(pyridin-4-yl)acetamide

[Formula 88]

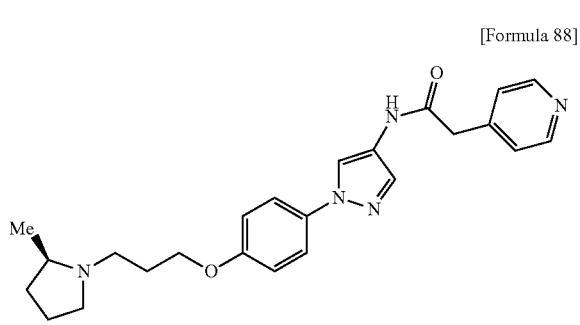

The same procedure as shown in Example 42 was repeated to give the titled compound, except that 4-hydroxybenzoic acid was replaced by 4-pyridylacetic acid.

1H NMR (600 MHz, CHLOROFORM-d) δ ppm 1.08 (d, J=6.0 Hz, 3H), 1.37-1.45 (m, 1H), 1.65-1.72 (m, 1H), 1.72-1.81 (m, 1H), 1.86-2.04 (m, 3H), 2.10 (q, J=8.7 Hz, 1H), 2.15-2.22 (m, 1H), 2.24-2.32 (m, 1H), 2.93-3.00 (m, 1H), 3.13-3.19 (m, 1H), 3.71 (s, 2H), 3.99-4.07 (m, 2H), 6.91-6.96 (m, 2H), 7.28 (d, J=6.0 Hz, 2H), 7.39 (s, 1H), 7.50-7.55 (m, 3H), 8.36 (s, 1H), 8.59-8.62 (m, 2H)

MS (ESI/APCI Dual) (Positive) m/z; 420 (M+H)+

Example 48

Preparation of N-[1-(4-{3-[(2R)-2-methylpyrrolidin-1-yl]propoxy}phenyl)-1H-pyrazol-4-yl]methanesulfonamide

[Formula 89]

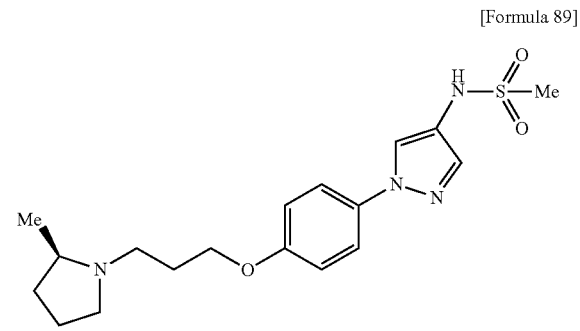

The same procedure as shown in Example 29-(2) was repeated to give the titled compound, except that 4-chlorobutyryl chloride was replaced by methanesulfonyl chloride.

1H NMR (600 MHz, CHLOROFORM-d) δ ppm 1.09 (d, J=6.4 Hz, 3H), 1.38-1.47 (m, 1H), 1.64-1.83 (m, 2H), 1.87-2.06 (m, 3H), 2.07-2.34 (m, 3H), 2.95-3.02 (m, 4H), 3.14-3.21 (m, 1H), 4.02-4.08 (m, 2H), 6.94-6.98 (m, 2H), 7.51-7.55 (m, 2H), 7.59-7.61 (m, 1H), 7.92-7.94 (m, 1H)

MS (ESI/APCI Dual) (Positive) m/z; 379 (M+H)+

Example 49

Preparation of N-methyl-N-[1-(4-{3-[(2R)-2-methylpyrrolidin-1-yl]propoxy}phenyl)-1H-pyrazol-4-yl]methanesulfonamide

[Formula 90]

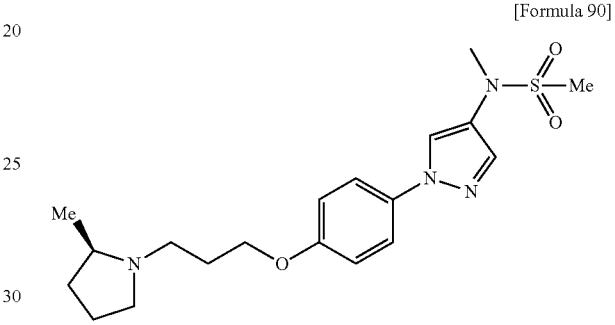

The same procedure as shown in Example 38 was repeated to give the titled compound, except that N-[1-(4-{3-[(2R)-2-methylpyrrolidin-1-yl]propoxy}phenyl)-1H-pyrazol-4-yl]acetamide was replaced by N-[1-(4-{3-[(2R)-2-methylpyrrolidin-1-yl]propoxy}phenyl)-1H-pyrazol-4-yl]methanesulfonamide obtained in Example 48.

1H NMR (600 MHz, CHLOROFORM-d) δ ppm 1.08 (d, J=6.0 Hz, 3H), 1.37-1.45 (m, 1H), 1.64-1.82 (m, 2H), 1.87-2.03 (m, 3H), 2.11 (q, J=9.0 Hz, 1H), 2.17-2.23 (m, 1H), 2.25-2.33 (m, 1H), 2.83 (s, 3H), 2.94-3.01 (m, 1H), 3.14-3.20 (m, 1H), 3.30 (s, 3H), 4.01-4.09 (m, 2H), 6.94-6.99 (m, 2H), 7.51-7.56 (m, 2H), 7.65 (s, 1H), 7.91 (s, 1H)

MS (ESI/APCI Dual) (Positive) m/z; 393 (M+H)+

Example 50

Preparation of 4-cyano-N-(1-{4-[3-(2-methylpyrrolidin-1-yl)propoxy]phenyl}-1H-pyrazol-4-yl)benzenesulfonamide

[Formula 91]

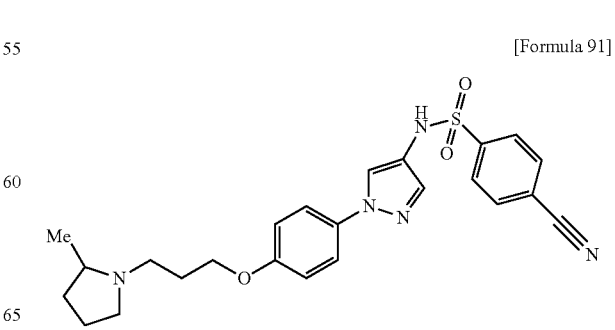

The same procedure as shown in Example 29-(2) was repeated to give the titled compound, except that 4-chlorobutyryl chloride was replaced by 4-cyanobenzenesulfonyl chloride.

1H NMR (600 MHz, CHLOROFORM-d) δ ppm 1.17 (d, J=6.0 Hz, 3H), 1.49-1.57 (m, 1H), 1.73-1.81 (m, 1H), 1.84-1.93 (m, 1H), 1.96-2.12 (m, 3H), 2.31-2.41 (m, 2H), 2.50-2.58 (m, 1H), 3.02-3.09 (m, 1H), 3.31 (td, J=8.9, 3.2 Hz, 1H), 4.00 (t, J=6.4 Hz, 2H), 5.55 (br. s., 1H), 6.88 (d, J=8.7 Hz, 2H), 7.31 (s, 1H), 7.43 (d, J=9.2 Hz, 2H), 7.72 (d, J=8.7 Hz, 2H), 7.76 (s, 1H), 7.88 (d, J=8.7 Hz, 2H)

MS (ESI/APCI Dual) (Positive) m/z; 466 (M+H)+

Example 51

Preparation of N-[1-(4-{3-[(2R)-2-methylpyrrolidin-1-yl]propoxy}phenyl)-1H-pyrazol-4-yl]pyridine-3-sulfonamide

[Formula 92]

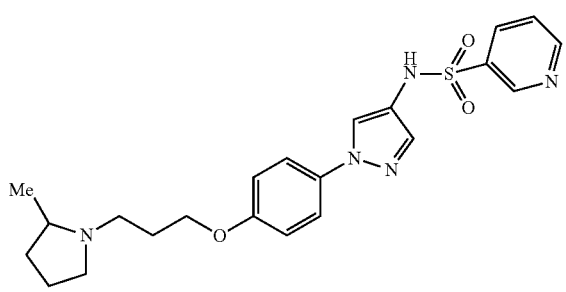

The same procedure as shown in Example 29-(2) was repeated to give the titled compound, except that 4-chlorobutyryl chloride was replaced by pyridine-3-sulfonyl chloride.

1H NMR (600 MHz, CHLOROFORM-d) δ ppm 1.10 (d, J=6.0 Hz, 3H), 1.40-1.48 (m, 1H), 1.67-1.74 (m, 1H), 1.76-1.85 (m, 1H), 1.89-2.06 (m, 3H), 2.16 (q, J=8.7 Hz, 1H), 2.20-2.27 (m, 1H), 2.31-2.38 (m, 1H), 2.99 (dd, J=8.3, 4.1 Hz, 1H), 3.17-3.23 (m, 1H), 3.99-4.06 (m, 2H), 6.90-6.95 (m, 2H), 7.32 (s, 1H), 7.41 (dd, J=8.0, 4.8 Hz, 1H), 7.44-7.48 (m, 2H), 7.80 (s, 1H), 8.00-8.04 (m, 1H), 8.76-8.79 (m, 1H), 9.01 (d, J=1.8 Hz, 1H)

MS (ESI/APCI Dual) (Positive) m/z; 442 (M+H)+

Example 52

Preparation of 1-(1-{4-[3-(2-methylpyrrolidin-1-yl)propoxy]phenyl}-1H-pyrazol-4-yl)pyrrolidine-2,5-dione

[Formula 93]

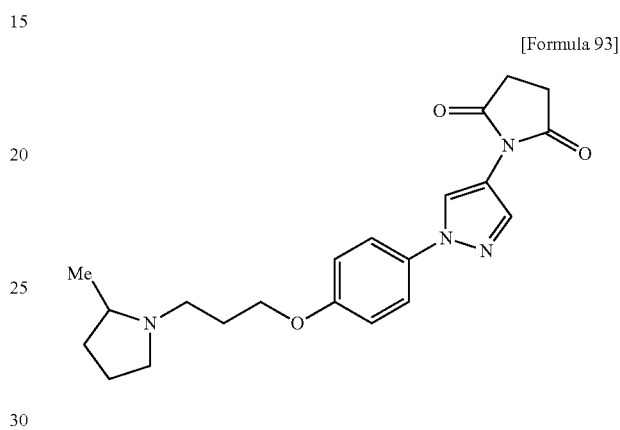

A solution of 1-{4-[3-(2-methylpyrrolidin-1-yl)propoxy]phenyl}-1H-pyrazol-4-ylamine obtained in the same manner as shown in Example 29-(1) (0.186 g) and succinic anhydride (0.074 g) in toluene (12 mL) was stirred under heating at reflux for 4 hours. The reaction mixture was cooled in an ice bath, and the precipitated crystal was collected by filtration and washed with toluene to give N-(1-{4-[3-(2-methylpyrrolidin-1-yl)propoxy]phenyl}-1H-pyrazol-4-yl)succinamic acid (0.191 g) as a colorless powder. A suspension of N-(1-{4-[3-(2-methylpyrrolidin-1-yl)propoxy]phenyl}-1H-pyrazol-4-yl)succinamic acid thus obtained (0.108 g) in acetic anhydride (5.4 mL) was stirred under heating at reflux for 30 minutes. The reaction mixture was cooled to room temperature, diluted with saturated aqueous sodium bicarbonate and extracted with chloroform. The organic layer was dried over sodium sulfate and concentrated under reduced pressure, and the resulting residue was purified by NH-type silica gel column chromatography (eluting solvent: hexane:ethyl acetate=1:1). The resulting solid was washed with diisopropyl ether to give the titled compound (0.044 g) as a colorless powder.

1H NMR (600 MHz, CHLOROFORM-d) δ ppm 1.10 (d, J=6.4 Hz, 3H), 1.38-1.47 (m, 1H), 1.65-1.73 (m, 1H), 1.74-1.83 (m, 1H), 1.88-2.06 (m, 3H), 2.12 (q, J=8.7 Hz, 1H), 2.17-2.24 (m, 1H), 2.26-2.34 (m, 1H), 2.89 (s, 4H), 2.95-3.03 (m, 1H), 3.18 (td, J=8.7, 2.8 Hz, 1H), 4.03-4.10 (m, 2H), 6.98 (d, J=8.7 Hz, 2H), 7.60 (d, J=8.7 Hz, 2H), 8.32 (s, 1H), 8.53 (s, 1H)

MS (ESI/APCI Dual) (Positive) m/z; 383 (M+H)+

Example 53

Preparation of (2,6-dimethylmorpholin-4-yl)[1-(4-{3-[(2R)-2-methylpyrrolidin-1-yl]propoxy}phenyl)-1H-pyrazol-4-yl]methanone

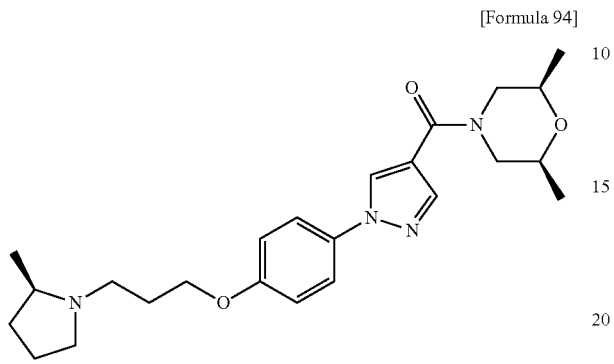

[Formula 94]

The same procedure as shown in Example 2-(2) was repeated to give the titled compound, except that aqueous ammonia was replaced by cis-2,6-dimethylmorpholine.

1H NMR (600 MHz, CHLOROFORM-d) δ ppm 1.09 (d, J=6.0 Hz, 3H), 1.22 (br. s., 6H), 1.38-1.46 (m, 1H), 1.63-1.84 (m, 3H), 1.87-2.06 (m, 3H), 2.12 (q, J=8.9 Hz, 1H), 2.17-2.25 (m, 1H), 2.25-2.34 (m, 1H), 2.55 (br. s., 1H), 2.81-3.05 (m, 2H), 3.18 (td, J=8.7, 2.8 Hz, 1H), 3.62 (br. s., 2H), 4.00-4.11 (m, 2H), 4.53 (br. s., 1H), 6.99 (d, J=8.7 Hz, 2H), 7.57 (d, J=8.7 Hz, 2H), 7.77 (s, 1H), 8.13 (s, 1H)

MS (ESI/APCI Dual) (Positive) m/z; 427 (M+H)$^+$

Example 54

Preparation of [1-(4-{3-[(2R)-2-methylpyrrolidin-1-yl]propoxy}phenyl)-1H-pyrazol-4-yl](1,4-oxazepan-4-yl)methanone

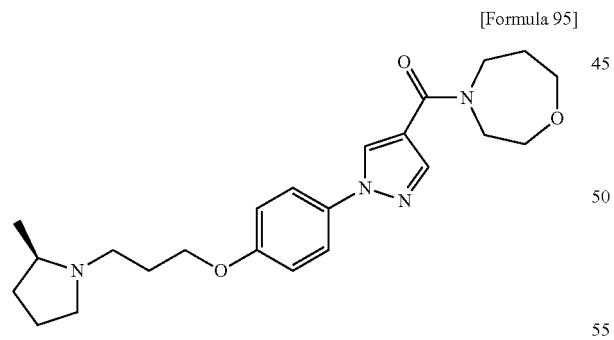

[Formula 95]

The same procedure as shown in Example 2-(2) was repeated to give the titled compound, except that aqueous ammonia was replaced by homomorpholine.

1H NMR (600 MHz, CHLOROFORM-d) δ ppm 1.09 (d, J=6.0 Hz, 3H), 1.37-1.47 (m, 1H), 1.65-1.73 (m, 1H), 1.73-1.83 (m, 1H), 1.87-1.95 (m, 1H), 1.96-2.06 (m, 4H), 2.07-2.15 (m, 1H), 2.16-2.24 (m, 1H), 2.25-2.33 (m, 1H), 2.95-3.02 (m, 1H), 3.14-3.21 (m, 1H), 3.76-3.89 (m, 8H), 4.02-4.09 (m, 2H), 6.98 (d, J=9.2 Hz, 2H), 7.56 (d, J=8.7 Hz, 2H), 7.75-7.86 (m, 1H), 8.13-8.21 (m, 1H)

MS (ESI/APCI Dual) (Positive) m/z; 413 (M+H)$^+$

Example 55

Preparation of (4-methylpiperazin-1-yl)[1-(4-{3-[(2R)-2-methylpyrrolidin-1-yl]propoxy}phenyl)-1H-pyrazol-4-yl]methanone

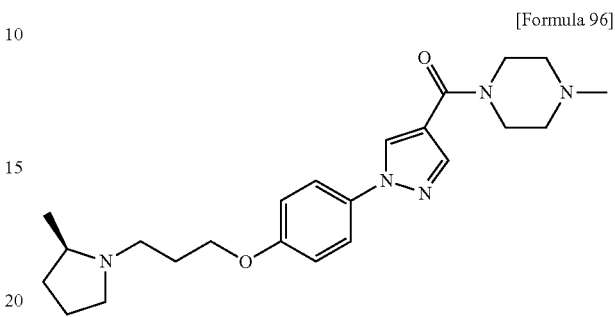

[Formula 96]

The same procedure as shown in Example 2-(2) was repeated to give the titled compound, except that aqueous ammonia was replaced by 4-methylpiperazine.

1H NMR (600 MHz, CHLOROFORM-d) δ ppm 1.10 (d, J=6.0 Hz, 3H), 1.37-1.48 (m, 1H), 1.62-2.07 (m, 5H), 2.08-2.16 (m, 1H), 2.17-2.25 (m, 1H), 2.26-2.37 (m, 4H), 2.46 (br. s., 4H), 2.95-3.03 (m, 1H), 3.15-3.22 (m, 1H), 3.78 (br. s., 4H), 4.02-4.11 (m, 2H), 6.98 (d, J=9.2 Hz, 2H), 7.57 (d, J=8.7 Hz, 2H), 7.79 (s, 1H), 8.13 (s, 1H)

MS (ESI/APCI Dual) (Positive) m/z; 412 (M+H)$^+$

Example 56

Preparation of [1-(4-{3-[(2R)-2-methylpyrrolidin-1-yl]propoxy}phenyl)-1H-pyrazol-4-yl](pyrrolidin-1-yl)methanone

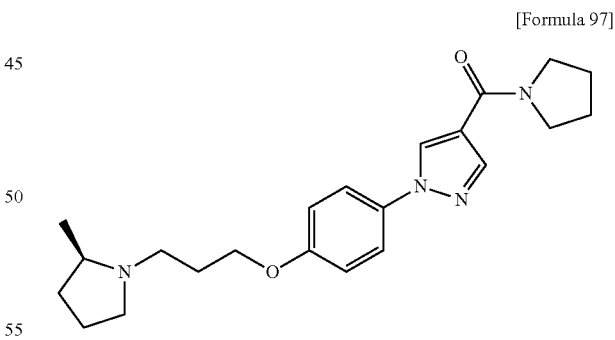

[Formula 97]

The same procedure as shown in Example 2-(2) was repeated to give the titled compound, except that aqueous ammonia was replaced by pyrrolidine.

1H NMR (600 MHz, CHLOROFORM-d) δ ppm 1.10 (d, J=6.0 Hz, 3H), 1.38-1.47 (m, 1H), 1.64-2.07 (m, 9H), 2.09-2.15 (m, 1H), 2.17-2.24 (m, 1H), 2.26-2.34 (m, 1H), 2.95-3.03 (m, 1H), 3.15-3.22 (m, 1H), 3.66 (t, J=6.9 Hz, 2H), 3.75 (t, J=6.6 Hz, 2H), 4.02-4.11 (m, 2H), 6.96-7.01 (m, 2H), 7.56-7.61 (m, 2H), 7.96 (s, 1H), 8.28 (s, 1H)

MS (ESI/APCI Dual) (Positive) m/z; 383 (M+H)$^+$

Example 57

Preparation of (1-{4-[3-(3-methylpyrrolidin-1-yl)propoxy]phenyl}-1H-pyrazol-4-yl)(morpholin-4-yl)methanone

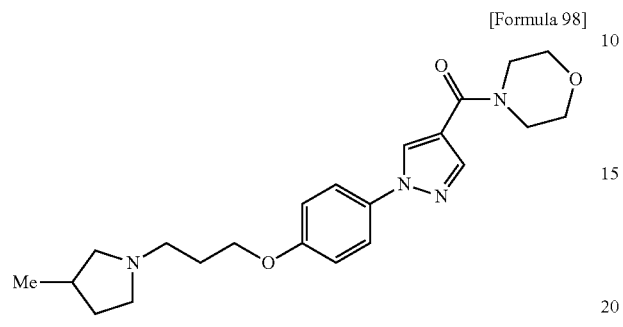

[Formula 98]

The same procedures as shown in Example 1-(2) and Example 6-(2) were repeated to give the titled compound, except that (R)-2-methylpyrrolidine was replaced by 3-methylpyrrolidine.

1H NMR (600 MHz, CHLOROFORM-d) δ ppm 1.04 (d, J=6.9 Hz, 3H), 1.31-1.40 (m, 1H), 1.97-2.07 (m, 4H), 2.22-2.31 (m, 1H), 2.44-2.50 (m, 1H), 2.55-2.61 (m, 1H), 2.62-2.68 (m, 1H), 2.69-2.76 (m, 1H), 2.83-2.89 (m, 1H), 3.71-3.81 (m, 8H), 4.06 (t, J=6.4 Hz, 2H), 6.95-7.01 (m, 2H), 7.53-7.59 (m, 2H), 7.78 (s, 1H), 8.14 (s, 1H)

MS (ESI/APCI Dual) (Positive) m/z; 399 (M+H)+

Example 58

Preparation of (1-{4-[3-(2-ethylpyrrolidin-1-yl)propoxy]phenyl}-1H-pyrazol-4-yl)(morpholin-4-yl)methanone

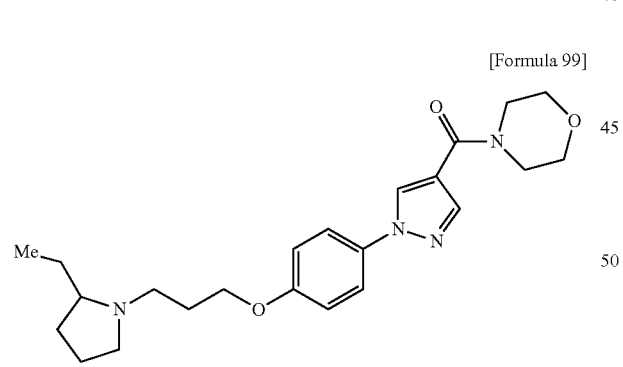

[Formula 99]

The same procedures as shown in Example 1-(2) and Example 6-(2) were repeated to give the titled compound, except that (R)-2-methylpyrrolidine was replaced by 2-ethylpyrrolidine.

1H NMR (600 MHz, CHLOROFORM-d) δ ppm 0.87 (t, J=7.3 Hz, 3H), 1.16-1.29 (m, 1H), 1.39-1.49 (m, 1H), 1.67-1.82 (m, 3H), 1.87-1.95 (m, 1H), 1.95-2.06 (m, 2H), 2.08-2.14 (m, 1H), 2.13-2.19 (m, 1H), 2.19-2.27 (m, 1H), 2.90-3.07 (m, 1H), 3.11-3.26 (m, 1H), 3.68-3.85 (m, 8H), 3.93-4.13 (m, 2H), 6.93-7.05 (m, 2H), 7.49-7.61 (m, 2H), 7.78 (s, 1H), 8.14 (s, 1H)

MS (ESI/APCI Dual) (Positive) m/z; 413 (M+H)+

Example 59

Preparation of (1-{4-[3-(2,2-difluoropyrrolidin-1-yl)propoxy]phenyl}-1H-pyrazol-4-yl)(morpholin-4-yl)methanone

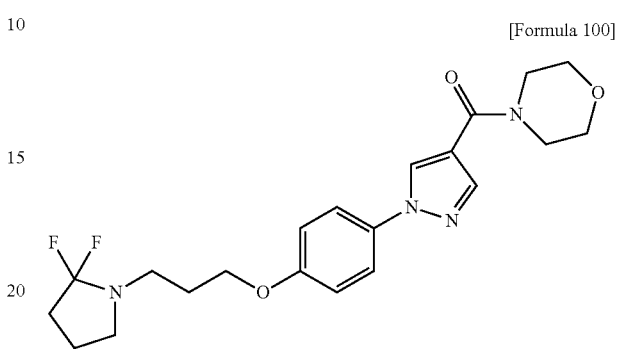

[Formula 100]

The same procedures as shown in Example 1-(2) and Example 6-(2) were repeated to give the titled compound, except that (R)-2-methylpyrrolidine was replaced by 2,2-difluoropyrrolidine.

1H NMR (600 MHz, CHLOROFORM-d) δ ppm 1.94-2.03 (m, 2H), 2.23-2.34 (m, 2H), 2.66 (t, J=7.1 Hz, 2H), 2.76 (t, J=7.1 Hz, 2H), 2.93 (t, J=13.3 Hz, 2H), 3.68-3.83 (m, 8H), 4.07 (t, J=6.2 Hz, 2H), 6.94-7.02 (m, 2H), 7.54-7.60 (m, 2H), 7.79 (s, 1H), 8.15 (s, 1H)

MS (ESI/APCI Dual) (Positive) m/z; 421 (M+H)+

Example 60

Preparation of [1-(4-{2-[(2R)-2-methylpyrrolidin-1-yl]ethoxy}phenyl)-1H-pyrazol-4-yl](morpholin-4-yl)methanone (1) Preparation of 1-(2-chloroethoxy)-4-iodobenzene

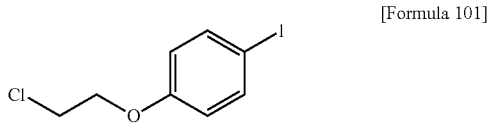

[Formula 101]

To a solution of 4-iodophenol (1.0 g) in acetonitrile (10 mL), cesium carbonate (3.0 g) and 1-bromo-2-chloroethane (0.8 g) were added and the mixture was heated to 100° C., at which it was stirred for 4 hours. Additional 1-bromo-2-chloroethane (1.0 g) was further added and stirred at 100° C. for 4 hours. The reaction mixture was cooled to room temperature and filtered to remove insoluble materials, and the filtrate was concentrated under reduced pressure. The resulting residue was purified by NH-type silica gel column chromatography (eluting solvent: n-hexane:ethyl acetate=11:1) to give the titled compound (0.87 g, 68%) as a yellow oil.

(2) Preparation of (2R)-1-[2-(4-iodophenoxy)ethyl]-2-methylpyrrolidine

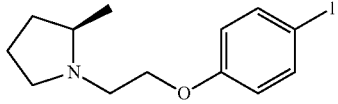

[Formula 102]

To a suspension of (2R)-2-methylpyrrolidine (0.60 g) and cesium carbonate (1.2 g) in acetonitrile (3 mL), 1-(2-chloroethoxy)-4-iodobenzene obtained in Example 60-(1) (0.87 g) was added and the mixture was heated to 100° C., at which it was stirred for 9 hours. The reaction mixture was cooled to room temperature and filtered to remove insoluble materials, and the filtrate was concentrated under reduced pressure. The resulting residue was purified by NH-type silica gel column chromatography (eluting solvent: n-hexane:ethyl acetate=9:1 to 1:1) to give the titled compound (0.80 g, 78%) as a colorless oil.

(3) Preparation of [1-(4-{2-[(2R)-2-methylpyrrolidin-1-yl]ethoxy}phenyl)-1H-pyrazol-4-yl](morpholin-4-yl)methanone

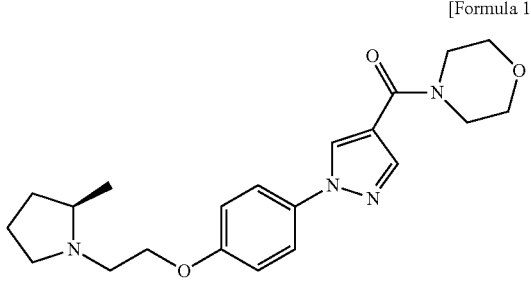

[Formula 103]

The same procedure as shown in Example 6 was repeated to give the titled compound, except that (2R)-1-[3-(4-iodophenoxy)propyl]-2-methylpyrrolidine was replaced by (2R)-1-[2-(4-iodophenoxy)ethyl]-2-methylpyrrolidine obtained in Example 60-(2).

1H NMR (600 MHz, CHLOROFORM-d) δ ppm 1.15 (d, J=6.0 Hz, 3H), 1.41-1.51 (m, 1H), 1.69-1.77 (m, 1H), 1.78-1.88 (m, 1H), 1.90-1.98 (m, 1H), 2.25-2.33 (m, 1H), 2.39-2.46 (m, 1H), 2.52-2.60 (m, 1H), 3.18-3.30 (m, 2H), 3.70-3.81 (m, 8H), 4.09-4.19 (m, 2H), 6.97-7.03 (m, 2H), 7.54-7.60 (m, 2H), 7.79 (s, 1H), 8.14 (s, 1H)

MS (ESI/APCI Dual) (Positive) m/z; 385 (M+H)+

Example 61

Preparation of [1-(4-{4-[(2R)-2-methylpyrrolidin-1-yl]butoxy}phenyl)-1H-pyrazol-4-yl](morpholin-4-yl)methanone

(1) Preparation of 1-(4-chlorobutoxy)-4-iodobenzene

[Formula 104]

To a solution of 4-iodophenol (1.0 g) in acetonitrile (10 mL), cesium carbonate (3.0 g) and 1-chloro-4-iodobutane (1.2 g) were added and the mixture was heated to 100° C., at which it was stirred for 4 hours. The reaction mixture was cooled to room temperature and filtered to remove insoluble materials, and the filtrate was concentrated under reduced pressure. The resulting residue was purified by NH-type silica gel column chromatography (eluting solvent: n-hexane:ethyl acetate=7:3 to 1:1) to give the titled compound (1.4 g, 99%) as a brown oil.

(2) Preparation of (2R)-1-[4-(4-iodophenoxy)butyl]-2-methylpyrrolidine

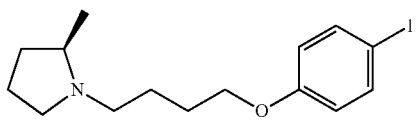

[Formula 105]

To a suspension of (2R)-2-methylpyrrolidine (0.8 g) and cesium carbonate (1.7 g) in acetonitrile (5 mL), 1-(4-chlorobutoxy)-4-iodobenzene obtained in Example 61-(1) (1.4 g) was added and the mixture was heated to 100° C., at which it was stirred for 9 hours. The reaction mixture was cooled to room temperature and filtered to remove insoluble materials, and the filtrate was concentrated under reduced pressure. The resulting residue was purified by NH-type silica gel column chromatography (eluting solvent: n-hexane:ethyl acetate=9:1 to 1:1) to give the titled compound (1.4 g, 89%) as a colorless oil.

(3) Preparation of [1-(4-{4-[(2R)-2-methylpyrrolidin-1-yl]butoxy}phenyl)-1H-pyrazol-4-yl](morpholin-4-yl)methanone

[Formula 106]

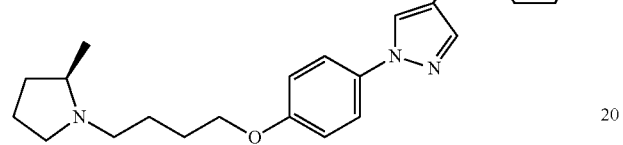

The same procedure as shown in Example 6 was repeated to give the titled compound, except that (2R)-1-[3-(4-iodophenoxy)propyl]-2-methylpyrrolidine was replaced by (2R)-1-[2-(4-iodophenoxy)ethyl]-2-methylpyrrolidine obtained in Example 61-(2) (0.8 g).

1H NMR (600 MHz, CHLOROFORM-d) δ ppm 1.10 (d, J=6.0 Hz, 3H), 1.38-1.47 (m, 1H), 1.63-1.96 (m, 7H), 2.03-2.12 (m, 2H), 2.22-2.31 (m, 1H), 2.79-2.88 (m, 1H), 3.14-3.21 (m, 1H), 3.71-3.81 (m, 8H), 4.02 (t, J=6.4 Hz, 2H), 6.94-7.01 (m, 2H), 7.53-7.59 (m, 2H), 7.79 (s, 1H), 8.14 (s, 1H)

MS (ESI/APCI Dual) (Positive) m/z; 413 (M+H)+

Example 62

Preparation of [1-(3-fluoro-4-{3-[(2R)-2-methylpyrrolidin-1-yl]propoxy}phenyl)-1H-pyrazol-4-yl](morpholin-4-yl)methanone (1) Preparation of (2R)-1-(3-chloropropyl)-2-methylpyrrolidine

[Formula 107]

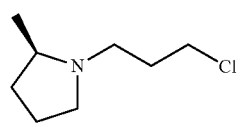

To a solution of (R)-2-methylpyrrolidine (18.0 g) and 1-bromo-3-chloropropane (100.0 g) in acetone (360 mL), aqueous sodium hydroxide (5 M, 50 mL) was added dropwise in an ice bath and the mixture was heated to 80° C., at which it was stirred for 4 hours. The reaction mixture was extracted with diethyl ether, and the organic layer was washed with brine, dried over anhydrous sodium sulfate and concentrated under reduced pressure. The resulting residue was purified by NH-type silica gel column chromatography (eluting solvent: n-hexane:ethyl acetate=4:1 to 1:1) and silica gel column chromatography (eluting solvent: chloroform:methanol=9:1) to give the titled compound (17.8 g, 52%) as a yellow oil.

(2) Preparation of (2R)-1-[3-(4-bromo-2-fluorophenoxy)propyl]-2-methylpyrrolidine

[Formula 108]

To a suspension of 4-bromo-2-fluorophenol (0.57 g) and cesium carbonate (1.6 g) in acetonitrile (2.5 mL), (2R)-1-(3-chloropropyl)-2-methylpyrrolidine obtained in Example 62-(1) (0.40 g) was added and the mixture was heated to 100° C., at which it was stirred for 4 hours. The reaction mixture was cooled to room temperature and filtered to remove insoluble materials, and the filtrate was concentrated under reduced pressure. The resulting residue was purified by NH-type silica gel column chromatography (eluting solvent: n-hexane:ethyl acetate=10:1 to 3:1) to give the titled compound (0.73 g, 94%) as a yellow oil.

(3) Preparation of [1-(3-fluoro-4-{3-[(2R)-2-methylpyrrolidin-1-yl]propoxy}phenyl)-1H-pyrazol-4-yl](morpholin-4-yl)methanone

[Formula 109]

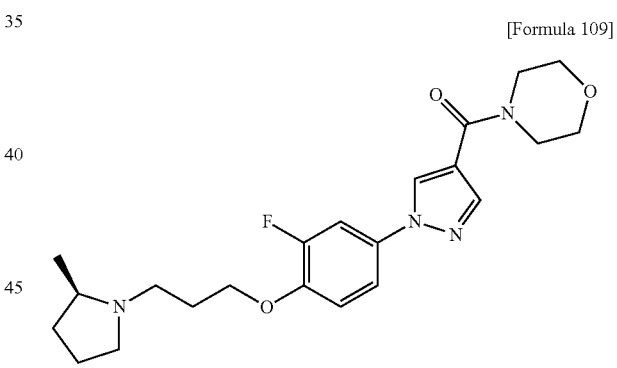

To a solution of (2R)-1-[3-(4-bromo-2-fluorophenoxy)propyl]-2-methylpyrrolidine obtained in Example 62-(2) (0.72 g) and morpholin-4-yl(1H-pyrazol-4-yl)methanone (0.45 g) in N,N-dimethylformamide (3 mL), cesium carbonate (1.6 g), copper iodide (0.1 g) and (1R,2R)—N,N'-dimethylcyclohexane-1,2-diamine (0.36 mL) were added and the mixture was heated to 130° C., at which it was stirred for 6 hours. The reaction mixture was cooled to room temperature and filtered to remove insoluble materials, and the filtrate was concentrated under reduced pressure. The resulting residue was purified by silica gel column chromatography (eluting solvent: chloroform:methanol=11:1 to 3:1) and NH-type silica gel column chromatography (eluting solvent: chloroform:methanol=10:0 to 100:1) to give the titled compound (0.34 g, 36%) as a colorless solid.

1H NMR (600 MHz, CHLOROFORM-d) δ ppm 1.09 (d, J=6.0 Hz, 3H), 1.37-1.47 (m, 1H), 1.66-1.74 (m, 1H), 1.74-1.83 (m, 1H), 1.87-1.96 (m, 1H), 1.99-2.08 (m, 2H), 2.08-

2.16 (m, 1H), 2.18-2.27 (m, 1H), 2.27-2.35 (m, 1H), 2.96-3.05 (m, 1H), 3.13-3.21 (m, 1H), 3.70-3.81 (m, 8H), 4.10-4.21 (m, 2H), 7.02-7.09 (m, 1H), 7.32-7.37 (m, 1H), 7.45-7.51 (m, 1H), 7.76-7.81 (m, 1H), 8.14 (s, 1H)

MS (ESI/APCI Dual) (Positive) m/z; 417 (M+H)+

Example 63

Preparation of [1-(2-methyl-4-{3-[(2R)-2-methylpyrrolidin-1-yl]propoxy}phenyl)-1H-pyrazol-4-yl](morpholin-4-yl)methanone

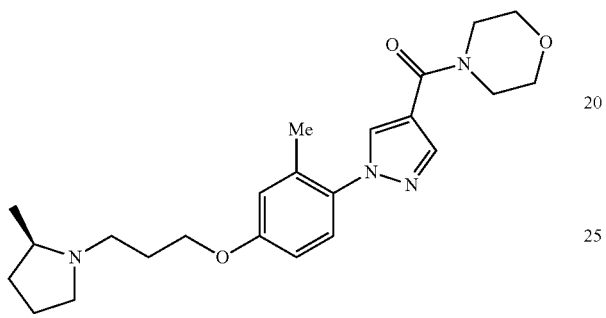

[Formula 110]

The same procedure as shown in Example 62 was repeated to give the titled compound, except that 4-bromo-2-fluorophenol was replaced by 4-bromo-3-methylphenol.

1H NMR (600 MHz, CHLOROFORM-d) δ ppm 1.10 (d, J=6.0 Hz, 3H), 1.39-1.48 (m, 1H), 1.67-1.74 (m, 1H), 1.75-1.84 (m, 1H), 1.89-1.97 (m, 1H), 1.98-2.06 (m, 2H), 2.09-2.16 (m, 1H), 2.18 (s, 3H), 2.20-2.25 (m, 1H), 2.26-2.35 (m, 1H), 2.95-3.04 (m, 1H), 3.15-3.22 (m, 1H), 3.72-3.82 (m, 8H), 4.02-4.10 (m, 2H), 6.80 (dd, J=8.7, 2.8 Hz, 1H), 6.84 (d, J=2.8 Hz, 1H), 7.21 (d, J=8.7 Hz, 1H), 7.81 (s, 1H), 7.86 (s, 1H)

MS (ESI/APCI Dual) (Positive) m/z; 413 (M+H)+

Example 64

Preparation of [1-(3-bromo-4-{3-[(2R)-2-methylpyrrolidin-1-yl]propoxy}phenyl)-1H-pyrazol-4-yl](morpholin-4-yl)methanone

[Formula 111]

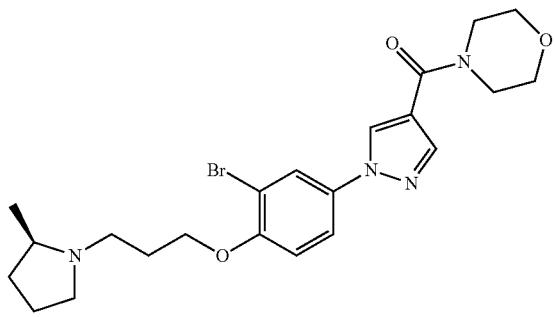

To a solution of 4-{[1-(4-{3-[(2R)-2-methylpyrrolidin-1-yl]propoxy}phenyl)-1H-pyrazol-4-yl]carbonyl}morpholine obtained in Example 6 (0.500 g) in acetic acid (8.0 ml), bromine (0.200 g) was added dropwise and stirred overnight at room temperature. The reaction mixture was diluted with saturated aqueous sodium thiosulfate and concentrated under reduced pressure. The resulting residue was diluted with saturated aqueous sodium bicarbonate and extracted with chloroform. The organic layer was concentrated under reduced pressure, and the resulting residue was purified by NH-type silica gel column chromatography (eluting solvent: n-hexane:ethyl acetate=1:1) to give the titled compound (0.175 g) as a colorless solid.

1H NMR (600 MHz, CHLOROFORM-d) δ ppm 1.02-2.37 (m, 12H), 3.01-3.23 (m, 2H), 3.71-3.79 (m, 8H), 4.10-4.17 (m, 2H), 6.97 (d, J=8.7 Hz, 1H), 7.54 (dd, J=8.7, 2.8 Hz, 1H), 7.78 (s, 1H), 7.89 (d, J=2.8 Hz, 1H), 8.12 (s, 1H)

MS (ESI/APCI Dual) (Positive) m/z; 477 (M+H)+

Example 65

Preparation of (2-hydroxymorpholin-4-yl)[1-(4-{3-[(2R)-2-methylpyrrolidin-1-yl]propoxy}phenyl)-1H-pyrazol-4-yl]methanone

[Formula 112]

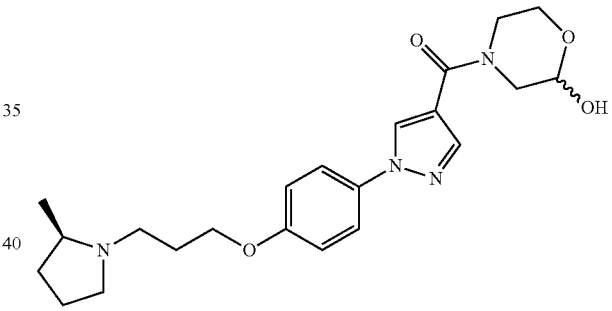

To a solution of 1-(4-{3-[(2R)-2-methylpyrrolidin-1-yl]propoxy}phenyl)-1H-pyrazole-4-carboxylic acid bis-(2-hydroxyethyl)-amide obtained in Example 20 (1.0 g) in chloroform (8 mL), Dess-Martin reagent (1.1 g) was added and stirred at room temperature for 16 hours. The reaction mixture was diluted with water and extracted with chloroform. The organic layer was washed with brine, dried over magnesium sulfate and concentrated under reduced pressure. The resulting residue was purified by silica gel column chromatography (eluting solvent: chloroform:methanol=4:1) and further purified by preparative TLC (1 mm thickness, developing solvent: chloroform:methanol=9:1) to give the titled compound (0.022 g) as a colorless amorphous substance.

1H NMR (600 MHz, CHLOROFORM-d) δ ppm 1.13 (d, J=6.0 Hz, 3H), 1.40-2.49 (m, 10H), 2.97-3.07 (m, 1H), 3.23 (br.s, 1H), 3.49-4.20 (m, 7H), 5.07 (t, J=3.2 Hz, 1H), 6.97 (d, J=8.7 Hz, 2H), 7.55 (d, J=8.7 Hz, 2H), 7.87 (br.s, 1H), 8.19 (s, 1H)

MS (ESI/APCI Dual) (Positive) m/z; 415 (M+H)+

Example 66

Preparation of N-(2-hydroxyethyl)-1-(4-{3-[(2R)-2-methylpyrrolidin-1-yl]propoxy}phenyl)-1H-pyrazole-4-carboxamide

[Formula 113]

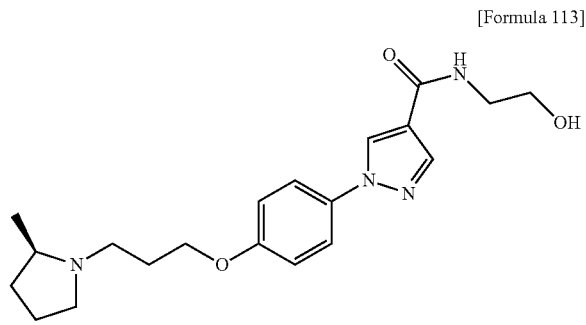

A mixture of 1-(4-{3-[(2R)-2-methylpyrrolidin-1-yl]propoxy}phenyl)-1H-pyrazole-4-carboxylic acid hydrochloride prepared in Example 2-(1) (1.00 g), 2-aminoethanol (0.400 g), 1-ethyl-3-(3-dimethylaminopropyl)carbodiimide hydrochloride (0.580 g), 1-hydroxybenzotriazole monohydrate (0.460 g) and N,N-dimethylformamide (10 mL) was stirred at room temperature for 4 days. The reaction mixture was concentrated under reduced pressure, and the resulting residue was purified by silica gel column chromatography (eluting solvent: chloroform:methanol=18:1) to give the titled compound (0.920 g) as a colorless solid.

1H NMR (600 MHz, CHLOROFORM-d) δ ppm 1.09 (d, J=6.0 Hz, 3H), 1.37-1.47 (m, 1H), 2.21 (s, 8H), 2.93-3.25 (m, 2H), 3.56-3.64 (m, 2H), 3.79-3.86 (m, 2H), 4.00-4.09 (m, 2H), 6.34-6.41 (m, 1H), 6.97 (d, J=9.2 Hz, 2H), 7.55 (d, J=9.2 Hz, 2H), 7.91 (s, 1H), 8.28 (s, 1H)

MS (ESI/APCI Dual) (Positive) m/z; 373 (M+H)$^+$

Example 67

Preparation of tert-butyl N-(2-hydroxyethyl)-N-{[1-(4-{3-[(2R)-2-methylpyrrolidin-1-yl]propoxy}phenyl)-1H-pyrazol-4-yl]carbonyl}glycinate (1) Preparation of N-{2-(tert-butyldimethylsilyloxy)ethyl}-1-(4-{3-[(2R)-2-methylpyrrolidin-1-yl]propoxy}phenyl)-1H-pyrazole-4-carboxamide

[Formula 114]

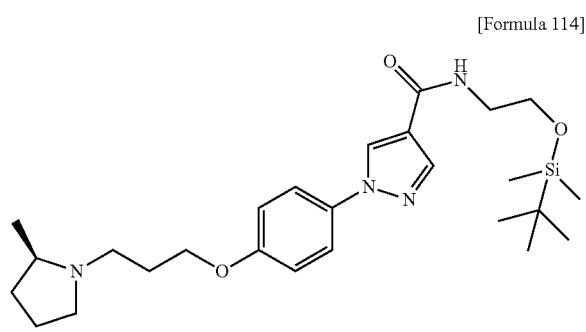

A mixture of N-(2-hydroxyethyl)-1-(4-{3-[(2R)-2-methylpyrrolidin-1-yl]propoxy}phenyl)-1H-pyrazole-4-carboxamide prepared in Example 66 (0.500 g), tert-butylchlorodimethylsilane (0.303 g), imidazole (0.273 g) and N,N-dimethylformamide (5.0 mL) was stirred overnight at room temperature. The reaction mixture was diluted with brine and extracted with ethyl acetate. The organic layer was dried over magnesium sulfate and concentrated under reduced pressure. The resulting residue was purified by silica gel column chromatography (eluting solvent: n-hexane:ethyl acetate=1:1) to give the titled compound (0.550 g) as a colorless solid.

(2) Preparation of tert-butyl N-{2-(tert-butyldimethylsilyloxy)ethyl}-N-{[1-(4-{3-[(2R)-2-methylpyrrolidin-1-yl]propoxy}phenyl)-1H-pyrazol-4-yl]carbonyl}glycinate

[Formula 115]

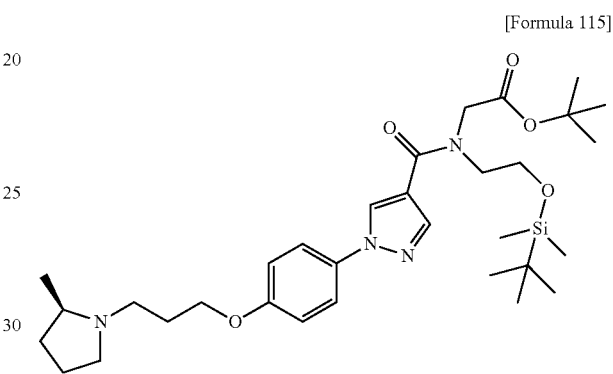

To a solution of N-{2-(tert-butyldimethylsilyloxy)ethyl}-1-(4-{3-[(2R)-2-methylpyrrolidin-1-yl]propoxy}phenyl)-1H-pyrazole-4-carboxamide prepared in Example 67-(1) (0.700 g) in N,N-dimethylformamide (5.0 mL), sodium hydride (55% in mineral oil, 0.058 g) was added and stirred at room temperature for 20 minutes. To the reaction mixture, tert-butyl 2-bromoacetate (0.281 g) was added and stirred for 30 minutes. The reaction mixture was diluted with water and extracted with ethyl acetate. The organic layer was dried over magnesium sulfate and concentrated under reduced pressure. The resulting residue was purified by silica gel column chromatography (eluting solvent: n-hexane:ethyl acetate=1:1) to give the titled compound (0.220 g) as a colorless oil.

(3) Preparation of tert-butyl N-(2-hydroxyethyl)-N-{[1-(4-{3-[(2R)-2-methylpyrrolidin-1-yl]propoxy}phenyl)-1H-pyrazol-4-yl]carbonyl}glycinate

[Formula 116]

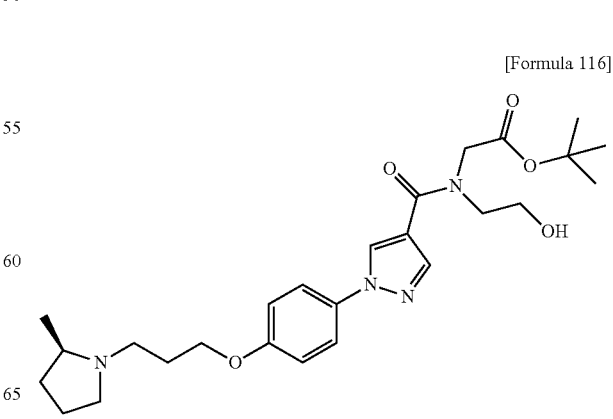

To a solution of tert-butyl N-{2-(tert-butyldimethylsilyloxy)ethyl}-N-{[1-(4-{3-[(2R)-2-methylpyrrolidin-1-yl]propoxy}phenyl)-1H-pyrazol-4-yl]carbonyl}glycinate prepared in Example 67-(2) (0.220 g) in tetrahydrofuran (2.0 ml), a solution of tetrabutylammonium fluoride in tetrahydrofuran (1.0 M, 0.37 ml) was added and stirred at room temperature for 30 minutes. The reaction mixture was concentrated under reduced pressure, and the resulting residue was purified by silica gel column chromatography (eluting solvent: chloroform:methanol=18:1) to give the titled compound (0.180 g) as a colorless oil.

1H NMR (600 MHz, CHLOROFORM-d) δ ppm 1.09 (d, J=6.0 Hz, 3H), 1.37-2.38 (m, 22H), 2.92-4.26 (m, 6H), 6.94-7.20 (m, 2H), 7.20-7.28 (m, 2H), 7.49-7.60 (m, 1H), 7.71-8.42 (m, 1H)

MS (ESI/APCI Dual) (Positive) m/z; 487 (M+H)+

Example 68

Preparation of N-(2-hydroxyethyl)-N-{[1-(4-{3-[(2R)-2-methylpyrrolidin-1-yl]propoxy}phenyl)-1H-pyrazol-4-yl]carbonyl}glycine

[Formula 117]

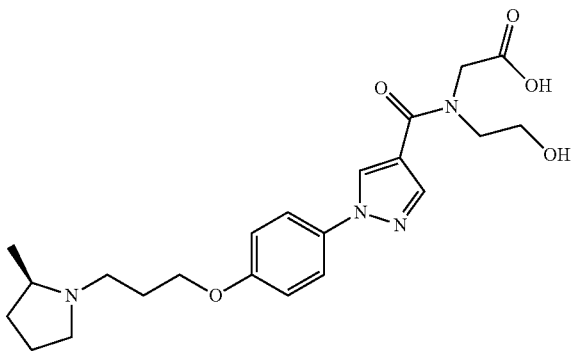

To a solution of tert-butyl N-(2-hydroxyethyl)-N-{[1-(4-{3-[(2R)-2-methylpyrrolidin-1-yl]propoxy}phenyl)-1H-pyrazol-4-yl]carbonyl}glycinate prepared in Example 67-(3) (0.218 g) in 1,4-dioxane (4.0 ml), a solution of hydrochloric acid in ethyl acetate (4 M, 4.0 ml) was added and stirred at room temperature for 1 hour. The reaction mixture was concentrated under reduced pressure, and the resulting residue was purified by octadecylsilyl (ODS) column chromatography (eluting solvent: acetonitrile:water=95:5) to give the titled compound (0.075 g) as a colorless amorphous substance.

1H NMR (600 MHz, METHANOL-d3) δ ppm 1.37-1.50 (m, 3H), 1.70-1.81 (m, 1H), 1.91-2.34 (m, 5H), 3.12-3.24 (m, 1H), 3.43-3.61 (m, 3H), 3.65-3.83 (m, 5H), 4.12 (br. s., 4H), 7.03 (s, 2H), 7.60-7.66 (m, 2H), 7.88-8.04 (m, 1H), 8.30-8.54 (m, 1H)

MS (ESI/APCI Dual) (Positive) m/z; 431 (M+H)+

Example 69

Preparation of N-[2-(2-hydroxyethoxy)ethyl]-1-{4-[3-(2-methylpyrrolidin-1-yl)propoxy]phenyl}-1H-pyrazole-4-carboxamide

[Formula 118]

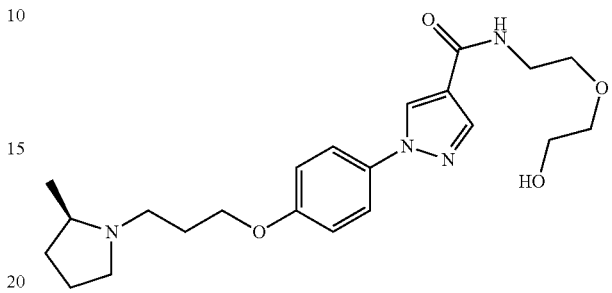

The same procedure as shown in Example 2-(2) was repeated to give the titled compound, except that aqueous ammonia was replaced by 2-(2-aminoethoxy)ethanol.

1H NMR (600 MHz, CHLOROFORM-d) δ ppm 1.03-1.13 (m, 3H), 1.37-2.34 (m, 9H), 2.94-3.01 (m, 1H), 3.14-3.21 (m, 1H), 3.61-3.70 (m, 6H), 3.76-3.81 (m, 2H), 4.01-4.09 (m, 2H), 6.39-6.44 (m, 1H), 6.97 (d, J=9.2 Hz, 2H), 7.55 (d, J=9.2 Hz, 2H), 7.92 (s, 1H), 8.27 (s, 1H)

MS (ESI/APCI Dual) (Positive) m/z; 417 (M+H)+

Example 70

Preparation of 4-{[1-(4-{3-[(2R)-2-methylpyrrolidin-1-yl]propoxy}phenyl)-1H-pyrazol-4-yl]carbonyl}morpholine monohydrochloride

[Formula 119]

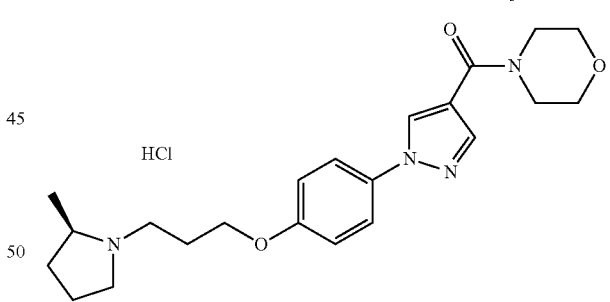

To a solution of 4-{[1-(4-{3-[(2R)-2-methylpyrrolidin-1-yl]propoxy}phenyl)-1H-pyrazol-4-yl]carbonyl}morpholine obtained in Example 6-(2) (2.62 g) in ethyl acetate (18 mL), a solution of hydrochloric acid in ethyl acetate (4 M, 2.46 mL) was added and stirred at room temperature for 30 minutes. The precipitated crystal was collected by filtration to give a crude crystal (2.9 g). A suspension of the resulting crude crystal in ethanol (9 mL) was heated under reflux to give a solution, which was then filtered. After addition of ethanol (6 mL), the filtrate was stirred for 30 minutes while cooling to room temperature. The mixture was further stirred in an ice bath for 1.5 hours, and the precipitated crystal was collected by filtration and dried to give the titled compound (2.67 g) as a colorless powder.

1H NMR (600 MHz, DMSO-$d_6$) δ ppm 1.10-1.43 (m, 3H), 1.54-2.24 (m, 6H), 2.99-3.23 (m, 2H), 3.33-3.52 (m, 2H), 3.47-3.89 (m, 9H), 4.02-4.19 (m, 2H), 7.01-7.10 (m, 2H), 7.73-7.82 (m, 2H), 7.90 (s, 1H), 8.69 (s, 1H)

IR (KBr, $cm^{-1}$) 750, 827, 944, 996, 1048, 1119, 1251, 1439, 1518, 1552, 1602, 2453, 2552, 2865

Elemental analysis for $C_{22}H_{30}N_4O_3 \times 1HCl$
Calculated: C, 60.75%; H, 7.18%; N, 12.88%.
Found: C, 60.55%; H, 7.12%; N, 12.81%.
Melting point: 203.0° C.
Thermogravimetry: no change until the melting point (203.0° C.)

Example 71

Preparation of 4-{[1-(4-{3-[(2R)-2-methylpyrrolidin-1-yl]propoxy}phenyl)-1H-pyrazol-4-yl]carbonyl}morpholine monohydrochloride dihydrate

[Formula 120]

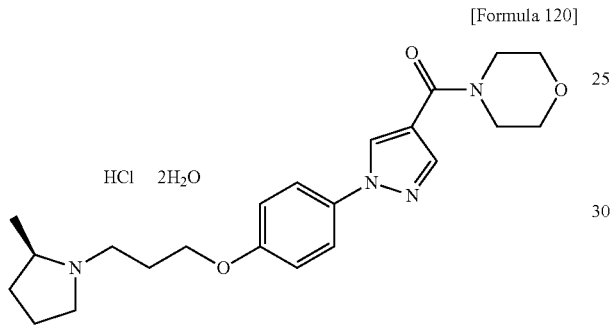

4-{[1-(4-{3-[(2R)-2-Methylpyrrolidin-1-yl]propoxy}phenyl)-1H-pyrazol-4-yl]carbonyl}morpholine monohydrochloride obtained in Example 70 was placed in a desiccator adjusted to a humidity of 93% and stored for 2 days to give the titled compound as a colorless powder.

Thermogravimetry: 7.32% reduction (corresponding to $2H_2O$) at around 51° C.

Example 72

Preparation of 4-{[1-(4-{3-[(2R)-2-methylpyrrolidin-1-yl]propoxy}phenyl)-1H-pyrazol-4-yl]carbonyl}morpholine monohydrobromide

[Formula 121]

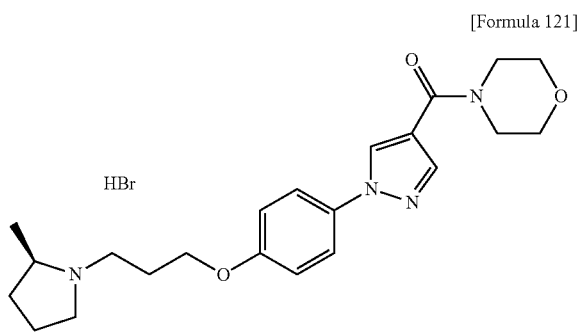

To a solution of 4-{[1-(4-{3-[(2R)-2-methylpyrrolidin-1-yl]propoxy}phenyl)-1H-pyrazol-4-yl]carbonyl}morpholine obtained in Example 6-(2) (1.0 g) in ethanol (5 mL), a solution of hydrobromic acid in ethanol (1.5 M, 2.0 mL) was added and stirred at room temperature for 3 hours. The reaction mixture was concentrated under reduced pressure, followed by addition of an ethanol:methanol solution (95:5, 10 mL) to give a solution. This solution was stirred for 3 hours while cooling in an ice bath. The precipitated solid was collected by filtration and dried to give the titled compound (1.1 g) as a colorless powder.

1H NMR (600 MHz, DMSO-$d_6$) δ ppm 1.12-1.43 (m, 3H), 1.54-1.67 (m, 1H), 1.84-2.28 (m, 5H), 3.08-3.18 (m, 2H), 3.41-3.51 (m, 2H), 3.57-3.73 (m, 9H), 4.09-4.16 (m, 2H), 7.09 (d, J=9.2 Hz, 2H), 7.81 (d, J=9.2 Hz, 2H), 7.91-7.96 (m, 1H), 8.72 (s, 1H), 9.25 (br. s., 1H)

IR (KBr, $cm^{-1}$) 751, 828, 944, 996, 1047, 1119, 1251, 1438, 1519, 1552, 1604, 2519, 2603, 2866

Elemental analysis for $C_{22}H_{30}N_4O_3 \times 1HBr$
Calculated: C, 55.12%; H, 6.52%; N, 11.69%.
Found: C, 54.99%; H, 6.44%; N, 11.67%.
Melting point: 202.0° C.

Test Example 1

H3 Receptor Binding Test

A membrane preparation of human H3 receptor-expressing CHO-K1 cells (Euroscreen, ES-392-M, 15 μg protein/200 μl), R(-)-α-methyl[$^3$H]histamine (Amersham, TRK-1017, specific activity: 1.74 TBq/mmol, 2 nM) and a test drug were reacted at room temperature for 1 hour. After completion of the reaction, the reaction mixture was subjected to suction filtration through a 0.3% polyethyleneimine-treated glass filter (GF/C). The glass filter was washed five times with 50 mM Tris-HCl washing solution (pH 7.4) containing 5 mM EDTA. After washing, the glass filter was dried and a scintillator was added thereto, followed by measurement of radioactivity on the filter using a liquid scintillation counter.

Binding of R(-)-α-methyl[$^3$H]histamine in the presence of 10 μM R(-)-α-methylhistamine was defined as non-specific binding, and the difference between total binding and non-specific binding of R(-)-α-methyl[$^3$H]histamine was defined as specific binding of R(-)-α-methyl[$^3$H]histamine. A fixed concentration (2 nM) of R(-)-α-methyl[$^3$H]histamine was reacted under the above conditions with each test drug at various concentrations to obtain an inhibition curve. The inhibition curve was used to determine the concentration ($IC_{50}$) of each test drug required for 50% inhibition of R(-)-α-methyl [$^3$H]histamine binding. The $IC_{50}$ values of the compounds prepared in the examples are shown in Table 1.

TABLE 1

| Example | $IC_{50}$ (nM) |
| --- | --- |
| 1 | 24.0 |
| 2 | 6.5 |
| 3 | 4.6 |
| 4 | 33.0 |
| 5 | 10.8 |
| 6 | 4.9 |
| 7 | 12.5 |
| 8 | 24.2 |
| 9 | 8.5 |
| 10 | 49.4 |
| 11 | 1.8 |
| 12 | 19.3 |
| 13 | 6.1 |
| 14 | 13.5 |
| 15 | 1.8 |

TABLE 1-continued

| Example | IC$_{50}$ (nM) |
|---|---|
| 16 | 5.9 |
| 17 | 3.9 |
| 18 | 3.0 |
| 19 | 5.1 |
| 20 | 6.9 |
| 21 | 5.7 |
| 22 | 2.7 |
| 23 | 2.2 |
| 24 | 3.3 |
| 25 | 3.5 |
| 26 | 2.6 |
| 27 | 1.6 |
| 28 | 3.1 |
| 29 | N.T. |
| 30 | 3.3 |
| 31 | 5.1 |
| 32 | 8.3 |
| 33 | N.T. |
| 34 | 2.1 |
| 35 | N.T. |
| 36 | 4.0 |
| 37 | 2.1 |
| 38 | 0.9 |
| 39 | 3.5 |
| 40 | 4.4 |
| 41 | 2.1 |
| 42 | 1.7 |
| 43 | 1.0 |
| 44 | 0.8 |
| 45 | 1.1 |
| 46 | 1.4 |
| 47 | 1.5 |
| 48 | 4.1 |
| 49 | 3.1 |
| 50 | 31.9 |
| 51 | 13.7 |
| 52 | 6.0 |
| 53 | 6.1 |
| 54 | 4.1 |
| 55 | 5.2 |
| 56 | 2.8 |
| 57 | 50.7 |
| 58 | 8.7 |
| 59 | 1181 |
| 60 | 1560 |
| 61 | 39.2 |
| 62 | 8.7 |
| 63 | 20.7 |
| 64 | 10.0 |
| 65 | 5.9 |
| 66 | N.T. |
| 67 | N.T. |
| 68 | 74.8 |
| 69 | 4.6 |

N.T. denotes "Not Tested."

Test Example 2

[$^{35}$S]GTP-γ-S Binding Test

The same human H3 receptor membrane preparation as used in Test Example 1 (7.5 μg protein/100 μl), 30 μM GDP, 100 μM R(−)-α-methylhistamine and a test compound were reacted at room temperature for 30 minutes. After completion of the reaction, [$^{35}$S]GTP-γ-S (0.2 nM) was added and reacted for an additional 30 minutes. After completion of the reaction, the reaction mixture was subjected to suction filtration through a glass filter (GF/C). The glass filter was washed three times with 20 mM HEPES washing solution (pH 7.4) containing 100 mM sodium chloride and 1 mM magnesium chloride. After washing, the glass filter was dried and a scintillator was added thereto, followed by measurement of radioactivity on the filter using a liquid scintillation counter.

Binding of [$^{35}$S]GTP-γ-S in the absence of R(−)-α-methylhistamine was defined as non-specific binding, and the difference between total binding in the presence of R(−)-α-methylhistamine and non-specific binding was defined as specific binding of [$^{35}$S]GTP-γ-S. Fixed concentrations of [$^{35}$S]GTP-γ-S (0.2 nM) and R(−)-α-methylhistamine (100 μM) were reacted under the above conditions with each test drug at various concentrations to obtain an inhibition curve. The inhibition curve was used to determine the concentration (IC$_{50}$) of each test drug required for 50% inhibition of [$^{35}$S] GTP-γ-S binding. As a result, the compound of Example 6 was found to have an IC$_{50}$ value of 3.1 nM, and the compound of Example 30 was found to have an IC$_{50}$ value of 1.7 nM.

Test Example 3

[$^3$H]diprenorphine Binding Test

Affinity for μ receptor was evaluated in a [$^3$H]diprenorphine binding test by Cerep, Inc. The μ receptor preparation used was human recombinant μ receptor. The human recombinant μ receptor was incubated with [$^3$H]diprenorphine (0.4 nM) at 22° C. for 120 minutes. Binding of [$^3$H]diprenorphine in the presence of 1 μM naltrexone was defined as non-specific binding, and the difference between total binding and non-specific binding of [$^3$H]diprenorphine was defined as specific binding of [$^3$H]diprenorphine.

Test Example 4

[$^3$H]DADLE Binding Test

Affinity for δ receptor was evaluated in a [$^3$H]DADLE binding test by Cerep, Inc. The δ receptor preparation used was human recombinant δ receptor. The human recombinant δ receptor was incubated with [$^3$H]DADLE (0.5 nM) at 22° C. for 120 minutes. Binding of [$^3$H]DADLE in the presence of 10 μM naltrexone was defined as non-specific binding, and the difference between total binding and non-specific binding of [$^3$H]DADLE was defined as specific binding of [$^3$H] DADLE.

Test Example 5

[$^3$H](+)pentazocine Binding Test

Affinity for σ1 receptor was evaluated in a [$^3$H](+)pentazocine binding test by Cerep, Inc. The σ1 receptor preparation used was the membrane of Jurkat cells. The Jurkat cell membrane was incubated with [$^3$H](+)pentazocine (8 nM) at 22° C. for 120 minutes. Binding of [$^3$H](+)pentazocine in the presence of 10 μM haloperidol was defined as non-specific binding, and the difference between total bonding and non-specific binding of [$^3$H](+)pentazocine was defined as specific binding of [$^3$H](+)pentazocine.

Test Example 6

[$^3$H]U69593 Binding Test

Affinity for κ receptor was evaluated in a [$^3$H]U69593 binding test by Cerep, Inc. The κ receptor preparation used was rat recombinant κ receptor. The rat recombinant κ receptor was incubated with [$^3$H]U69593 (1 nM) at 22° C. for 60 minutes. Binding of [$^3$H]U69593 in the presence of 10 μM naloxone was defined as non-specific binding, and the difference between total binding and non-specific binding of [$^3$H]U69593 was defined as specific binding of [$^3$H]U69593.

Table 2 shows the % inhibition of binding to each ligand caused by the compound of Example 70 at 10 μM concentration in Test Examples 3 to 6.

TABLE 2

Opioid receptor binding test

| Receptor | % Inhibition (10 μM) |
|---|---|
| μ | 3 |
| δ | −1 |
| σ1 | 28 |
| κ | 17 |

Likewise, in Test Example 5, the compounds of Examples 54 and 55 at 10 μM concentration were found to show 39% and 3% inhibition of ligand binding, respectively.

Test Example 7

Metabolic Stability Test in Human Liver

Using human liver microsome (Xenotech, H0630), the in vitro metabolic half-life was calculated. A reaction solution (300 μL) was prepared to contain a test compound at 1 μM in 250 mM Na—K-phosphate buffer (pH 7.4) containing, at final concentrations, 2.4 mM $MgCl_2$, 1.5 mM glucose-6-phosphate (G-6-P), 0.18 U/mL glucose-6-phosphate dehydrogenase (G-6-P DH), 69 mM KCl, 0.16 mM (3-nicotinamide-adenine dinucleotide phosphate, oxidized form (NADP) and 1 mg microsomal protein/mL. After pre-incubation at 37° C. for 5 minutes, the NADP solution was added to initiate the reaction. The incubation time was set to 0, 10, 20, 30, 45 or 60 minutes. The reaction was stopped by addition of a $CH_3CN:CH_3OH$ (1:1) solution in the same volume as that of the reaction solution. The sample after the reaction was centrifuged at 3639×g at 4° C. for 10 minutes, and the resulting supernatant was analyzed by LC/MS. Using the time period during which linearity was observed, the metabolic half-life was calculated from the slope. As a result, the compound of Example 6 was found to have a metabolic half-life of 180 minutes or longer.

Test Example 8

Social Recognition Test

This experiment was performed with Sprague-Dawley rats (male) according to the reported method (Shimazaki et al., European Journal of Pharmacology, 575, 94-97, 2007). Adult rats (9 weeks of age) were placed in a test cage and acclimated for 30 minutes. After 30 minutes, juvenile rats (4 weeks of age) were placed in the same test cage containing the adult rats, and allowed to stand for 5 minutes. During this 5 minutes, the time taken for the adult rats to show social behavior (sniffing, grooming, following) to the juvenile rats was measured (first exploratory time). Then, the rats were removed from the test cage and returned to their respective home cages. After 85 minutes, the adult rats were placed again in the test cage and acclimated for 30 minutes. The same juvenile rats as used in the first exploratory were placed in the test cage, followed by measuring the time taken for the adult rats to show social behavior (sniffing, grooming, following) to the juvenile rats during 5 minutes (second exploratory time). The social recognition was expressed as the ratio of second exploratory time/first exploratory time. A test substance (the compound of Example 70) was orally administered to the adult rats immediately after their first social behavior. The results obtained are shown in Table 3.

TABLE 3

| | Ratio (second exploratory time/first exploratory time) |
|---|---|
| Vehicle group | 0.87 ± 0.05 |
| Test substance (10 mg/kg) group | 0.66 ± 0.06$^{p<0.01}$ | n = 18, statistical significance was analyzed by t-test

The test substance group showed a significant reduction in the ratio of second exploratory time/first exploratory time when compared to the vehicle group, thus indicating that the test substance had an enhancing effect on cognitive functions.

Test Example 9

Distribution Test in Rats

SD rats were used and orally administered once with the compound of Example 70 at a dose of 3 mg/kg (2.75 mg/kg as a free form) to confirm the tissue distribution of the compound in plasma, brain, liver, kidney, spleen, lung, heart, muscle, fat, testis, bone marrow and adrenal gland at 1, 2, 4, 8 and 24 hours after administration. For quantification, high performance liquid chromatography/tandem mass spectrometry (LC-MS/MS) was used. As a result, in the case of the compound of Example 70, the unchanged form and major metabolites of its free form (i.e., the compound of Example 6) were found to rapidly disappear from each organ.

Test Example 10

Cytotoxicity Test

Chinese hamster lung fibroblast-derived CHL/IU cells (DS Pharma Biomedical Co., Ltd., Japan) were seeded, and the medium was replaced on the following day by another medium (MEM+2 mM L-Glutamine+10% CS (all purchased from Invitrogen)) containing a test compound at various concentrations, followed by culture for an additional 48 hours. Using a Cell counting kit-8 (Dojindo Laboratories, Japan), the survival rate of the cells was determined to obtain a curve whose horizontal axis represents the test compound concentration and whose vertical axis represents the survival rate. The curve thus obtained was used to determine the concentration of the test compound at which the survival rate was 50%. As a result, this concentration was 275, 441 and >640 mmol/L for the compounds of Examples 56, 62 and 70, respectively.

INDUSTRIAL APPLICABILITY

The present invention enables the provision of pharmaceutical preparations which have a strong inhibitory effect against binding to histamine H3 receptors and are useful for prevention or treatment of histamine H3 receptor-mediated disorders such as dementia, Alzheimer's disease, attention-deficit hyperactivity disorder, schizophrenia, epilepsy, central convulsion, eating disorders, obesity, diabetes, hyperlipidemia, sleep disorders, narcolepsy, sleep apnea syndrome, circadian rhythm disorder, depression, allergic rhinitis or other diseases. The present invention is expected to make a great contribution to the development of the pharmaceutical industry.

The invention claimed is:

1. A phenylpyrazole derivative represented by formula (1) or a pharmaceutically acceptable salt thereof:

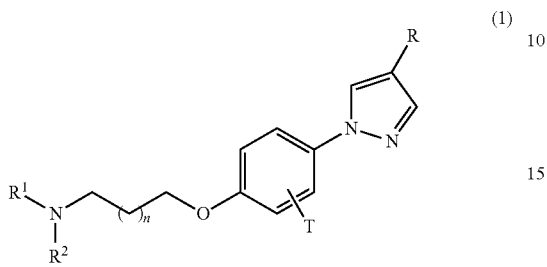

(1)

{wherein
$R^1$ and $R^2$, which may be the same or different, each represent $C_1$-$C_6$ alkyl or $C_3$-$C_8$ cycloalkyl, or
$R^1$ and $R^2$ are attached to each other together with their adjacent nitrogen atom to form a 4- to 7-membered saturated heterocyclic ring (wherein said saturated heterocyclic ring may be substituted with halogen or $C_1$-$C_6$ alkyl),
n represents an integer of 0 to 2,
T represents a hydrogen atom, halogen or $C_1$-$C_6$ alkyl, and
R represents any one of formulae (II) to (VIII):

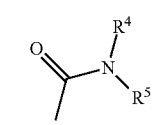 (II)

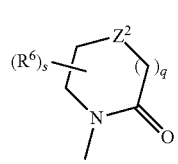 (III)

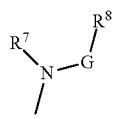 (IV)

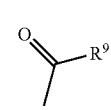 (V)

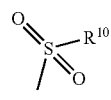 (VI)

 (VII)

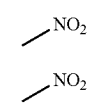 (VIII)

(wherein $Z^2$ represents —$CH_2$—, —O— or —$NR^{11}$—,
q represents an integer of 0 to 1,
s represents an integer of 0 to 2,
$R^4$ and $R^5$, which may be the same or different, each represent a hydrogen atom, $C_1$-$C_6$ alkyl (wherein said $C_1$-$C_6$ alkyl may be substituted with halogen, $C_3$-$C_8$ cycloalkyl, $C_1$-$C_6$ alkoxy, hydroxy, hydroxy-$C_1$-$C_6$ alkoxy, $C_2$-$C_7$ alkoxycarbonyl or carboxy), $C_3$-$C_8$ cycloalkyl (wherein said $C_3$-$C_8$ cycloalkyl may be substituted with halogen, $C_1$-$C_6$ alkyl, $C_1$-$C_6$ alkoxy or hydroxy) or the formula —$(CH_2)_m$—$Ar^1$ (wherein $Ar^1$ represents aryl (wherein said aryl may be substituted with halogen, $C_1$-$C_6$ alkyl, $C_1$-$C_6$ alkoxy, hydroxy or cyano) or heteroaryl (wherein said heteroaryl may be substituted with halogen, $C_1$-$C_6$ alkyl, $C_1$-$C_6$ alkoxy, hydroxy or cyano), and m represents an integer of 0 to 2),
$R^6$ represents halogen, $C_1$-$C_6$ alkyl, $C_1$-$C_6$ alkoxy, hydroxy or oxo (provided that when $Z^2$ is —$CH_2$—, the hydrogen atom(s) may be replaced by $R^6$),
$R^7$ represents a hydrogen atom or $C_1$-$C_6$ alkyl,
$R^8$ represents $C_1$-$C_6$ alkyl (wherein said $C_1$-$C_6$ alkyl may be substituted with halogen, $C_3$-$C_8$ cycloalkyl, $C_1$-$C_6$ alkoxy or hydroxy), $C_3$-$C_8$ cycloalkyl (wherein said $C_3$-$C_8$ cycloalkyl may be substituted with halogen, $C_1$-$C_6$ alkyl, $C_1$-$C_6$ alkoxy or hydroxy), $C_1$-$C_6$ alkoxy (wherein said $C_1$-$C_6$ alkoxy may be substituted with halogen, $C_3$-$C_8$ cycloalkyl, $C_1$-$C_6$ alkoxy or hydroxy) or the formula —$(CH_2)_l$—$Ar^2$ (wherein $Ar^2$ represents aryl (wherein said aryl may be substituted with halogen, $C_1$-$C_6$ alkyl, $C_1$-$C_6$ alkoxy, hydroxy or cyano) or heteroaryl (wherein said heteroaryl may be substituted with halogen, $C_1$-$C_6$ alkyl, $C_1$-$C_6$ alkoxy, hydroxy or cyano), and l represents an integer of 0 to 2),
G represents —CO— or —$SO_2$—,
$R^9$ represents $C_1$-$C_6$ alkyl, $C_3$-$C_8$ cycloalkyl, $C_1$-$C_6$ alkoxy, aryl (wherein said aryl may be substituted with halogen, $C_1$-$C_6$ alkyl, $C_1$-$C_6$ alkoxy, hydroxy or cyano) or heteroaryl (wherein said heteroaryl may be substituted with halogen, $C_1$-$C_6$ alkyl, $C_1$-$C_6$ alkoxy, hydroxy or cyano),
$R^{10}$ represents $C_1$-$C_6$ alkyl, $C_1$-$C_6$ alkoxy, amino, $C_1$-$C_6$ alkylamino, $C_2$-$C_{12}$ dialkylamino, a 4- to 7-membered saturated heterocyclic ring (wherein said saturated heterocyclic ring may be substituted with halogen, $C_1$-$C_6$ alkyl, $C_1$-$C_6$ alkoxy, hydroxy or cyano), aryl (wherein said aryl may be substituted with halogen, $C_1$-$C_6$ alkyl, $C_1$-$C_6$ alkoxy, hydroxy or cyano) or heteroaryl (wherein said heteroaryl may be substituted with halogen, $C_1$-$C_6$ alkyl, $C_1$-$C_6$ alkoxy, hydroxy or cyano), and
$R^{11}$ represents hydrogen or $C_1$-$C_6$ alkyl)}.

2. The phenylpyrazole derivative or pharmaceutically acceptable salt thereof according to claim 1, wherein in formula (1),
n is 1,
T represents a hydrogen atom or halogen, and
$R^1$ and $R^2$ are attached to each other together with their adjacent nitrogen atom to form a 5- to 6-membered saturated heterocyclic ring (wherein said saturated heterocyclic ring may be substituted with $C_1$-$C_6$ alkyl).

3. The phenylpyrazole derivative or pharmaceutically acceptable salt thereof according to claim 1, wherein in formula (1), R is formula (II).

4. The phenylpyrazole derivative or pharmaceutically acceptable salt thereof according to claim 2, wherein in formula (1), R is formula (II).

5. The phenylpyrazole derivative or pharmaceutically acceptable salt thereof according to claim 1, wherein in formula (1), R is formula (III).

6. The phenylpyrazole derivative or pharmaceutically acceptable salt thereof according to claim 2, wherein in formula (1), R is formula (III).

7. The phenylpyrazole derivative or pharmaceutically acceptable salt thereof according to claim 1, which is selected from the group consisting of:
- 1-(4-{3-[(2R)-2-methylpyrrolidin-1-yl]propoxy}phenyl)-1H-pyrazole-4-carboxamide,
- 1-(4-{3-[(2S)-2-methylpyrrolidin-1-yl]propoxy}phenyl)-1H-pyrazole-4-carboxamide,
- N-tert-butyl-1-{4-[3-(2-methylpyrrolidin-1-yl)propoxy]phenyl}-1H-pyrazole-4-carboxamide,
- N-tert-butyl-1-{4-[3-(2,5-dimethylpyrrolidin-1-yl)propoxy]phenyl}-1H-pyrazole-4-carboxamide,
- N-tert-butyl-1-[4-(3-pyrrolidin-1-ylpropoxy)phenyl]-1H-pyrazole-4-carboxamide,
- N-tert-butyl-1-{4-[3-(diethylamino)propoxy]phenyl}-1H-pyrazole-4-carboxamide,
- N-(4-fluorophenyl)-1-{4-[3-(2-methylpyrrolidin-1-yl)propoxy]phenyl}-1H-pyrazole-4-carboxamide,
- N-(4-fluorophenyl)-1-[4-(3-pyrrolidin-1-ylpropoxy)phenyl]-1H-pyrazole-4-carboxamide,
- N-(4-methylphenyl)-1-{4-[3-(2-methylpyrrolidin-1-yl)propoxy]phenyl}-1H-pyrazole-4-carboxamide,
- 1-{4-[3-(2-methylpyrrolidin-1-yl)-propoxy]-phenyl}-1H-pyrazole-4-carboxylic acid 4-fluorobenzylamide,
- 1-{4-[3-(2-methylpyrrolidin-1-yl)-propoxy]-phenyl}-1H-pyrazole-4-carboxylic acid dimethylamide,
- 1-(4-{3-[(2R)-2-methylpyrrolidin-1-yl]propoxy}phenyl)-1H-pyrazole-4-carboxylic acid bis-(2-hydroxyethyl)-amide,
- N-(2-hydroxyethyl)-1-(4-{3-[(2R)-2-methylpyrrolidin-1-yl]propoxy}phenyl)-1H-pyrazole-4-carboxamide,
- tert-butyl N-(2-hydroxyethyl)-N-{[1-(4-{3-[(2R)-2-methylpyrrolidin-1-yl]propoxy}phenyl)-1H-pyrazol-4-yl]carbonyl} glycinate,
- N-(2-hydroxyethyl)-N-{[1-(4-{3-[(2R)-2-methylpyrrolidin-1-yl]propoxy}phenyl)-1H-pyrazol-4-yl]carbonyl} glycine, and
- N-[2-(2-hydroxyethoxy)ethyl]-1-(4-{3-[(2R)-2-methylpyrrolidin-1-yl]propoxy}phenyl)-1H-pyrazole-4-carboxamide.

* * * * *